(12) United States Patent
Rebstock et al.

(10) Patent No.: US 11,266,147 B2
(45) Date of Patent: Mar. 8, 2022

(54) FUNGICIDAL OXADIAZOLES

(71) Applicants: Bayer Aktiengesellschaft, Leverkusen (DE); Bayer CropScience Aktiengesellschaft, Monheim am Rhein (DE)

(72) Inventors: Anne-Sophie Rebstock, Champagne au Mont d'or (FR); Sebastien Naud, Collonges au Mont d'Or (FR); Stephane Brunet, Saint Andre De Corcy (FR); Mathieu Gourgues, Lyons (FR); Harald Jakobi, Frankfurt (DE); Andreas Goertz, Dormagen (DE); Emmanuelle Hilt, Dizimieu (FR); Sophie Ducerf, Chasselay (FR)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 16/955,390

(22) PCT Filed: Dec. 21, 2018

(86) PCT No.: PCT/EP2018/086557
§ 371 (c)(1),
(2) Date: Jun. 18, 2020

(87) PCT Pub. No.: WO2019/122323
PCT Pub. Date: Jun. 27, 2019

(65) Prior Publication Data
US 2021/0007359 A1 Jan. 14, 2021

(30) Foreign Application Priority Data
Dec. 22, 2017 (EP) .................................... 17210460

(51) Int. Cl.
| | |
|---|---|
| *C07D 413/04* | (2006.01) |
| *A01N 43/82* | (2006.01) |
| *C07D 413/10* | (2006.01) |
| *C07D 413/14* | (2006.01) |

(52) U.S. Cl.
CPC ........... *A01N 43/82* (2013.01); *C07D 413/04* (2013.01); *C07D 413/10* (2013.01); *C07D 413/14* (2013.01)

(58) Field of Classification Search
CPC .. C07D 413/04; C07D 413/10; C07D 413/14; A01N 43/82
USPC ........................................................ 514/275
See application file for complete search history.

(56) References Cited

FOREIGN PATENT DOCUMENTS

| | | |
|---|---|---|
| WO | 2013066831 A1 | 5/2013 |
| WO | 2013080120 A1 | 6/2013 |
| WO | 2017081310 A1 | 5/2017 |
| WO | 2017110862 A1 | 6/2017 |
| WO | 2017222951 A1 | 12/2017 |
| WO | 2018187553 A1 | 10/2018 |

OTHER PUBLICATIONS

International Search Report for Application No. PCT/EP2018/086557 dated Mar. 4, 2019.

*Primary Examiner* — Kahsay Habte
(74) *Attorney, Agent, or Firm* — McBee Moore & Vanik, IP, LLC

(57) ABSTRACT

The present invention relates to heterocyclylaminophenyloxadiazole and derivatives thereof that may be used and as fungicides.

20 Claims, No Drawings

FUNGICIDAL OXADIAZOLES

TECHNICAL FIELD

The present invention relates to heterocyclylaminophenyloxadiazole and derivatives thereof that may be used and as fungicides.

BACKGROUND

Oxadiazole derivatives are known to be useful as crop protection agents to combat or prevent microorganisms' infestations. For instance, WO2017/110862 and WO2018/187553 discloses oxadiazole derivatives that may be used as fungicides.

Numerous fungicidal agents have been developed until now. However, the need remains for the development of new fungicidal compounds as such, so as to provide compounds being effective against a broad spectrum of fungi, having lower toxicity, higher selectivity, being used at lower dosage rate to reduce or avoid unfavorable environmental or toxicological effects whilst still allowing effective pest control. It may also be desired to have new compounds to prevent the emergence of fungicides resistances.

The present invention provides new fungicidal compounds which have advantages over known compounds and compositions in at least some of these aspects.

SUMMARY

The present invention relates compounds of the formula (I):

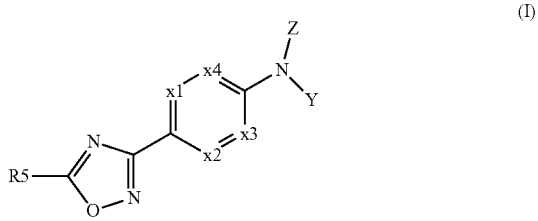

wherein X1, X2, X3, X4, $R^5$, Y and Z are as recited herein as well as their salts, N-oxides and solvates.

The present invention relates to a composition comprising at least one compound of formula (I) as defined herein and at least one agriculturally suitable auxiliary.

The present invention also relates to the use of a compound of formula (I) as defined herein or a composition as defined herein for controlling phytopathogenic fungi.

The present invention relates to a method for controlling phytopathogenic fungi which comprises the step of applying at least one compound of formula (I) as defined herein or a composition as defined herein to the plants, plant parts, seeds, fruits or to the soil in which the plants grow.

DEFINITIONS

The term "alkyl" as used herein in the context of alkyl or alkylsulfonyl, alkylsulfinyl, alkylthio, alkylamino, for example, is to be understood as preferably meaning branched and unbranched alkyl, meaning e.g. methyl, ethyl, n-propyl, iso-propyl, n-butyl, iso-butyl, tert-butyl, sec-butyl, pentyl, iso-pentyl, hexyl, heptyl, octyl, nonyl and decyl and the isomers thereof.

The term "haloalkyl" as used herein is to be understood as preferably meaning branched and unbranched alkyl, as defined supra, in which one or more of the hydrogen substituents is replaced in the same way or differently with halogen. Particularly preferably, said haloalkyl is, e.g. chloromethyl, fluoropropyl, fluoromethyl, difluoromethyl, trichloromethyl, 2,2,2-trifluoroethyl, pentafluoroethyl, bromobutyl, trifluoromethyl, iodoethyl, and isomers thereof.

The term "alkoxy" as used herein is to be understood as preferably meaning branched and unbranched alkoxy, meaning e.g. methoxy, ethoxy, propyloxy, iso-propyloxy, butyloxy, iso-butyloxy, tert-butyloxy, sec-butyloxy, pentyloxy, iso-pentyloxy, hexyloxy, heptyloxy, octyloxy, nonyloxy, decyloxy, undecyloxy and dodecyloxy and the isomers thereof.

The term "haloalkoxy" as used herein is to be understood as preferably meaning branched and unbranched alkoxy, as defined supra, in which one or more of the hydrogen substituents is replaced in the same way or differently with halogen, e.g. chloromethoxy, fluoromethoxy, pentafluoroethoxy, fluoropropyloxy, difluoromethyloxy, trichloromethoxy, 2,2,2-trifluoroethoxy, bromobutyloxy, trifluoromethoxy, iodoethoxy, and isomers thereof.

The term "carbocyclyl" as used herein refers to a non-aromatic mono- or polycyclic (fused, spiro or bridged) carbon containing ring, which may be saturated or unsaturated, having 3 to 10 ring carbon atoms. Examples of carbocyclyl include cycloalkyl and cycloalkenyl groups. Examples of saturated cycloalkyl include but are not limited to cyclopropyl, cyclobutyl, cyclopentyl, cyclohexyl, cycloheptyl, cyclooctyl, cyclononyl and cyclodecyl group. Examples of unsaturated carbocyclyl group include but are not limited to cyclopropenyl, cyclobutenyl, cyclopentenyl, cyclohexenyl, cycloheptenyl, cyclooctenyl, cyclononenyl, or cyclodecenyl group, wherein the linkage of said cyclolaklyl group to the rest of the molecule can be provided to the double or single bond.

The term "heterocyclyl" as used herein refers to three- to ten-membered, preferably three- to nine-membered, saturated or partially unsaturated heterocycles (including mono-, bi- or tricyclic heterocycles) containing one to four heteroatoms independently selected from the group of oxygen, nitrogen and sulphur. If the ring contains more than one oxygen atom, they are not directly adjacent. Examples of heterocyclyl group include but are not limited to oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3- dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl, indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl. This definition also applies to heterocyclyl as part of a composite substituent, for example heterocyclylalkyl etc., unless defined elsewhere.

The term "halogen" or "Hal" as used herein is to be understood as meaning fluorine, chlorine, bromine or iodine.

The term "alkenyl" as used herein is to be understood as preferably meaning branched and unbranched alkenyl, e.g. a vinyl, propen-1-yl, propen-2-yl, but-1-en-1-yl, but-1-en-2-yl, but-2-en-1-yl, but-2-en-2-yl, but-1-en-3-yl, 2-methyl-prop-2-en-1-yl, or 2-methyl-prop-1-en-1-yl group.

The term "alkynyl" as used herein is to be understood as preferably meaning branched and unbranched alkynyl, e.g. an ethynyl, prop-1-yn-1-yl, but-1-yn-1-yl, but-2-yn-1-yl, or but-3-yn-1-yl group.

The term "aryl" as used herein refers to an aromatic, hydrocarbon, ring system, comprising from 6 to 12 carbon atoms, preferably from 6 to 10 carbon atoms. The ring system may be monocyclic or fused polycyclic (e.g. bicyclic or tricyclic) aromatic ring system. Examples of aryl include but are not limited to phenyl, azulenyl, naphthyl, biphenyl and fluorenyl. It is further understood that when said aryl group is substituted with one or more substituents, said substituent(s) may be at any positions on said aryl ring(s). Particularly, in the case of aryl being a phenyl group, said substituent(s) may occupy one or both ortho positions, one or both meta positions, or the para position, or any combination of these positions. This definition also applies to aryl as part of a composite substituent (e.g. aryloxy).

The term "heteroaryl" as used herein refers to an aromatic ring system containing from 5 to 12 member atoms, of which carbons and one or more heteroatoms which may be identical or different selected from O, N and S. If the ring contains more than one oxygen atom, they are not directly adjacent. Heteroaryl may be monocyclic or polycyclic (e.g. bicyclic or tricyclic). A monocyclic heteroaryl may have 1 to 4 heteroatoms in the ring, while a polycyclic heteroaryl ring may have 1 to 10 heteroatoms. Bicyclic heteroaryl rings may contain from 8 to 12 member atoms (carbon and heteroatoms). Monocyclic heteroaryl may contain from 5 to 8 member atoms. Examples of heteroaryl include but are not limited to thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, e.g., benzofuranyl, benzothienyl, benzoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc. It is further understood that in the case in which said heteroaryl group is substituted with one or more substituents, said substituent(s) may occupy any one or more positions on said heteroaryl ring(s). Particularly, in the case of heteroaryl being a pyridyl group, for example, said substituent(s) may occupy any one or more of positions 2, 3, 4, 5, and/or 6 with respect to the nitrogen atom in the pyridine ring. This definition also applies to heteroaryl as part of a composite substituent (e.g. heteroaryloxy).

As used herein, the term "$C_1$-$C_6$", e.g. in the context of the definition of "$C_1$-$C_6$-alkyl", or "$C_1$-$C_6$-alkoxy", is to be understood as meaning a group having a finite number of carbon atoms of 1 to 6, i.e. 1, 2, 3, 4, 5, or 6 carbon atoms.

As used herein, when a group is said to be "substituted", the group may be substituted with one or more substituents. It is understood that this applies to moieties such as hydrogen, halogen, CN or the like. The expression "one or more substituents" refers to a number of substituents that ranges from one to the maximum number of substituents possible based on the number of available bonding sites, provided that the conditions of stability and chemical feasibility are met.

The term "leaving group" as used herein is to be understood as meaning a group which is displaced from a compound in a substitution or an elimination reaction, for example a halogen atom, a trifluoromethanesulphonate ("triflate") group, alkoxy, methanesulphonate, p-toluenesulphonate, etc.

The term "isomers" as used herein is to be understood as meaning chemical compounds with the same number and types of atoms as another chemical species. There are two main classes of isomers, constitutional isomers and stereoisomers.

The term "constitutional isomers" as used herein is to be understood as meaning chemical compounds with the same number and types of atoms, but they are connected in differing sequences. There are functional isomers, structural isomers, tautomers or valence isomers.

In stereoisomers, the atoms are connected sequentially in the same way, such that condensed formulae for two isomeric molecules are identical. The isomers differ, however, in the way the atoms are arranged in space. There are two major sub-classes of stereoisomers; conformational isomers, which interconvert through rotations around single bonds, and configurational isomers, which are not readily interconvertable.

Configurational isomers are, in turn, comprised of enantiomers and diastereomers. Enantiomers are stereoisomers which are related to each other as mirror images. Enantiomers can contain any number of stereogenic centers, as long as each center is the exact mirror image of the corresponding center in the other molecule. If one or more of these centers differs in configuration, the two molecules are no longer mirror images. Stereoisomers which are not enantiomers are called diastereomers. Diastereomers which still have a different constitution, are another sub-class of diastereomers, the best known of which are simple cis-trans isomers. Clearly, when it is possible for a compound of the present invention to exist in such isomeric forms, the present invention covers single isomers, and any mixture, e.g. racemic mixtures, of such isomers, whether they be isolated or not.

In order to limit different types of isomers from each other reference is made to IUPAC Rules Section E (*Pure Appl Chem* 45, 11-30, 1976).

DETAILED DESCRIPTION

The present invention relates to compounds of the formula (I) or a salt thereof:

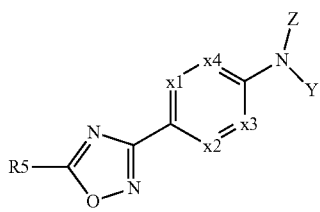

(I)

wherein:
- X1 represents N or CR1;
- X2 represents N or CR2;
- X3 represents N or CR3;
- X4 represents N or CR4;
- wherein R1, R2, R3 and R4, when present, represent independently hydrogen, halogen or $C_1$-$C_3$-alkyl;
- R5 represents $CF_3$ or $CF_2Cl$;
- Z represents aryl, heteroaryl, $C_3$-$C_{10}$-carbocyclyl or 3- to 10-membered-heterocyclyl, wherein said aryl, heteroaryl, $C_3$-$C_{10}$-carbocyclyl or 3- to 10-membered-heterocyclyl, is optionally substituted by one or more substituents which may be the same or different, selected from the group consisting of —$SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy; and
- Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy, provided that Z is not an unsubstituted piperidinyl nor a piperidinyl substituted by a $C_1$-$C_6$-alkoxycarbonyl when X1, X2 and X3 are CH, X4 is N, Y is H and R5 is $CF_3$, or when X1 and X2 are CH, X3 and X4 are N, Y is H and R5 is $CF_3$;

provided that Z is different from $C_3$-$C_{10}$-carbocyclyl when Y is C(=O)—$C_1$-$C_6$-alkyl, —C(=O)—O—$C_1$-$C_6$-alkyl, —C(=S)—$C_1$-$C_6$-alkyl or $C_1$-$C_6$-alkylsulfonyl (each group being substituted or unsubstituted, e.g. $C_1$-$C_6$-haloalkylsulfonyl) and R5 is $CF_3$;

provided Z is not phenyl nor 6-membered heteroaryl when X1 and X2 are CH, X3 is CR3 with R3 is hydrogen or chlorine, X4 is N, Y is hydrogen or $C_1$-$C_6$-alkyl and R5 is $CF_3$.

and provided compounds of formula (I) is not:
Acetamide, 2,2,2-trifluoro-N-[(1R,2S)-2-phenylcyclohexyl]-N-[5-[5-(trifluoromethyl)-1,2,4-oxadiazol-3-yl]-2-pyridinyl] (2170456-65-0);
2-Pyridinamine, N-[(1R,2S)-2-phenylcyclohexyl]-5-[5-(trifluoromethyl)-1,2,4-oxadiazol-3-yl]- (2170451-91-7).

In some embodiments (referred herein as embodiment 1), the present invention relates to compounds of the formula (I) or a salt thereof:

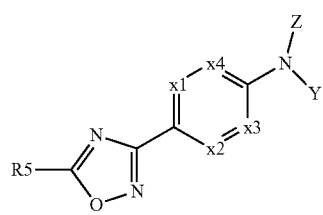

(I)

wherein:
- X1 represents N or CR1;
- X2 represents N or CR2;
- X3 represents N or CR3;
- X4 represents N or CR4;
- wherein R1, R2, R3 and R4, when present, represent independently hydrogen, halogen or $C_1$-$C_3$-alkyl;
- R5 represents $CF_2Cl$;
- Z represents aryl, heteroaryl, $C_3$-$C_{10}$-carbocyclyl or 3- to 10-membered-heterocyclyl, wherein said aryl, heteroaryl, $C_3$-$C_{10}$-carbocyclyl or 3- to 10-membered-heterocyclyl, is optionally substituted by one or more substituents which may be the same or different, selected from the group consisting of —$SF_5$, halogen, cyano, hydroxy, amino, nitro, $C_1$-$C_6$-alkyl, $C_1$-$C_6$-cyanoalkyl, $C_1$-$C_6$ haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-haloalkylthio, $C_3$-$C_{10}$-carbocyclyl, $C_3$-$C_{10}$-halocarbocyclyl, hydroxy-$C_1$-$C_6$-alkyl, $C_1$-$C_6$ alkylamino, di$C_1$-$C_6$ alkylamino, $C_1$-$C_6$ alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-alkyl, $C_1$-$C_6$-alkoxy and $C_1$-$C_6$-haloalkoxy; and Y represents hydrogen, $C_1$-$C_6$-alkyl, $C_1$-$C_6$ haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy.

Non-limiting examples of suitable Z include any of the Z groups disclosed in column "Z" of Table 1. In the above formula (I), Z is preferably substituted by one or more substituents which may be the same or different, selected from the group consisting of halogen, cyano, hydroxy, amino, $C_1$-$C_6$-alkyl, $C_1$-$C_6$-haloalkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl and aminocarbonyl.

In the above formula (I), Y is preferably hydrogen, $C_1$-$C_3$-alkyl and —C(=O)—$C_1$-$C_6$-alkyl.

In the above formula (I), Z is preferably phenyl or 5- or 6-membered heteroaryl.

In some embodiments (referred herein as embodiment 2), compounds according to the invention are compounds of formula (I):

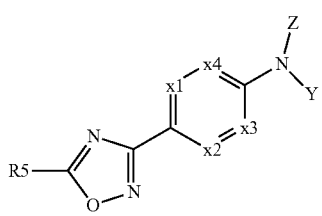

wherein:
X1 represents CR1 wherein R1 represents hydrogen, halogen or $C_1$-$C_3$-alkyl;
X2 represents CR2 wherein R2 represents hydrogen, halogen or $C_1$-$C_3$-alkyl;
X3 represents CR3 wherein R3 represents hydrogen, halogen or $C_1$-$C_3$-alkyl;
X4 represents CR4 wherein R4 represents hydrogen, halogen or $C_1$-$C_3$-alkyl;
R5 represents $CF_2Cl$;
Z represents phenyl or 5- or 6-membered heteroaryl, wherein said phenyl or heteroaryl is optionally substituted by one or more substituents which may be the same or different, selected from the group consisting of —$SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl or heteroaryl is optionally substituted by one or more substituents, which may be the same or different, selected from the group consisting of halogen, $C_1$-$C_6$-alkyl, $C_1$-$C_6$-haloalkyl, cyano, $C_1$-$C_6$-alkoxy and $C_1$-$C_6$-haloalkoxy;

preferably Z is substituted by one or more substituents which may be the same or different, selected from the group consisting of $SF_5$, halogen, cyano, hydroxy, amino, $C_1$-$C_6$-alkyl, $C_1$-$C_6$-haloalkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl; and
Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy, preferably Y represents hydrogen, $C_1$-$C_3$-alkyl and —C(=O)—$C_1$-$C_6$-alkyl.

In some embodiments (referred herein as embodiment 3), compounds according to the invention are compounds of formula (I):

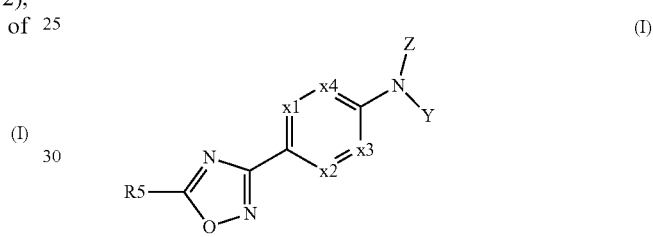

wherein:
X1 represents CR1 wherein R1 represents hydrogen, halogen or $C_1$-$C_3$-alkyl;
X2 represents CR2 wherein R2 represents hydrogen, halogen or $C_1$-$C_3$-alkyl;
X3 represents CR3 wherein R3 represents hydrogen, halogen or $C_1$-$C_3$-alkyl;
X4 represents CR4 wherein R4 represents hydrogen, halogen or $C_1$-$C_3$-alkyl;
R5 represents $CF_3$ or $CF_2Cl$;
Z represents 5- or 6-membered heteroaryl, wherein said heteroaryl is optionally substituted by one or more substituents which may be the same or different, selected from the group consisting of halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl or heteroaryl is optionally substituted by one or more substituents, which may be the same or different, selected from the group consisting of halogen, $C_1$-$C_6$-alkyl, $C_1$-$C_6$-haloalkyl, cyano, $C_1$-$C_6$-alkoxy and $C_1$-$C_6$-haloalkoxy;
preferably Z is substituted by one or more substituents which may be the same or different, selected from the group consisting of $SF_5$, halogen, cyano, hydroxy, amino, $C_1$-$C_6$-alkyl, $C_1$-$C_6$-haloalkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl; and Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3-10-membered-heterocyclyl, aryl (phenyl) or heteroaryl wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy, preferably Y represents hydrogen, $C_1$-$C_3$-alkyl and —C(=O)—$C_1$-$C_6$-alkyl, provided Z is not 6-membered heteroaryl when X1 and X2 are CH, X3 is CR3 with R3 is hydrogen or chlorine, X4 is N, Y is hydrogen or $C_1$-$C_6$-alkyl and R5 is CH.

In some embodiments (referred herein as embodiment 4), compounds according to the invention are compounds of formula (I):

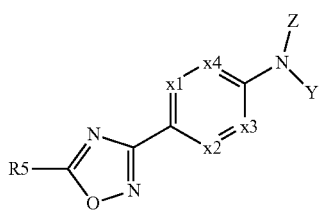

(I)

wherein:
X1 represents N or CR1 wherein R1 represents hydrogen, halogen or $C_1$-$C_3$-alkyl;
X2 represents N or CR2 wherein R2 represents hydrogen, halogen or $C_1$-$C_3$-alkyl;
X3 represents N or CR3 wherein R3 represents hydrogen, halogen or $C_1$-$C_3$-alkyl;
X4 represents N or CR4 wherein R4 represents hydrogen, halogen or $C_1$-$C_3$-alkyl;
R5 represents CH or CF$_2$Cl;
wherein one and only one of X1, X2, X3 and X4 is not N;
Z represents phenyl or 5- or 6-membered heteroaryl, wherein said phenyl or heteroaryl is optionally substituted by one or more substituents which may be the same or different, selected from the group consisting of SF$_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-haloalkyl, $C_1$-$C_6$-alkoxy and $C_1$-$C_6$-haloalkoxy;
preferably Z is substituted by one or more substituents which may be the same or different, selected from the group consisting of SF$_5$, halogen, cyano, hydroxy, amino, $C_1$-$C_6$-alkyl, haloalkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl; and Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl wherein said Y is optionally substituted with halogen, cyano, $C_1$-$C_6$ alkyl, $C_1$-$C_6$-haloalkyl, $C_1$-$C_6$-alkoxy or $C_1$-$C_6$-haloalkoxy, preferably Y represents hydrogen, $C_1$-$C_3$-alkyl and —C(=O)—$C_1$-$C_6$-alkyl.

In some embodiments (referred herein as embodiment 5), compounds according to the invention are compounds of formula (I):

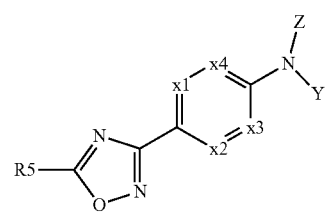

(I)

wherein:
X1 represents N or CR1 wherein R1 represents hydrogen, halogen or $C_1$-$C_3$-alkyl;
X2 represents N or CR2 wherein R2 represents hydrogen, halogen or $C_1$-$C_3$-alkyl;
X3 represents N or CR3 wherein R3 represents hydrogen, halogen or $C_1$-$C_3$-alkyl;
X4 represents N or CR4 wherein R4 represents hydrogen, halogen or $C_1$-$C_3$-alkyl;
R5 represents CF$_3$ or CF$_2$Cl;
wherein one and only one of X1, X2, X3 and X4 is not N;
Z represents 5- or 6-membered heteroaryl, wherein said heteroaryl is optionally substituted by one or more substituents which may be the same or different, selected from the group consisting of SF$_5$, halogen, cyano, hydroxy, amino, nitro, $C_1$-$C_6$-alkyl, $C_1$-$C_6$-cyanoalkyl, $C_1$-$C_6$ haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-haloalkylthio, $C_3$-$C_{10}$-carbocyclyl, $C_3$-$C_{10}$-halocarbocyclyl, hydroxy-$C_1$-$C_6$-alkyl, $C_1$-$C_6$ alkylamino, di$C_1$-$C_6$ alkylamino, $C_1$-$C_6$ alkylcarbonyl, $C_1$-$C_6$-alkoxycarbonyl, aminocarbonyl, aryl (e.g. phenyl), aryl-$C_1$-$C_6$-alkyl and heteroaryl, wherein said heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy;
preferably Z is substituted by one or more substituents which may be the same or different, selected from the group consisting of SF$_5$, halogen, cyano, hydroxy, amino, $C_1$-$C_6$-alkyl, $C_1$-$C_6$-haloalkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl; and Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl wherein said Y is optionally substituted with halogen, cyano, $C_1$-$C_6$ alkyl, $C_1$-$C_6$-haloalkyl, $C_1$-$C_6$-alkoxy or $C_1$-$C_6$-haloalkoxy, preferably Y represents hydrogen, $C_1$-$C_3$-alkyl and —C(=O)—$C_1$-$C_6$-alkyl.

In some embodiments (referred herein as embodiment 6), compounds according to the invention are compounds of formula (I):

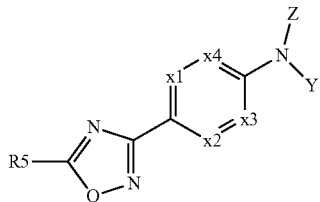

(I)

wherein:
X1 represents N or CH;
X2 represents N or CH;
X3 represents N or CR3 wherein R3 represents hydrogen or fluor;
X4 represents N or CR4 wherein R4 represents hydrogen or fluor;
wherein at least one of X3 and X4 is CF and at least one of X1, X2, X3 and X4 is N and not more than two of X1, X2, X3 and X4 are N;
R5 represents $CF_3$ or $CF_2Cl$;
Z represents phenyl or 5- or 6-membered heteroaryl, wherein said phenyl or heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$ alkylamino, di$C_1$-$C_6$ alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy;
preferably Z is substituted by one or more substituents which may be the same or different, selected from the group consisting of $SF_5$, halogen, cyano, hydroxy, amino, $C_1$-$C_6$-alkyl, $C_1$-$C_6$-haloalkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, di$C_1$-$C_6$-alkylamino, $C_1$-$C_6$-alkyl-C(=O)—NH— and aminocarbonyl; and
Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl wherein said Y is optionally substituted with halogen, $C_1$-$C_6$-alkyl, $C_1$-$C_6$-haloalkyl, $C_1$-$C_6$-alkoxy or $C_1$-$C_6$-haloalkoxy, preferably Y represents hydrogen, $C_1$-$C_3$-alkyl and —C(=O)—$C_1$-$C_6$-alkyl.

In some embodiments (referred herein as embodiment 7), compounds according to the invention are compounds of formula (I):

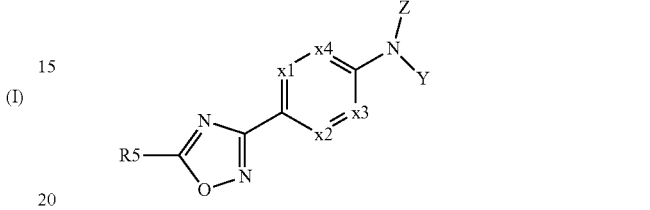

(I)

wherein:
X1 represents N or CR1 wherein R1 represents hydrogen, halogen or $C_1$-$C_3$-alkyl;
X2 represents N or CR2 wherein R2 represents hydrogen, halogen or $C_1$-$C_3$-alkyl;
X3 represents N or CR3 wherein R3 represents hydrogen, halogen or $C_1$-$C_3$-alkyl;
X4 represents N or CR4 wherein R4 represents hydrogen, halogen or $C_1$-$C_3$-alkyl;
R5 represents $CF_3$ or $CF_2Cl$;
wherein at least one of X1, X2, X3 and X4 is N and not more than two of X1, X2, X3 and X4 are N and wherein at least one of X1 and X2 is not N and is not CH;
Z represents phenyl or 5- or 6-membered heteroaryl, wherein said phenyl or heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-haloalkyl, $C_1$-$C_6$-alkoxy and $C_1$-$C_6$-haloalkoxy;
preferably Z is substituted by one or more substituents which may be the same or different, selected from the group consisting of $SF_5$, halogen, cyano, hydroxy, amino, $C_1$-$C_6$-alkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl; and
Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl wherein said Y is optionally substituted with halogen, cyano, $C_1$-$C_6$ alkyl, $C_1$-$C_6$ haloalkyl, $C_1$-$C_6$-alkoxy or $C_1$-$C_6$-haloalkoxy, preferably Y represents hydrogen, $C_1$-$C_3$-alkyl and —C(=O)—$C_1$-$C_6$-alkyl.

In some embodiments (referred herein as embodiment 8), compounds according to the invention are compounds of formula (I):

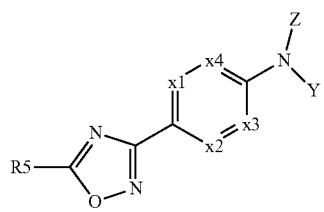

(I)

wherein:
X1 represents N or CR1 wherein R1 represents hydrogen, halogen or $C_1$-$C_3$-alkyl;
X2 represents N or CR2 wherein R2 represents hydrogen, halogen or $C_1$-$C_3$-alkyl;
X3 represents N or CR3 wherein R represents hydrogen, halogen or $C_1$-$C_3$-alkyl;
X4 represents N or CR4 wherein R represents hydrogen, halogen or $C_1$-$C_3$-alkyl;
R5 represents $CF_2Cl$;
preferably wherein at least one of X1, X2, X3 and X4 is N and not more than two of X1, X2, X3 and X4 are N;
Z represents phenyl or 5- or 6-membered heteroaryl, wherein said phenyl or heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, haloalkoxy, $C_1$-$C_6$-alkoxy-$C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$ alkylamino, di$C_1$-$C_6$ alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy;
preferably Z is substituted by one or more substituents which may be the same or different, selected from the group consisting of $SF_5$, halogen, cyano, hydroxy, amino, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl; and
Y represents $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl, wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy, In some embodiments (referred herein as embodiment 9), compounds according to the invention are compounds of formula (I):

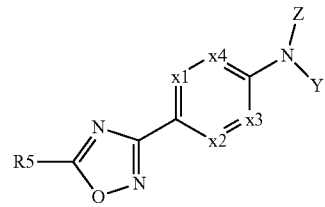

(I)

wherein:
X1 represents N or CR1 wherein R1 represents hydrogen, halogen or $C_1$-$C_3$-alkyl;
X2 represents N or CR2 wherein R2 represents hydrogen, halogen or $C_1$-$C_3$-alkyl;
X3 represents N or CR3 wherein R represents hydrogen, halogen or $C_1$-$C_3$-alkyl;
X4 represents N or CR4 wherein R represents hydrogen, halogen or $C_1$-$C_3$-alkyl;
R5 represents $CF_3$ or $CF_2Cl$;
preferably wherein at least one of X1, X2, X3 and X4 is N and not more than two of X1, X2, X3 and X4 are N;
Z represents 5- or 6-membered heteroaryl, wherein said heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy;
preferably Z is substituted by one or more substituents which may be the same or different, selected from the group consisting of $SF_5$, halogen, cyano, hydroxy, amino, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl; and
Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl, wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy.
provided Z is not 6-membered heteroaryl when X1 and X2 are CH, X3 is CR3 with R3 is hydrogen or chlorine, X4 is N, Y is hydrogen or $C_1$-$C_6$-alkyl and R5 is CH.

In some embodiments (referred herein as embodiment 10), compounds according to the invention are compounds of formula (I):

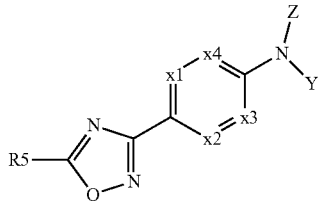
(I)

wherein:
X1 represents N or CR1 wherein R1 represents hydrogen, halogen or $C_1$-$C_3$-alkyl;
X2 represents N or CR2 wherein R2 represents hydrogen, halogen or $C_1$-$C_3$-alkyl;
X3 represents N or CR3 wherein R represents hydrogen, halogen or $C_1$-$C_3$-alkyl;
X4 represents N or CR4 wherein R represents hydrogen, halogen or $C_1$-$C_3$-alkyl;
R5 represents CH or $CF_2Cl$;
preferably wherein at least one of X1, X2, X3 and X4 is N and not more than two of X1, X2, X3 and X4 are N;
Z represents phenyl or 5- or 6-membered heteroaryl, wherein said heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy $C_1$-$C_6$ alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$ alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-haloalkyl, $C_1$-$C_6$-alkoxy and $C_1$-$C_6$-haloalkoxy;
preferably Z is substituted by one or more substituents which may be the same or different, selected from the group consisting of $SF_5$, halogen, cyano, hydroxy, amino, $C_1$-$C_6$-alkyl, $C_2$-$C_6$-alkenyl, $C_2$-$C_6$-alkynyl, $C_1$-$C_6$-alkoxy, hydroxy-$C_1$-$C_6$-alkyl, $C_1$-$C_6$-alkylamino, alkylamino, $C_1$-$C_6$-alkylcarbonyl, $C_1$-$C_6$-alkoxycarbonyl, $C_1$-$C_6$-alkyl-C(=O)—NH— and aminocarbonyl; and
Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl, wherein said Y is optionally substituted with halogen, cyano, $C_1$-$C_6$ alkyl, $C_1$-$C_6$ haloalkyl, $C_1$-$C_6$-alkoxy or $C_1$-$C_6$-haloalkoxy;
provided that X1, X2, X3, X4 and the carbon atoms of the ring do not form a phenyl, pyridyl, pyridinazyl, pyrazinyl ring when Z is phenyl and R5 is $CF_3$.
provided that Z is not 6-membered heteroaryl when X1 and X2 are CH, X3 is CR3 with R3 is hydrogen or chlorine, X4 is N, Y is hydrogen or $C_1$-$C_6$-alkyl and R5 is $CF_3$.

In some embodiments (referred herein as embodiment 11), compounds according to the invention are compounds of formula (I):

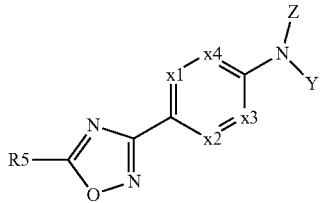
(I)

wherein:
X1 represents N or CR1 wherein R1 represents hydrogen, chloro or $C_1$-$C_3$-alkyl;
X2 represents N or CR2 wherein R2 represents hydrogen, chloro or $C_1$-$C_3$-alkyl;
X3 represents N or CR3 wherein R3 represents hydrogen, halogen or $C_1$-$C_3$-alkyl;
X4 represents N or CR4 wherein R4 represents hydrogen, halogen or $C_1$-$C_3$-alkyl;
preferably wherein at least one of X1, X2, X3 and X4 is N and not more than two of X1, X2, X3 and X4 are N;
R5 represents $CF_3$ or $CF_2Cl$;
Z represents $C_3$-$C_{10}$-carbocyclyl, naphthyl, $C_5$-$C_{10}$-heteroaryl, 3- to 10-membered-heterocyclyl, wherein said Z is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy $C_1$-$C_6$ alkyl, $C_1$-$C_6$-alkylthio, $C_1$-$C_6$-haloalkylthio, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy;
preferably Z is substituted by one or more substituents which may be the same or different, selected from the group consisting of $SF_5$, halogen, cyano, hydroxy, amino, C1-C6-alkyl, C1-C6-haloalkyl, C2-C6-alkenyl C2-C6-alkynyl, C1-C6-alkoxy, hydroxy-C1-C6-alkyl, C1-C6-alkylamino, diC1-C6-alkylamino, C1-C6-alkylcarbonyl, C1-C6-alkoxycarbonyl, C1-C6-alkyl-C(=O)—NH— and aminocarbonyl; and
Y represents hydrogen, $C_1$-$C_6$-alkyl, $C_1$-$C_6$ haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl, wherein said Y is optionally substituted with halogen, cyano, $C_1$-$C_6$-alkyl, $C_1$-$C_6$ haloalkyl, $C_1$-$C_6$-alkoxy or $C_1$-$C_6$-haloalkoxy, preferably Y represents hydrogen, $C_1$-$C_3$-alkyl and —C(=O)—$C_1$-$C_6$-alkyl,
provided that Z is not an unsubstituted piperidinyl nor a piperidinyl substituted by a $C_1$-$C_6$-alkoxycarbonyl when X1, X2 and X3 are CH, X4 is N, Y is H and R5 is $CF_3$, or when X1 and X2 are CH, X3 and X4 are N, Y is H and R5 is $CF_3$; provided that Z is different from $C_3$-$C_{10}$-carbocyclyl when Y is C(=O)—$C_1$-$C_6$-alkyl, alkyl, —C(=S)—$C_1$-$C_6$-alkyl or $C_1$-$C_6$-alkylsulfonyl and R5 is $CF_3$; and provided compounds of formula (I) is not:

Acetamide, 2,2,2-trifluoro-N-[(1R,2S)-2-phenylcyclohexyl]-N-[5-[5-(trifluoromethyl)-1,2,4-oxadiazol-3-yl]-2-pyridinyl] (2170456-65-0);

2-Pyridinamine, N-[(1R,2S)-2-phenylcyclohexyl]-5-[5-(trifluoromethyl)-1,2,4-oxadiazol-3-yl]- (2170451-91-7).

In some embodiments, compounds according to the invention are compounds of formula (I) in accordance with embodiments 1, 2, 4, 6, 7, 8 or 10 wherein Z is phenyl.

In some embodiments, compounds according to the invention are compounds of formula (I) in accordance with embodiments 1, 4, 5, 6, 7, 8, 9 or 10 wherein Z is 5- or 6-membered heteroaryl.

In some embodiments, compounds according to the invention are compounds of formula (I) in accordance with embodiments 3, 4, 5, 6, 7, 8, 9, 10 or 11 wherein R5 is $CF_2Cl$.

In some embodiments, compounds according to the invention are compounds of formula (I) in accordance with embodiments 1, 2, 3, 4, 5, 6, 7, 8, 9, 10 or 11 wherein Y represents —C(=S)—$C_1$-$C_6$-alkyl, $C_1$-$C_6$-haloalkoxy, $C_3$-$C_{10}$-carbocyclyl, 3- to 10-membered-heterocyclyl, aryl (phenyl) or heteroaryl, wherein said Y is optionally substituted with halogen, cyano, $C_1$-$C_6$ alkyl, $C_1$-$C_6$-haloalkyl, $C_1$-$C_6$-alkoxy or $C_1$-$C_6$-haloalkoxy, preferably Y represents hydrogen, $C_1$-$C_3$-alkyl and —C(=O)—$C_1$-$C_6$-alkyl.

In some embodiments, compounds according to the invention are compounds of formula (I) in accordance with embodiments 2, 3, 4, 5, 6, 7 or 8 wherein Z is substituted by one or more substituents which may be the same or different, selected from the group consisting of $SF_5$, halogen, cyano, hydroxy, amino, $C_1$-$C_6$-alkyl, $C_1$-$C_6$-haloalkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl.

In some embodiments, compounds according to the invention are compounds of formula (I) in accordance with embodiments 2, 3, 4, 5, 6, 7 or 8 wherein Y is hydrogen, $C_1$-$C_3$-alkyl or —C(=O)—$C_1$-$C_6$-alkyl.

The present invention relates to any one of the compounds disclosed in Table 1.

In some embodiments, compounds according to the invention are compounds of formula (I):

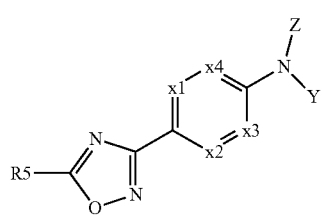

wherein R5 is $CF_2Cl$ and X1, X2, X3, X4, Z and Y are disclosed herein.

Compounds in accordance with embodiments 1, 2, 3, 4, 5 6, 7, 8, 9, 10 and 11 may be used for controlling phytopathogenic fungi. Thus, the present invention relates to the use of a compound of formula (I) in accordance with embodiments 1, 2, 3, 4, 5 6, 7, 8, 9, 10 and 11 for controlling phytopathogenic fungi.

Thus, the present invention also provides for the use of a compound of the formula (I) or a salt thereof for controlling phytopathogenic fungi:

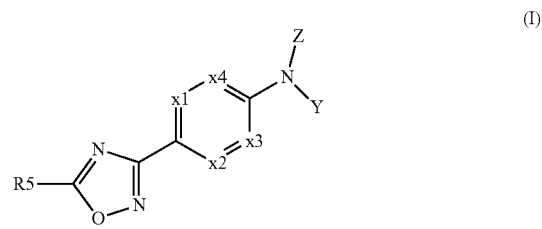

wherein:
X1 represents N or CR1;
X2 represents N or CR2;
X3 represents N or CR3;
X4 represents N or CR4;
wherein R1, R2, R3 and R4, when present, represent independently hydrogen, halogen or $C_1$-$C_3$-alkyl;
R5 $CF_2Cl$;
Z represents $C_3$-$C_{10}$-carbocyclyl, 3- to 10-membered-heterocyclyl, aryl or heteroaryl, wherein said $C_3$-$C_{10}$-carbocyclyl, 3- to 10-membered-heterocyclyl, aryl or heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_3$-$C_{10}$-carbocyclyl, $C_3$-$C_{10}$-halocarbocyclyl, hydroxy-$C_1$-$C_6$-alkyl, $C_1$-$C_6$ alkylamino, di$C_1$-$C_6$ alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy; and Y represents hydrogen, $C_1$-$C_6$-alkyl, $C_1$-$C_6$ haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy, provided that when Y is C(=O)—$C_1$-$C_6$-alkyl, —C(=O)—O—$C_1$-$C_6$-alkyl, —C(=S)—$C_1$-$C_6$-alkyl or $C_1$-$C_6$-alkylsulfonyl, Z is different from $C_3$-$C_{10}$-carbocyclyl.

In some embodiments, the present invention provides for the use of a compound of the formula (I) or a salt thereof for controlling phytopathogenic fungi:

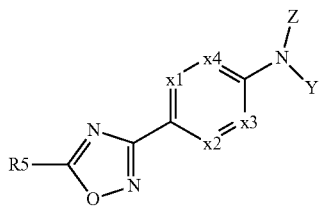 (I)

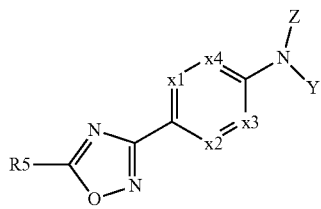 (I)

wherein:

X1 represents CR1 wherein R1 represents hydrogen, halogen or $C_1$-$C_3$-alkyl;

X2 represents CR2 wherein R2 represents hydrogen, halogen or $C_1$-$C_3$-alkyl;

X3 represents CR3 wherein R3 represents hydrogen, halogen or $C_1$-$C_3$-alkyl;

X4 represents CR4 wherein R4 represents hydrogen, halogen or $C_1$-$C_3$-alkyl;

R5 represents $CF_3$ or $CF_2Cl$;

Z represents phenyl or 5- or 6-membered heteroaryl, wherein said phenyl or heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$ alkylamino, di$C_1$-$C_6$ alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-alkyl, $C_1$-$C_6$ haloalkyl, $C_1$-$C_6$-alkoxy and $C_1$-$C_6$-haloalkoxy;

preferably Z is substituted by one or more substituents which may be the same or different, selected from the group consisting of $SF_5$, halogen, cyano, hydroxy, amino, $C_1$-$C_6$-alkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$ alkylamino, di$C_1$-$C_6$ alkylamino, $C_1$-$C_6$-alkylcarbonyl, $C_1$-$C_6$-alkoxycarbonyl, $C_1$-$C_6$-alkyl-C(=O)—NH— and aminocarbonyl; and Y represents hydrogen, $C_1$-$C_6$-alkyl, $C_1$-$C_6$ haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl wherein said Y is optionally substituted with halogen, cyano, $C_1$-$C_6$ alkyl, $C_1$-$C_6$ haloalkyl, $C_1$-$C_6$-alkoxy or $C_1$-$C_6$-haloalkoxy, preferably Y represents hydrogen, $C_1$-$C_3$-alkyl and —C(=O)—$C_1$-$C_6$-alkyl.

In some embodiments, the present invention provides for the use of a compound of the formula (I) or a salt thereof for controlling phytopathogenic fungi:

wherein:

X1 represents N or CR1 wherein R1 represents hydrogen, halogen or $C_1$-$C_3$-alkyl;

X2 represents N or CR2 wherein R2 represents hydrogen, halogen or $C_1$-$C_3$-alkyl;

X3 represents N or CR3 wherein R3 represents hydrogen, halogen or $C_1$-$C_3$-alkyl;

X4 represents N or CR4 wherein R4 represents hydrogen, halogen or $C_1$-$C_3$-alkyl;

R5 represents $CF_3$ or $CF_2Cl$;

wherein one and only one of X1, X2, X3 and X4 is not N;

Z represents phenyl or 5- or 6-membered heteroaryl, wherein said phenyl or heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl (e.g. phenyl), aryl-$C_1$-$C_6$-alkyl and heteroaryl, wherein said aryl (phenyl) or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy;

preferably Z is substituted by one or more substituents which may be the same or different, selected from the group consisting of $SF_5$, halogen, cyano, hydroxy, amino, $C_1$-$C_6$-alkyl, $C_1$-$C_6$-haloalkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl; and Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl (phenyl) or heteroaryl wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy, preferably Y represents hydrogen, $C_1$-$C_3$-alkyl and —C(=O)—$C_1$-$C_6$-alkyl.

In some embodiments, the present invention provides for the use of a compound of the formula (I) or a salt thereof for controlling phytopathogenic fungi:

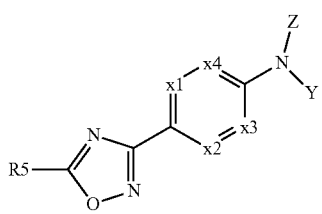

wherein:

X1 represents N or CH;

X2 represents N or CH;

X3 represents N or CR3 wherein R3 represents hydrogen, chloro or $C_1$-$C_3$-alkyl;

X4 represents N or CR4 wherein R4 represents hydrogen, chloro or $C_1$-$C_3$-alkyl;

and wherein at least one of X1, X2, X3 and X4 is N and not more than two of X1, X2, X3 and X4 are N;

R5 is $CF_3$ or $CH_2Cl$;

Z represents phenyl or a 5- or 6-membered heteroaryl, wherein said phenyl or heteroaryl is optionally substituted by one or more substituents which may be the same or different, selected from $SF_5$, cyano, amino, halogen, hydroxyl, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, hydroxy$C_1$-$C_4$-alkyl, $C_1$-$C_4$-alkoxy, $C_1$-$C_4$-alkylamino, di$C_1$-$C_4$-alkylamino, $C_1$-$C_4$-alkylcarbonyl, $C_1$-$C_4$-alkoxycarbonyl, $C_1$-$C_6$-alkyl-C(=O)—NH— and aminocarbonyl; and Y represents hydrogen or $C_1$-$C_3$-alkyl.

The compound of Formula (I) can be in its free form, salt form, N-oxides form or solvate form (e.g. hydrate).

Compositions and Formulations

The present invention further relates to a composition, in particular a composition for controlling unwanted microorganisms, comprising one or more compounds of formula (I). The composition is preferably is a fungicidal composition.

The composition typically comprises one or more compounds of formula (I) and one or more acceptable carriers, in particular one or more agriculturally acceptable carriers.

A carrier is a solid or liquid, natural or synthetic, organic or inorganic substance that is generally inert. The carrier generally improves the application of the compounds, for instance, to plants, plants parts or seeds. Examples of suitable solid carriers include, but are not limited to, ammonium salts, natural rock flours, such as kaolins, clays, talc, chalk, quartz, attapulgite, montmorillonite and diatomaceous earth, and synthetic rock flours, such as finely divided silica, alumina and silicates. Examples of typically useful solid carriers for preparing granules include, but are not limited to crushed and fractionated natural rocks such as calcite, marble, pumice, sepiolite and dolomite, synthetic granules of inorganic and organic flours and granules of organic material such as paper, sawdust, coconut shells, maize cobs and tobacco stalks. Examples of suitable liquid carriers include, but are not limited to, water, organic solvents and combinations thereof. Examples of suitable solvents include polar and nonpolar organic chemical liquids, for example from the classes of aromatic and nonaromatic hydrocarbons (such as cyclohexane, paraffins, alkylbenzenes, xylene, toluene alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as butanol or glycol), ketones (such as acetone, methyl ethyl ketone, methyl isobutyl ketone or cyclohexanone), esters (including fats and oils) and (poly)ethers, unsubstituted and substituted amines, amides (such as dimethylformamide), lactams (such as N-alkylpyrrolidones) and lactones, sulphones and sulphoxides (such as dimethyl sulphoxide). The carrier may also be a liquefied gaseous extender, i.e. liquid which is gaseous at standard temperature and under standard pressure, for example aerosol propellants such as halohydrocarbons, butane, propane, nitrogen and carbon dioxide. The amount of carrier typically ranges from 1 to 99.99%, preferably from 5 to 99.9%, more preferably from 10 to 99.5%, and most preferably from 20 to 99% by weight of the composition.

The composition may further comprise one or more acceptable auxiliaries which are customary for formulating compositions (e.g. agrochemical compositions), such as one or more surfactants.

The surfactant can be an ionic (cationic or anionic) or non-ionic surfactant, such as ionic or non-ionic emulsifier(s), foam former(s), dispersant(s), wetting agent(s) and any mixtures thereof. Examples of suitable surfactants include, but are not limited to, salts of polyacrylic acid, salts of lignosulphonic acid, salts of phenolsulphonic acid or naphthalenesulphonic acid, polycondensates of ethylene and/or propylene oxide with fatty alcohols, fatty acids or fatty amines (polyoxyethylene fatty acid esters, polyoxyethylene fatty alcohol ethers, for example alkylaryl polyglycol ethers), substituted phenols (preferably alkylphenols or arylphenols), salts of sulphosuccinic esters, taurine derivatives (preferably alkyl taurates), phosphoric esters of polyethoxylated alcohols or phenols, fatty esters of polyols and derivatives of compounds containing sulphates, sulphonates, phosphates (for example, alkylsulphonates, alkyl sulphates, arylsulphonates) and protein hydrolysates, lignosulphite waste liquors and methylcellulose. A surfactant is typically used when the compoundof the formula (I) and/or the carrier is insoluble in water and the application is made with water. Then, the amount of surfactants typically ranges from 5 to 40% by weight of the composition.

Further examples of auxiliaries which are customary for formulating agrochemical compositions include water repellents, siccatives, binders (adhesive, tackifier, fixing agent, such as carboxymethylcellulose, natural and synthetic polymers in the form of powders, granules or latices, such as gum arabic, polyvinyl alcohol and polyvinyl acetate, natural phospholipids such as cephalins and lecithins and synthetic phospholipids, polyvinylpyrrolidone, polyvinyl acetate, polyvinyl alcohol and tylose), thickeners, stabilizers (e.g. cold stabilizers, preservatives, antioxidants, light stabilizers, or other agents which improve chemical and/or physical stability), dyes or pigments (such as inorganic pigments, e.g. iron oxide, titanium oxide and Prussian Blue; organic dyes, e.g. alizarin, azo and metal phthalocyanine dyes), antifoams (e.g. silicone antifoams and magnesium stearate), preservatives (e.g. dichlorophene and benzyl alcohol hemiformal), secondary thickeners (cellulose derivatives, acrylic acid derivatives, xanthan, modified clays and finely divided silica), stickers, gibberellins and processing auxiliaries, mineral and vegetable oils, perfumes, waxes, nutrients (including trace nutrients, such as salts of iron, manganese, boron, copper, cobalt, molybdenum and zinc), protective colloids, thixotropic substances, penetrants, sequestering agents and complex formers.

The choice of the auxiliaries is related to the intended mode of application of the compound of the formula (I) and/or on the physical properties. Furthermore, the auxiliaries may be chosen to impart particular properties (technical, physical and/or biological properties) to the compositions or use forms prepared therefrom. The choice of auxiliaries may allow customizing the compositions to specific needs.

The composition of the invention may be in any customary form, such as solutions (e.g aqueous solutions), emulsions, wettable powders, water- and oil-based suspensions, powders, dusts, pastes, soluble powders, soluble granules, granules for broadcasting, suspoemulsion concentrates, natural or synthetic products impregnated with the compoundof the invention, fertilizers and also microencapsulations in polymeric substances. The compound of the invention may be present in a suspended, emulsified or dissolved form.

The composition of the invention may be provided to the end user as ready-for-use formulation, i.e. the compositions may be directly applied to the plants or seeds by a suitable device, such as a spraying or dusting device. Alternatively, the compositions may be provided to the end user in the form of concentrates which have to be diluted, preferably with water, prior to use.

The composition of the invention can be prepared in conventional manners, for example by mixing the compound of the invention with one or more suitable auxiliaries, such as disclosed herein above.

The composition according to the invention contains generally from 0.01 to 99% by weight, from 0.05 to 98% by weight, preferably from 0.1 to 95% by weight, more preferably from 0.5 to 90% by weight, most preferably from 1 to 80% by weight of the compound of the invention.

The compound and the composition of the invention can be mixed with other active ingredients like fungicides, bactericides, acaricides, nematicides, insecticides, herbicides, fertilizers, growth regulators, safeners or semiochemicals. This may allow to broaden the activity spectrum or to prevent development of resistance. Examples of known fungicides, insecticides, acaricides, nematicides and bactericides are disclosed in the Pesticide Manual, 17th Edition.

Examples of especially preferred fungicides which could be mixed with the compound and the composition of the invention are:
1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) Pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl) methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)-ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Mefentrifluconazole, (1.082) Ipfentrifluconazole.

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1 S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1 RS,4SR,9SR), (2.014) isopyrazam (syn-epimeric enantiomer 1R,4S,9R), (2.015) isopyrazam (syn-epimeric enantiomer 1 S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034)N-(2-cyclopentyl-5-fluorobenzyl)-N-cyclopropyl-3-(difluoromethyl)-5-fluoro-1-methyl-1H-pyrazole-4-carboxamide, (2.035)N-(2-tert-butyl-5-methylbenzyl)-N-cyclopropyl-3-(difluoromethyl)-5-fluoro-1-methyl-1H-pyrazole-4-carboxamide, (2.036)N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038)N-(5-chloro-2-isopropylbenzyl)-N-cyclopropyl-3-(difluoromethyl)-5-fluoro-1-methyl-1H-pyrazole-4-carboxamide, (2.039)N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040)N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043)N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045)N-cyclopropyl-3-(difluoromethyl)-5-fluoro-1-methyl-N-[5-methyl-2-(trifluoromethyl)benzyl]-1H-pyrazole-4-carboxamide, (2.046)N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048)N-cyclopropyl-3-(difluoromethyl)-5-fluoro-N-(2-isopropylbenzyl)-1-methyl-1H-pyrazole-4-carbothioamide, (2.049)N-cyclopropyl-3-(difluoromethyl)-5-fluoro-N-(2-isopropylbenzyl)-1-methyl-1H-pyrazole-4-carboxamide, (2.050)N-cyclopropyl-3-(difluoromethyl)-5-fluoro-N-(5-fluoro-2-isopropylbenzyl)-1-methyl-1H-pyrazole-4-carboxamide, (2.051)N-cyclopropyl-3-(difluoromethyl)-N-(2-ethyl-4,5-dimethylbenzyl)-5-fluoro-1-methyl-1H-pyrazole-4-carboxamide, (2.052)N-cyclopropyl-3-(difluoromethyl)-N-(2-ethyl-5-fluorobenzyl)-5-fluoro-1-methyl-1H-pyrazole-4-carboxamide, (2.053)N-cyclopropyl-3-(difluoromethyl)-N-(2-ethyl-5-methylbenzyl)-5-fluoro-1-methyl-1H-pyrazole-4-carboxamide, (2.054)N-cyclopropyl-N-(2-cyclopropyl-5-fluorobenzyl)-3-(difluoromethyl)-5-fluoro-1-methyl-1H-pyrazole-4-carboxamide, (2.055)N-cyclopropyl-N-(2-cyclopropyl-5-methylbenzyl)-3-(difluoromethyl)-5-fluoro-1-methyl-1H-pyrazole-4-carboxamide, (2.056)N-cyclopropyl-N-(2-cyclopropylbenzyl)-3-(difluoromethyl)-5-fluoro-1-methyl-1H-pyrazole-4-carboxamide.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027)N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl) pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluoro-phenyl)-N-(2-chloro-6-fluorophenyl)-1,3-dimethyl-1H-pyrazol-5-amine, (4.016) 4-(2-bromo-4-fluoro-phenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluoro-phenyl)-1,3-dimethyl-1H-pyrazol-5-amine, (4.019) 4-(2-chloro-4-fluorophenyl)-N-(2-chloro-6-fluoro-phenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023)N-(2-bromo-6-fluorophenyl)-4-(2-chloro-4-fluorophenyl)-1,3-dimethyl-1H-pyrazol-5-amine, (4.024)N-(2-bromophenyl)-4-(2-chloro-4-fluorophenyl)-1,3-dimethyl-1H-pyrazol-5-amine, (4.025)N-(4-chloro-2,6-difluorophenyl)-4-(2-chloro-4-fluorophenyl)-1,3-dimethyl-1H-pyrazol-5-amine.

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable to induce a host defence, for example (6.001) acibenzolar-S-methyl, (6.002) isotianil, (6.003) probenazole, (6.004) tiadinil.

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) Inhibitors of the ATP production, for example (8.001) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl) prop-2-en-1-one, (9.009) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.001) propamocarb, (10.002) propamocarb hydrochloride, (10.003) tolclofos-methyl.

11) Inhibitors of the melanin biosynthesis, for example (11.001) tricyclazole, (11.002) 2,2,2-trifluoroethyl {3-methyl-1-[(4-methylbenzoyl)amino]butan-2-yl}carbamate.

12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).

13) Inhibitors of the signal transduction, for example (13.001) fludioxonil, (13.002) iprodione, (13.003) procymidone, (13.004) proquinazid, (13.005) quinoxyfen, (13.006) vinclozolin.

14) Compounds capable to act as an uncoupler, for example (14.001) fluazinam, (14.002) meptyldinocap.

15) Further compounds, for example (15.001) Abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) Oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoro-methyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8- difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one.

All named mixing partners of the classes (1) to (15) as described here above can be present in the form of the free compound and/or, if their functional groups enable this, an agriculturally acceptable salt thereof.

Methods and Uses

The compounds of formula (I) and the compositions of the invention have potent microbicidal activity. They can be used for controlling unwanted microorganisms, such as unwanted fungi and bacteria. They can be particularly useful in crop protection (they control microorganisms that cause plants diseases) or for protecting materials (e.g. industrial materials, timber, storage goods) as described in more details herein below. More specifically, the compounds of formula (I) and the composition of the invention can be used to protect seeds, germinating seeds, emerged seedlings, plants, plant parts, fruits, harvest goods and/or the soil in which the plants grow from unwanted microorganisms.

Control or controlling as used herein encompasses protective, curative and eradicative treatment of unwanted microorganisms. Unwanted microorganisms may be pathogenic bacteria, pathogenic virus, pathogenic oomycetes or pathogenic fungi, more specifically phytopathogenic bacteria phytopathogenic virus, phytopathogenic oomycetes or phytopathogenic fungi. As detailed herein below, these phytopathogenic microorganims are the causal agents of a broad spectrum of plants diseases.

More specifically, the compound of formula (I) and the composition of the invention can be used as fungicides. For the purpose of the specification, the term "fungicide" refers to a compound or composition that can be used in crop protection for the control of unwanted fungi, such as Plasmodiophoromycetes, Chytridiomycetes, Zygomycetes, Ascomycetes, Basidiomycetes and Deuteromycetes and/or for the control of Oomycetes, more preferably Basidiomycetes.

The present invention also relates to a method for controlling unwanted microorganisms, such as unwanted fungi, oomycetes and bacteria, comprising the step of applying at least one compound of formula (I) or at least one composition of the invention to the microorganisms and/or their habitat (to the plants, plant parts, seeds, fruits or to the soil in which the plants grow).

Typically, when the compound and the composition of the invention are used in curative or protective methods for controlling phytopathogenic fungi and/or phytopathogenic oomycetes, an effective and plant-compatible amount thereof is applied to the plants, plant parts, fruits, seeds or to the soil or substrates in which the plants grow. Suitable substrates that may be used for cultivating plants include inorganic based substrates, such as mineral wool, in particular stone wool, perlite, sand or gravel; organic substrates, such as peat, pine bark or sawdust; and petroleum based substrates such as polymeric foams or plastic beads. Effective and plant-compatible amount means an amount that is sufficient to control or destroy the fungi present or liable to appear on the cropland and that does not entail any appreciable symptom of phytotoxicity for said crops. Such an amount can vary within a wide range depending on the fungus to be controlled, the type of crop, the crop growth stage, the climatic conditions and the respective compound or composition of the invention used. This amount can be determined by systematic field trials that are within the capabilities of a person skilled in the art.

Plants and Plant Parts

The compound of formula (I) and the composition of the invention may be applied to any plants or plant parts.

Plants mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the genetically modified plants (GMO or transgenic plants) and the plant cultivars which are protectable and non-protectable by plant breeders' rights.

Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Plants which may be treated in accordance with the methods of the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

In some preferred embodiments, wild plant species and plant cultivars, or those obtained by conventional biological breeding methods, such as crossing or protoplast fusion, and also parts thereof, are treated in accordance with the methods of the invention.

In some other preferred embodiments, transgenic plants and plant cultivars obtained by genetic engineering methods, if appropriate in combination with conventional methods (Genetically Modified Organisms), and parts thereof are treated in accordance with the methods of the invention. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The methods according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plants and plant cultivars which can be treated by the above disclosed methods include all plants which have genetic material which impart particularly advantageous, useful traits to these plants (whether obtained by breeding and/or biotechnological means).

Plants and plant cultivars which can be treated by the above disclosed methods include plants and plant cultivars which are resistant against one or more biotic stresses, i.e. said plants show a better defense against animal and microbial pests, such as against nematodes, insects, mites, phytopathogenic fungi, bacteria, viruses and/or viroids.

Plants and plant cultivars which can be treated by the above disclosed methods include those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which can be treated by the above disclosed methods include those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants and plant cultivars which can be treated by the above disclosed methods include plants and plant cultivars which are hybrid plants that already express the characteristic of heterosis or hybrid vigor which results in generally higher yield, vigor, health and resistance towards biotic and abiotic stresses.

Plants and plant cultivars (obtained by plant biotechnology methods such as genetic engineering) which can be treated by the above disclosed methods include plants and plant cultivars which are herbicide-tolerant plants, i.e. plants made tolerant to one or more given herbicides. Such plants can be obtained either by genetic transformation, or by selection of plants containing a mutation imparting such herbicide tolerance.

Plants and plant cultivars (obtained by plant biotechnology methods such as genetic engineering) which can be treated by the above disclosed methods include plants and plant cultivars which are insect-resistant transgenic plants, i.e. plants made resistant to attack by certain target insects. Such plants can be obtained by genetic transformation, or by selection of plants containing a mutation imparting such insect resistance.

Plants and plant cultivars (obtained by plant biotechnology methods such as genetic engineering) which can be treated by the above disclosed methods include plants and plant cultivars which are tolerant to abiotic stresses. Such plants can be obtained by genetic transformation, or by selection of plants containing a mutation imparting such stress resistance.

Plants and plant cultivars (obtained by plant biotechnology methods such as genetic engineering) which can be treated by the above disclosed methods include plants and plant cultivars which show altered quantity, quality and/or storage-stability of the harvested product and/or altered properties of specific ingredients of the harvested product.

Plants and plant cultivars (obtained by plant biotechnology methods such as genetic engineering) which can be treated by the above disclosed methods include plants and plant cultivars, such as cotton plants, with altered fiber characteristics. Such plants can be obtained by genetic transformation, or by selection of plants contain a mutation imparting such altered fiber characteristics.

Plants and plant cultivars (obtained by plant biotechnology methods such as genetic engineering) which can be treated by the above disclosed methods include plants and plant cultivars, such as oilseed rape or related *Brassica* plants, with altered oil profile characteristics. Such plants can be obtained by genetic transformation, or by selection of plants contain a mutation imparting such altered oil profile characteristics.

Plants and plant cultivars (obtained by plant biotechnology methods such as genetic engineering) which can be treated by the above disclosed methods include plants and plant cultivars, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants and plant cultivars (obtained by plant biotechnology methods such as genetic engineering) which can be treated by the above disclosed methods include plants and plant cultivars, such as Tobacco plants, with altered post-translational protein modification patterns.

Pathogens and Diseases

The methods disclosed above can be used to control microorganisms, in particular phytopathogenic microorganisms such as phytopathogenic fungi, causing diseases, such as:

diseases caused by powdery mildew pathogens, such as *Blumeria* species (e.g. *Blumeria graminis*), *Podosphaera* species (e.g. *Podosphaera leucotricha*), *Sphaerotheca* species (e.g. *Sphaerotheca fuliginea*), *Uncinula* species (e.g. *Uncinula necator*);

diseases caused by rust disease pathogens, such as *Gymnosporangium* species (e.g. *Gymnosporangium sabinae*), *Hemileia* species (e.g. *Hemileia vastatrix*), *Phakopsora* species (e.g. *Phakopsora pachyrhizi* or *Phakopsora meibomiae*), *Puccinia* species (e.g. *Puccinia recondita*, *Puccinia graminis* or *Puccinia striiformis*), *Uromyces* species (e.g. *Uromyces appendiculatus*);

diseases caused by pathogens from the group of the Oomycetes, such as *Albugo* species (e.g. *Albugo candida*), *Bremia* species (e.g. *Bremia lactucae*), *Peronospora* species (e.g. *Peronospora pisi* or *P. brassicae*), *Phytophthora* species (e.g. *Phytophthora infestans*), *Plasmopara* species (e.g. *Plasmopara viticola*), *Pseudoperonospora* species (e.g. *Pseudoperonospora humuli* or *Pseudoperonospora cubensis*), *Pythium* species (e.g. *Pythium ultimum*);

leaf blotch diseases and leaf wilt diseases caused, for example, by *Alternaria* species (e.g. *Alternaria solani*), *Cercospora* species (e.g. *Cercospora beticola*), *Cladiosporium* species (e.g. *Cladiosporium cucumerinum*), *Cochliobolus* species (e.g. *Cochliobolus sativus* (conidial form: Drechslera, syn: Helminthosporium) or *Cochliobolus miyabeanus*), *Colletotrichum* species (e.g. *Colletotrichum lindemuthanium*), *Cycloconium* species (e.g. *Cycloconium oleaginum*), *Diaporthe* species (e.g. *Diaporthe citri*), *Elsinoe* species (e.g. *Elsinoe fawcettii*), *Gloeosporium* species (e.g. *Gloeosporium laeticolor*), *Glomerella* species (e.g. *Glomerella cingulate*), *Guignardia* species (e.g. *Guignardia bidwelli*), *Leptosphaeria* species (e.g. *Leptosphaeria maculans*), *Magnaporthe* species (e.g. *Magnaporthe grisea*), *Microdochium* species (e.g. *Microdochium nivale*), *Mycosphaerella* species (e.g. *Mycosphaerella graminicola*, *Mycosphaerella arachidicola* or *Mycosphaerella fijiensis*), *Phaeosphaeria* species (e.g. *Phaeosphaeria nodorum*), *Pyrenophora* species (e.g. *Pyrenophora teres* or *Pyrenophora tritici repentis*), *Ramularia* species (e.g. *Ramularia collo-cygni* or *Ramularia areola*), *Rhynchosporium* species (e.g. *Rhynchosporium secalis*), *Septoria* species (e.g. *Septoria apii* or *Septoria lycopersici*), *Stagonospora* species (e.g. *Stagonospora nodorum*), *Typhula* species (e.g. *Typhula incarnate*), *Venturia* species (e.g. *Venturia inaequalis*), root and stem diseases caused, for example, by *Corticium* species (e.g. *Corticium graminearum*), *Fusarium* species (e.g. *Fusarium oxysporum*), *Gaeumannomyces* species, (e.g. *Gaeumannomyces graminis*), *Plasmodiophora* species, (e.g. *Plasmodiophora brassicae*), *Rhizoctonia* species, (e.g. *Rhizoctonia solani*), *Sarocladium* species, (e.g. *Sarocladium oryzae*), *Sclerotium* species, (e.g. *Sclerotium oryzae*), *Tapesia* species, (e.g. *Tapesia acuformis*), *Thielaviopsis* species, (e.g. *Thielaviopsis basicola*);

ear and panicle diseases (including corn cobs) caused, for example, by *Alternaria* species, (e.g. *Alternaria* spp.), *Aspergillus* species (e.g. *Aspergillus flavus*), *Cladosporium* species (e.g. *Cladosporium cladosporioides*, *Claviceps* species (e.g. *Claviceps purpurea*), *Fusarium* species, (e.g. *Fusarium culmorum*), *Gibberella* species (e.g. *Gibberella zeae*), *Monographella* species, (e.g. *Monographella nivalis*), *Stagnospora* species, (e.g. *Stagnospora nodorum*);

diseases caused by smut fungi, for example *Sphacelotheca* species (e.g. *Sphacelotheca reiliana*), *Tilletia* species (e.g. *Tilletia caries* or *Tilletia controversa*), *Urocystis* species (e.g. *Urocystis occulta*), *Ustilago* species (e.g. *Ustilago nuda*);

fruit rot caused, for example, by *Aspergillus* species (e.g. *Aspergillus flavus*), *Botrytis* species (e.g. *Botrytis cinerea*), *Penicillium* species (e.g. *Penicillium expansum* or *Penicillium purpurogenum*), *Rhizopus* species (e.g. *Rhizopus stolonifer*), *Sclerotinia* species (e.g. *Sclerotinia sclerotiorum*), *Verticilium* species (e.g. *Verticilium alboatrum*);

seed- and soil-borne rot and wilt diseases, and also diseases of seedlings, caused, for example, by *Alternaria* species (e.g. *Alternaria brassicicola*), *Aphanomyces* species (e.g. *Aphanomyces euteiches*), *Ascochyta* species (e.g. *Ascochyta lentis*), *Aspergillus* species (e.g. *Aspergillus flavus*), *Cladosporium* species (e.g. *Cladosporium herbarum*), *Cochliobolus* species (e.g. *Cochliobolus sativus* (conidial form: *Drechslera, Bipolaris* Syn: *Helminthosporium*)), *Colletotrichum* species (e.g. *Colletotrichum coccodes*), *Fusarium* species (e.g. *Fusarium culmorum*), *Gibberella* species (e.g. *Gibberella zeae*), *Macrophomina* species (e.g. *Macrophomina phaseolina*), *Microdochium* species (e.g. *Microdochium nivale*), *Monographella* species (e.g. *Monographella nivalis*), *Penicillium* species (e.g. *Penicillium expansum*), *Phoma* species (e.g. *Phoma lingam*), *Phomopsis* species (e.g. *Phomopsis sojae*), *Phytophthora* species (e.g. *Phytophthora cactorum*), *Pyrenophora* species (e.g. *Pyrenophora graminea*), *Pyricularia* species (e.g. *Pyricularia oryzae*), *Pythium* species (e.g. *Pythium ultimum*), *Rhizoctonia* species (e.g. *Rhizoctonia solani*), *Rhizopus* species (e.g. *Rhizopus oryzae*), *Sclerotium* species (e.g. *Sclerotium rolfsii*), *Septoria* species (e.g. *Septoria nodorum*), *Typhula* species (e.g. *Typhula incarnate*), *Verticillium* species (e.g. *Verticillium dahlia*);

cancers, galls and witches' broom caused, for example, by *Nectria* species (e.g. *Nectria galligena*); wilt diseases caused, for example, by *Monilinia* species (e.g. *Monilinia laxa*);

deformations of leaves, flowers and fruits caused, for example, by *Exobasidium* species (e.g. *Exobasidium vexans*), *Taphrina* species (e.g. *Taphrina deformans*);

degenerative diseases in woody plants, caused, for example, by *Esca* species (e.g. *Phaeomoniella chlamydospora*, *Phaeoacremonium aleophilum* or *Fomitiporia mediterranea*), *Ganoderma* species (e.g. *Ganoderma boninense*);

diseases of flowers and seeds caused, for example, by *Botrytis* species (e.g. *Botrytis cinerea*); diseases of plant tubers caused, for example, by *Rhizoctonia* species (e.g. *Rhizoctonia solani*), *Helminthosporium* species (e.g. *Helminthosporium solani*);

diseases caused by bacterial pathogens, for example *Xanthomonas* species (e.g. *Xanthomonas campestris* pv. *Oryzae*), *Pseudomonas* species (e.g. *Pseudomonas syringae* pv. *Lachrymans*), *Erwinia* species (e.g. *Erwinia amylovora*).

Seed Treatment

The method for controlling unwanted microorganisms may be used to protect seeds from phytopathogenic microorganisms, such as fungi.

The term "seed(s)" as used herein include dormant seed, primed seed, pregerminated seed and seed with emerged roots and leaves.

Thus, the present invention also relates to a method for protecting seeds and/or crops from unwanted microorganisms, such as bacteria or fungi, which comprises the step of treating the seeds with one or more compounds of formula (I) or a composition comprising thereof. The treatment of seeds with the compound(s) of formula (I) or a composition comprising thereof not only protects the seeds from phytopathogenic microorganisms, but also the germinating plants, the emerged seedlings and the plants after emergence.

The seeds treatment may be performed prior to sowing, at the time of sowing or shortly thereafter. When the seeds treatment is performed prior to sowing (e.g. so-called on-seed applications), the seeds treatment may be performed as follows: the seeds may be placed into a mixer with a desired amount of compound(s) of formula (I) or a composition comprising thereof (either as such or after dilution), the seeds and the compound(s) of formula (I) or the composition comprising thereof are mixed until a homogeneous distribution on seeds is achieved. If appropriate, the seeds may then be dried.

The invention also relates to seeds treated with one or more compounds of formula (I) or a composition comprising thereof. As said before, the use of treated seeds allows not only protecting the seeds before and after sowing from unwanted microorganisms, such as phytopathogenic fungi, but also allows protecting the germinating plants and young seedlings emerging from said treated seeds. A large part of the damage to crop plants caused by harmful organisms is triggered by the infection of the seeds before sowing or after germination of the plant. This phase is particularly critical since the roots and shoots of the growing plant are particularly sensitive, and even small damage may result in the death of the plant.

Therefore, the present invention also relates to a method for protecting seeds, germinating plants and emerged seedlings, more generally to a method for protecting crop from phytopathogenic microorganisms, which comprises the step of using seeds treated by one or more compounds of formula (I) or a composition comprising thereof.

Preferably, the seed is treated in a state in which it is sufficiently stable for no damage to occur in the course of treatment. In general, seeds can be treated at any time between harvest and shortly after sowing. It is customary to use seeds which have been separated from the plant and freed from cobs, shells, stalks, coats, hairs or the flesh of the fruits. For example, it is possible to use seeds which have been harvested, cleaned and dried down to a moisture content of less than 15% by weight. Alternatively, it is also possible to use seeds which, after drying, for example, have been treated with water and then dried again, or seeds just after priming, or seeds stored in primed conditions or pregerminated seeds, or seeds sown on nursery trays, tapes or paper.

The amount of compound(s) of formula (I) or composition comprising thereof applied to the seed is typically such that the germination of the seed is not impaired, or that the resulting plant is not damaged. This must be ensured particularly in case the active ingredients would exhibit phytotoxic effects at certain application rates. The intrinsic phenotypes of transgenic plants should also be taken into consideration when determining the amount of compound(s) of formula (I) or composition comprising thereof to be applied to the seed in order to achieve optimum seed and germinating plant protection with a minimum amount of compound(s) of formula (I) or composition comprising thereof being employed.

As indicated above, the compounds of the formula (I) can be applied, as such, directly to the seeds, i.e. without the use of any other components and without having been diluted, or a composition comprising the compounds of formula (I) can be applied. Preferably, the compositions are applied to the seed in any suitable form. Examples of suitable formulations include solutions, emulsions, suspensions, powders, foams, slurries or combined with other coating compositions for seed, such as film forming materials, pelleting materials, fine iron or other metal powders, granules, coating material for inactivated seeds, and also ULV formulations. The formulations may be ready-to-use formulations or may be concentrates that need to be diluted prior to use.

These formulations are prepared in a known manner, for instance by mixing the active ingredient or mixture thereof with customary additives, for example customary extenders and solvents or diluents, dyes, wetting agents, dispersants, emulsifiers, antifoams, preservatives, secondary thickeners, adhesives, gibberellins, and also water.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1. Useful wetting agents which may be present in the seed dressing formulations are all substances which promote wetting and which are conventionally used for the formulation of active agrochemical ingredients. Usable with preference are alkylnaphthalenesulphonates, such as diisopropyl- or diisobutylnaphthalenesulphonates. Useful dispersants and/or emulsifiers which may be present in the seed dressing formulations are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates. Antifoams which may be present in the seed dressing formulations are all foam-inhibiting substances conventionally used for the formulation of active agrochemical ingredients. Silicone antifoams and magnesium stearate can be used with preference. Preservatives which may be present in the seed dressing formulations are all substances usable for such purposes in agrochemical compositions. Examples include dichlorophene and benzyl alcohol hemiformal. Secondary thickeners which may be present in the seed dressing formulations are all substances usable for such purposes in agrochemical compositions. Preferred examples include cellulose derivatives, acrylic acid derivatives, xanthan, modified clays and finely divided silica. Adhesives which may be present in the seed dressing formulations are all customary binders usable in seed dressing products. Preferred examples include polyvinylpyrrolidone, polyvinyl acetate, polyvinyl alcohol and tylose.

The compounds of the formula (I) and the compositions comprising thereof are suitable for protecting seeds of any plant variety which is used in agriculture, in greenhouses, in forests or in horticulture. More particularly, the seed is that of cereals (such as wheat, barley, rye, millet, triticale, and oats), oilseed rape, maize, cotton, soybean, rice, potatoes, sunflower, beans, coffee, peas, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

The compounds of formula (I) or the compositions comprising thereof can be used for treating transgenic seeds, in particular seeds of plants capable of expressing a protein which acts against pests, herbicidal damage or abiotic stress, thereby increasing the protective effect. Synergistic effects may also occur in interaction with the substances formed by expression.

Application

The compound of the invention can be applied as such, or for example in the form of as ready-to-use solutions, emulsions, water- or oil-based suspensions, powders, wettable powders, pastes, soluble powders, dusts, soluble granules, granules for broadcasting, suspoemulsion concentrates, natural products impregnated with the compound of the invention, synthetic substances impregnated with the compound of the invention, fertilizers or microencapsulations in polymeric substances.

Application is accomplished in a customary manner, for example by watering, spraying, atomizing, broadcasting, dusting, foaming, spreading-on and the like. It is also possible to deploy the compound of the invention by the ultra-low volume method, via a drip irrigation system or drench application, to apply it in-furrow or to inject it into the soil stem or trunk. It is further possible to apply the compound of the invention by means of a wound seal, paint or other wound dressing.

The effective and plant-compatible amount of the compound of the invention which is applied to the plants, plant parts, fruits, seeds or soil will depend on various factors, such as the compound/composition employed, the subject of the treatment (plant, plant part, fruit, seed or soil), the type of treatment (dusting, spraying, seed dressing), the purpose of the treatment (curative and protective), the type of microorganisms, the development stage of the microorganisms, the sensitivity of the microorganisms, the crop growth stage and the environmental conditions.

When the compound of the invention is used as a fungicide, the application rates can vary within a relatively wide range, depending on the kind of application. For the treatment of plant parts, such as leaves, the application rate may range from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used). For the treatment of seeds, the application rate may range from 0.1 to 200 g per 100 kg of seeds, preferably from 1 to 150 g per 100 kg of seeds, more preferably from 2.5 to 25 g per 100 kg of seeds, even more preferably from 2.5 to 12.5 g per 100 kg of seeds. For the treatment of soil, the application rate may range from 0.1 to 10 000 g/ha, preferably from 1 to 5000 g/ha.

These application rates are merely examples and are not intended to limit the scope of the present invention.

Material Protection

The compound and the composition of the invention may also be used in the protection of materials, especially for the protection of industrial materials against attack and destruction by unwanted microorganisms.

In addition, the compound and the composition of the invention may be used as antifouling compositions, alone or in combinations with other active ingredients.

Industrial materials in the present context are understood to mean inanimate materials which have been prepared for use in industry. For example, industrial materials which are to be protected from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compound and the composition of the invention may prevent adverse effects, such as rotting, decay, discoloration, decoloration or formation of mould.

In the case of treatment of wood the compound and the composition of the invention may also be used against fungal diseases liable to grow on or inside timber.

Timber means all types of species of wood, and all types of working of this wood intended for construction, for example solid wood, high-density wood, laminated wood, and plywood. In addition, the compound and the composition of the invention may be used to protect objects which come into contact with saltwater or brackish water, especially hulls, screens, nets, buildings, moorings and signalling systems, from fouling.

The compound and the composition of the invention may also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, may be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The compound and the composition of the invention may prevent adverse effects, such as rotting, decay, discoloration, decoloration or formation of mould.

Microorganisms capable of degrading or altering industrial materials include, for example, bacteria, fungi, yeasts, algae and slime organisms. The compound and the composition of the invention preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*, *Chaetomium*, such as *Chaetomium globosum*; *Coniophora*, such as *Coniophora puetana*; *Lentinus*, such as *Lentinus tigrinus*; *Penicillium*, such as *Penicillium glaucum*; Polyporus, such as *Polyporus versicolor*, *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

General Synthetic Routes to the Compounds of General Formula I

The present invention also relates to processes for the preparation of compounds of formula (I). Unless indicated otherwise, the radicals X1, X2, X3, X4, R1, R2, R3, R4, R5, Z and Y have the meanings given above for the compounds of formula (I). These definitions apply not only to the end products of the formula (I) but likewise to all intermediates.

Compounds of formula (I) can be prepared, according to process P1, by reacting amidoximes of formula (II) with haloalkylacetic anhydride or haloalkylacetyl chloride in a suitable solvent such as tetrahydrofurane or dichloromethane optionally in presence of a base such as trimethylamine or pyridine, preferably at room temperature, as previously described in WO2013080120.

Process P1

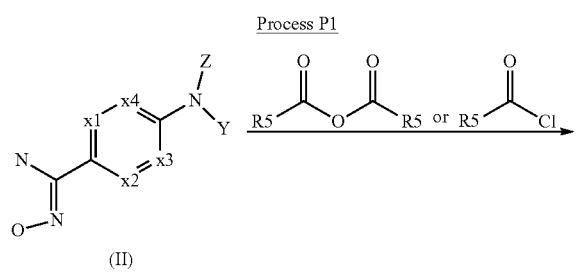

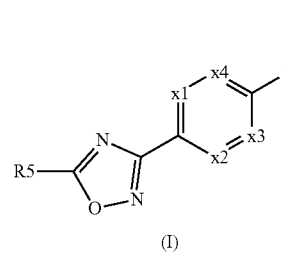

Amidoximes of formula (II) can be prepared according to known procedures (see for examples WO2013080120), as shown in process P2 by treating nitriles of formula (III) with hydroxylamine (or its hydrochloride salt) in the presence of a base such as trimethylamine in a solvent such as ethanol.

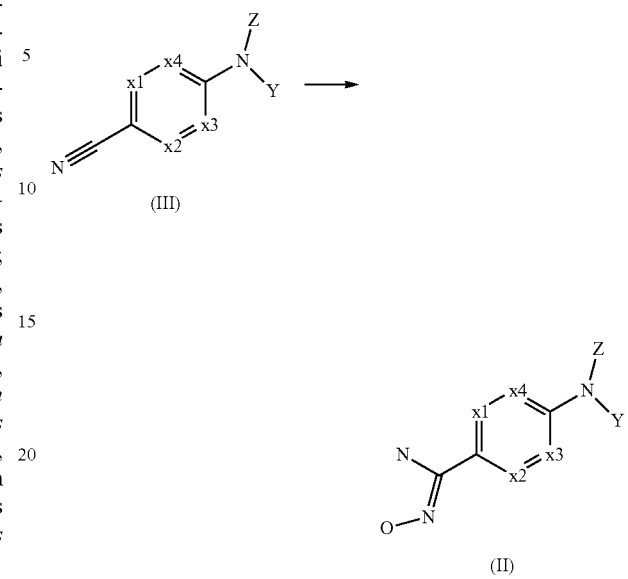

Compounds of formula (III) can be commercially available or may be prepared starting from readily available compounds according to known procedures.

Alternatively compounds of formula (III) can be prepared, according to process P3, from compounds of formula (IV), wherein LG1 is a leaving group as for example bromide with a suitable cyanide reagent such as for example zinc cyanide in presence of palladium (0) in a solvent such as N,N-dimethylformamide as described for example in ACS Medicinal Chemistry Letters, 8(9), 919-924, 2017.

Process P3

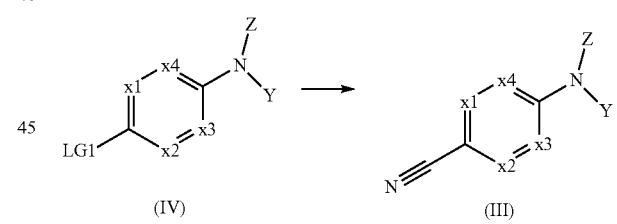

Compounds of formula (IV) can be commercially available or may be prepared starting from readily available compounds according to known procedures.

Alternatively compounds of formula (I) can be prepared, according to process P4, from a compound of formula (V), wherein LG2 is a leaving group by nucleophilic substitution with a compound of formula (VI) (as described for example in European Journal of Medicinal Chemistry, 135, 531-543; 2017 or Bioorganic & Medicinal Chemistry, 25(17), 4553-4559; 2017) optionally in presence of a base (like for example triethylamine) or an acid (like for example p-toluenesulfonic acid or (1S)-(+)-10-camphorsulfonic acid) in a solvent such as for example dichloromethane or dioxane. It may be necessary to activate the leaving group for example by oxidation with 3-chloroperbenzoic acid when LG2 is SMe.

Process P4

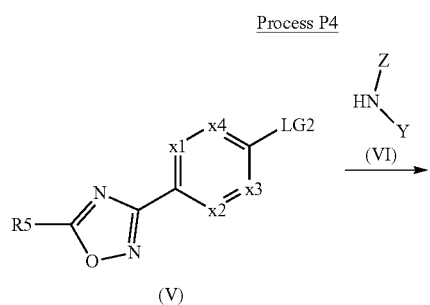

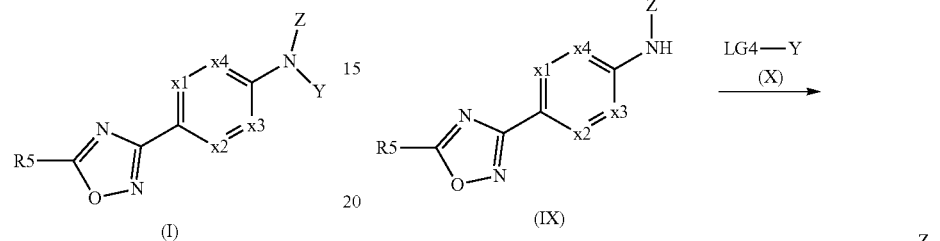

Compounds of formula (V) can be commercially available or may be prepared starting from readily available compounds analogously to process P1 and P2.

Compounds of formula (VI) can be commercially available or may be prepared starting from readily available compounds according to known procedures.

Alternatively compounds of formula (I) can be prepared, according to process P5, from a compound of formula (VII) with a compound of formula (VIII) wherein LG3 is a leaving group such as chlorine by nucleophilic substitution (as described for example in European Journal of Medicinal Chemistry, 135, 531-543; 2017 or Bioorganic & Medicinal Chemistry, 25(17), 4553-4559; 2017) optionally in presence of a base (like for example triethylamine) or an acid (like for example p-toluenesulfonic acid or (1S)-(+)-10-Camphorsulfonic acid) in a solvent such as for example dichloromethane or dioxane.

Process P5

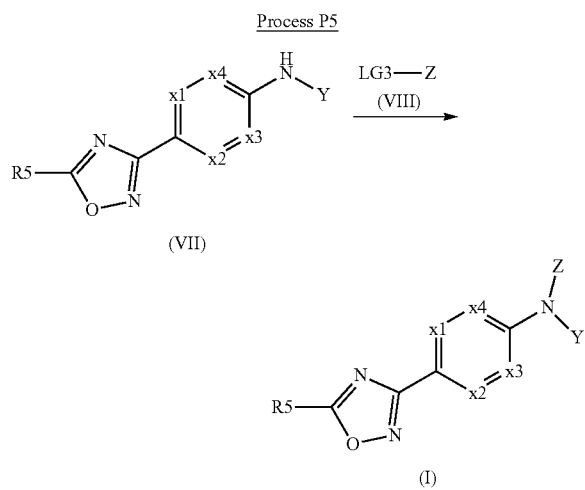

Compounds of formula (VII) can be commercially available or may be prepared starting from readily available compounds analogously to process P1 and P2.

Compounds of formula (VIII) can be commercially available or may be prepared starting from readily available compounds according to known procedures.

Alternatively compounds of formula (I) can be prepared, according to process P6, from a compound of formula (IX) with a compound of formula (X), wherein LG4 is a leaving group, by nucleophilic substitution (as described for example in Medicinal Chemistry Research, 22(11), 5267-5273; 2013 or WO2013080120) optionally in presence of a base (like for example triethylamine), optionally in presence of a solvent such as for example dichloromethane.

Process P6

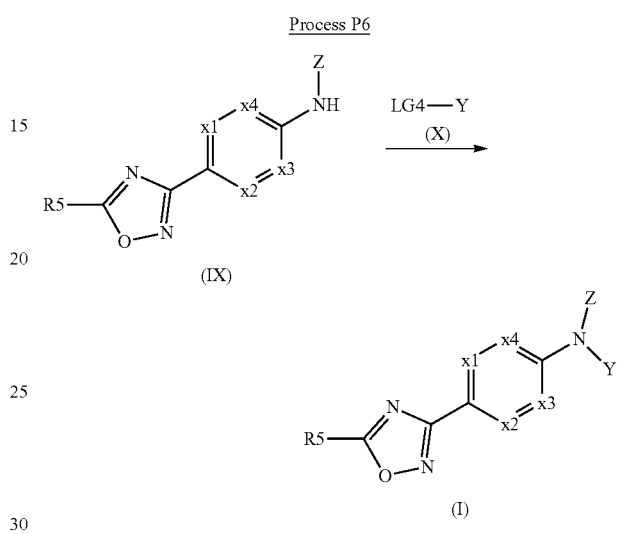

Compounds of formula (IX) can be commercially available or may be prepared starting from readily available compounds analogously to process P1 and P2.

Compounds of formula (X) can be commercially available or may be prepared starting from readily available compounds according to known procedures.

According to the invention, processes P1 to P6 can be performed if appropriate in the presence of a solvent and if appropriate in the presence of a base.

Suitable solvents for carrying out processes P1 to P6 according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N, N-dimethylformamide, N, N-dimethylacetamide, N-methylformanilide, N-methylpyrrolidone or hexamethylphosphoric triamide; esters, such as methyl acetate or ethyl acetate, sulfoxides, such as dimethyl sulfoxide or sulfones, such as sulfolane.

Suitable bases for carrying out processes P1 to P6 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

When carrying out processes P1 to P6, according to the invention, the reaction temperature can independently be varied within a relatively wide range. Generally, processes according to the invention are carried out at temperatures between −20° C. and 160° C.

Processes P1 to P6 according to the invention are generally independently carried out under atmospheric pressure. However, it is also possible to operate under elevated or reduced pressure.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that can still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesized.

Aspects of the present teaching may be further understood in light of the following examples, which should not be construed as limiting the scope of the present teaching in any way.

EXAMPLES

The following examples illustrate in a non-limiting manner the preparation and efficacy of the compounds of formula (I) according to the invention.

Synthesis of Intermediate of Formula (V)

2-(Methylsulfonyl)-5-[5-(trifluoromethyl)-1,2,4-oxadiazol-3-yl]pyrimidine

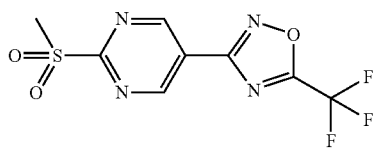 [SMILES: CS(=O)(=O)c1ncc(-c2noc(C(F)(F)F)n2)cn1]

Step 1:

To a mixture of 2-(methylsulfanyl)pyrimidine-5-carbonitrile (25.00 g, 165.35 mmol, 1.00 eq) and hydroxylamine hydrochloride (22.98 g, 330.70 mmol, 2.00 eq) in ethanol (250.00 ml) and water (250.00 ml) was added sodium hydrogen carbonate (27.78 g, 330.70 mmol, 2.00 eq). The reaction was stirred at 70° C. for 16 h. This mixture was filtered and washed with water (50 ml*4). The residue was collected and evaporated. This residue N'-hydroxy-2-(methylsulfanyl)pyrimidine-5-carboximidamide (29.00 g, crude) was used for next step without further purification.

Step 2

A mixture of N'-hydroxy-2-(methylsulfanyl)pyrimidine-5-carboximidamide (16.28 mmol, 1.00 eq) and trifluoroacetic anhydride (24.43 mmol, 1.50 eq) was stirred at 45° C. for 16 h. The mixture was poured into ice and filtered. The residue was washed with water and collected. The product 2-(methylsulfanyl)-5-[5-(trifluoromethyl)-1,2,4-oxadiazol-3-yl]pyrimidine was used for next step without further purification.

Step 3

To a solution of 2-(methylsulfanyl)-5-[5-(trifluoromethyl)-1,2,4-oxadiazol-3-yl]pyrimidine (10.89 mmol, 1.00 eq) in dichloromethane (30.00 ml) was added 3-chloroperbenzoic acid (23.96 mmol, 2.20 eq) with stirring. The mixture was stirred at 25° C. for 16 h. The mixture was diluted with water (100 ml) and quenched with sodium sulfite. The mixture was extracted with dichloromethane (100 ml*3). The organic layer was collected and evaporated. The residue was purified with flash chromatography (ethylacetate:Petroleum ether 3:5). 2-(methylsulfonyl)-5-[5-(trifluoromethyl)-1,2,4-oxadiazol-3-yl]pyrimidine (7.85 mmol) was obtained as a white solid.

Synthesis of compounds of formula (I)

N-[(4R)-3,4-dihydro-2H-chromen-4-yl]-5-[5-(trifluoromethyl)-1,2,4-oxadiazol-3-yl]pyrimidin-2-amine (Compound I-01)

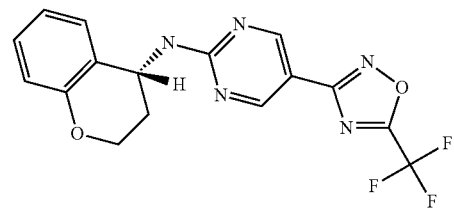 [SMILES: FC(F)(F)c1nc(-c2cnc(N[C@@H]3CCOc4ccccc43)nc2)no1]

To a solution of 2-(methylsulfonyl)-5-[5-(trifluoromethyl)-1,2,4-oxadiazol-3-yl]pyrimidine (1.00 mmol, 1.00 eq) and (4R)-chroman-4-amine (2.00 mmol, 2.00 eq) in dichloromethane (4.00 ml) was added triethylamine (1.00 mmol, 1.0 eq). The reaction mixture was stirred at 50° C. for 16 h. The mixture was concentrated to afford crude product. The residue was purified by prep. HPLC (Acid) to afford N-[(4R)-3,4-dihydro-2H-chromen-4-yl]-5-[5-(trifluoromethyl)-1,2,4-oxadiazol-3-yl]pyrimidin-2-amine.

N-(2-Fluorophenyl)-5-[5-(trifluoromethyl)-1,2,4-oxadiazol-3-yl]pyrimidin-2-amine (Compound I-04)

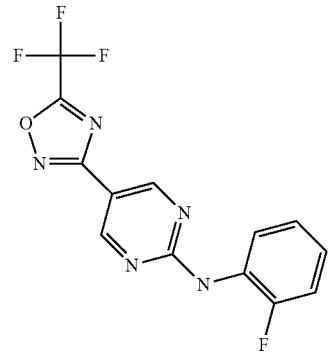 [SMILES: Fc1ccccc1Nc1ncc(-c2noc(C(F)(F)F)n2)cn1]

To a solution of 2-(methylsulfonyl)-5-[5-(trifluoromethyl)-1,2,4-oxadiazol-3-yl]pyrimidine (1.00 mmol, 1.00 eq) and 2-fluoroaniline (2.00 mmol, 2.00 eq.) in dichloromethane (3.00 ml) and N,N-dimethylformamide (3.00 ml) was added (1S)-(+)-10-Camphorsulfonic acid (4.00 mmol, 2.0 eq). The reaction mixture was stirred at 50° C. for 16 h. The mixture was concentrated to afford crude product. The residue was purified by prep. HPLC (Acid) to give N-(2-fluorophenyl)-5-[5-(trifluoromethyl)-1,2,4-oxadiazol-3-yl]pyrimidin-2-amine.

MS (ESI): 326 ([M+H]+)

N-{4-[5-(trifluoromethyl)-1,2,4-oxadiazol-3-yl]phenyl}pyrimidin-2-amine (Compounds I-05)

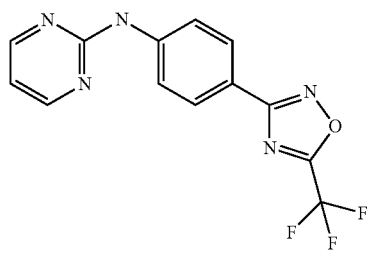 [SMILES: FC(F)(F)c1nc(-c2ccc(Nc3ncccn3)cc2)no1]

To a solution of 4-[5-(trifluoromethyl)-1,2,4-oxadiazol-3-yl]aniline (60 mg, 0.26 mmol) in 2 mL dioxane, was added 2-chloropyrimidine (33 mg, 0.28 mmol) followed by 4-toluenesulfonic acid (10.0 mg, 0.05 mmol). The orange suspension was stirred at 100° C. for 5 h. 2-Chlororpyrimidine (33 mg, 0.28 mmol) was then added and the resulting mixture was stirred at 100° C. for 9 h. Water was added and the aqueous layer was extracted three times with dichloromethane. The organic layers were combined, dried over magnesium sulfate and concentrated under reduced pressure. The residue was purified by flash chromatography (heptane:ethyl acetate 100:0 to 90:10) to afford N-{4-[5-(trifluoromethyl)-1,2,4-oxadiazol-3-yl]phenyl}pyrimidin-2-amine (58 mg, 67% yield) as a pale yellow solid.

MS (ESI): 308 ([M+H]+)

N-(2-fluorophenyl)-N-{5-[5-(trifluoromethyl)-1,2,4-oxadiazol-3-yl]pyrimidin-2-yl}acetamide (Compound I-07)

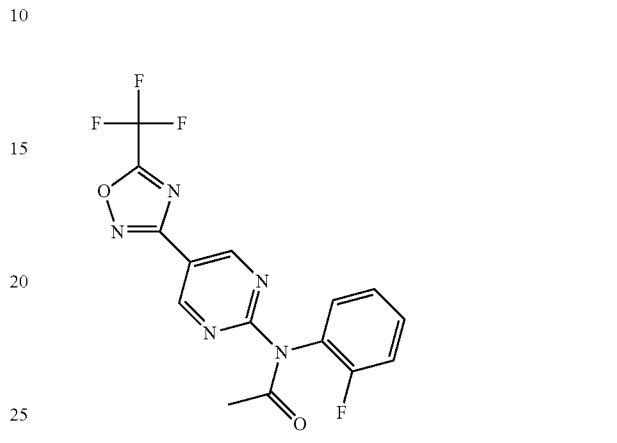

A solution of N-(2-fluorophenyl)-5-[5-(trifluoromethyl)-1,2,4-oxadiazol-3-yl]pyrimidin-2-amine (Compound I-04) (50 mg, 0.15 mmol) in 1 mL acetic acid was refluxed for 5 h and then stirred at RT overnight. The solvent was evaporated under reduced pressure and the residue was purified by flash chromatography to afford N-(2-fluorophenyl)-N-{5-[5-(trifluoromethyl)-1,2,4-oxadiazol-3-yl]pyrimidin-2-yl}acetamide as a colorless oil.

MS (ESI): 368 ([M+H]+)

The compounds in table 1 were prepared in an analogous manner: in analogy with the examples provided above.

TABLE 1

Compounds according to formula (I)

| Ex N° | X1 | X2 | X3 | X4 | Y | Z | R5 | LogP | Stereo chemistry |
|---|---|---|---|---|---|---|---|---|---|
| I-01 | CH | CH | N | N | H | chroman-4-yl | $CF_3$ | | (R) enantiomer |
| I-02 | CH | CH | N | N | H | 1,2,3,4-tetrahydronaphthalen-1-yl | $CF_3$ | | (R) enantiomer |
| I-03 | CH | CH | N | N | H | indan-1-yl | $CF_3$ | | (R) enantiomer |
| I-04 | CH | CH | N | N | H | 2-fluorophenyl | $CF_3$ | | |
| I-05 | CH | CH | CH | CH | H | pyrimidin-2-yl | $CF_3$ | 3.50[a] | |
| I-06 | CH | CH | CH | CH | H | 4-methylpyrimidin-2-yl | $CF_3$ | 3.83[a] | |
| I-07 | CH | CH | N | N | acetyl | 2-fluorophenyl | $CF_3$ | 3.23[a] | |
| I-08 | CH | CH | N | N | H | cyclopentyl | $CF_3$ | 3.83[a] | |
| I-09 | CH | CH | N | N | H | 2-(trifluoromethyl)cyclopropyl | $CF_2Cl$ | 3.65[a] | |
| I-10 | CH | CH | N | N | H | oxolan-3-yl | $CF_3$ | 2.35[a] | |
| I-11 | CH | CH | N | N | H | oxolan-3-yl | $CF_2Cl$ | 2.55[a] | |
| I-12 | CH | CH | N | N | $CH_3$ | cyclopentyl | $CF_2Cl$ | 5.42[a] | |
| I-13 | CH | CH | N | N | H | 1-acetylpiperidin-4-yl | $CF_3$ | 2.17[a] | |

TABLE 1-continued

Compounds according to formula (I)

| Ex N° | X1 | X2 | X3 | X4 | Y | Z | R5 | LogP |
|---|---|---|---|---|---|---|---|---|
| I-14 | CH | CH | N | N | H | 1-methylcyclopropyl | CF$_2$Cl | 3.25[a] |
| I-15 | CH | CH | N | N | H | oxan-4-yl | CF$_2$Cl | 2.76[a] |
| I-16 | CH | CH | N | N | H | oxan-4-yl | CF$_3$ | 2.57[a] |
| I-17 | CH | CH | N | N | H | 1-phenylcyclopropyl | CF$_3$ | 3.74[a] |
| I-18 | CH | CH | N | N | H | 3,3-difluorocyclobutyl | CF$_2$Cl | 3.48[a] |
| I-19 | CH | CH | N | N | H | indan-2-yl | CF$_2$Cl | 4.49[a] |
| I-20 | CH | CH | N | N | H | 1-acetylpiperidin-4-yl | CF$_2$Cl | 2.32[a] |
| I-21 | CH | CH | N | N | H | 2-(trifluoromethyl)cyclopropyl | CF$_3$ | 3.46[a] |
| I-22 | CH | CH | N | N | H | 1,1-dioxothiolan-3-yl | CF$_3$ | 2.15[a] |
| I-23 | CH | CH | N | N | H | 1-pyridin-2-ylcyclobutyl | CF$_3$ | 1.96[a] |
| I-24 | CH | CH | N | N | H | 1-pyridin-2-ylcyclobutyl | CF$_2$Cl | 2.13[a] |
| I-25 | CH | CH | N | N | H | 1-methylcyclopropyl | CF$_3$ | 3.04[a] |
| I-26 | CH | CH | N | N | H | indan-2-yl | CF$_3$ | 4.27[a] |
| I-27 | CH | CH | N | N | H | cyclopropyl | CF$_2$Cl | 2.76[a] |
| I-28 | CH | CH | N | N | H | cyclopentyl | CF$_2$Cl | 4.08[a] |
| I-29 | CH | CH | N | N | H | 1-phenylcyclopropyl | CF$_2$Cl | 3.94[a] |
| I-30 | CH | CH | N | N | H | 1,1-dioxothiolan-3-yl | CF$_2$Cl | 2.32[a] |
| I-31 | CH | CH | N | N | H | cyclopropyl | CF$_3$ | 2.57[a] |
| I-32 | CH | CH | N | N | H | 3,3-difluorocyclobutyl | CF$_3$ | 3.29[a] |
| I-33 | CH | CH | N | N | H | 4,5-dihydro-1,3-thiazol-2-yl | CF$_2$Cl | 1.26[a] |
| I-34 | CH | CH | N | N | H | 4,5-dihydro-1,3-thiazol-2-yl | CF$_3$ | 1.08[a] |
| I-35 | CH | CH | CH | CH | H | 3-methylphenyl | CF$_3$ | 4.93[a] |
| I-36 | CH | CH | CH | CH | H | 3-(trifluoromethyl)phenyl | CF$_3$ | 5.08[a] |
| I-37 | CH | CH | CH | CH | H | phenyl | CF$_3$ | 4.56[a] |
| I-38 | CH | CH | CH | CH | H | 4-chlorophenyl | CF$_3$ | 5.00[a] |
| I-39 | CH | CH | CH | CH | H | 2-(trifluoromethoxy)phenyl | CF$_3$ | 5.11[a] |
| I-40 | CH | CH | CH | CH | H | 4-methylpyrimidin-2-yl | CF$_2$Cl | 2.98[a] |
| I-41 | CH | CH | N | N | H | 2-fluorophenyl | CF$_2$Cl | 3.94[a] |
| I-42 | CH | CH | N | N | H | 2,4-difluorophenyl | CF$_3$ | 3.70[a] |
| I-43 | CH | CH | N | N | H | 4-(difluoromethoxy)phenyl | CF$_3$ | 3.92[a] |
| I-44 | CH | CH | N | N | H | 3-fluorophenyl | CF$_3$ | 3.94[a] |
| I-45 | CH | CH | N | N | H | 3-methoxyphenyl | CF$_3$ | 3.76[a] |
| I-46 | CH | CH | N | N | H | 3-chlorophenyl | CF$_3$ | 4.34[a] |
| I-47 | CH | CH | N | N | H | 2-chlorophenyl | CF$_3$ | 4.20[a] |
| I-48 | CH | CH | N | N | H | 4-(cyanomethyl)phenyl | CF$_3$ | 3.27[a] |
| I-49 | CH | CH | N | N | H | 1,3-benzodioxol-5-yl | CF$_3$ | 3.50[a] |
| I-50 | CH | CH | N | N | H | 3-(acetylamino)phenyl | CF$_3$ | 2.59[a] |
| I-51 | CH | CH | N | N | H | 3-cyanophenyl | CF$_3$ | 3.52[a] |
| I-52 | CH | CH | N | N | H | 3-methoxy-4-methylphenyl | CF$_3$ | 4.30[a] |
| I-53 | CH | CH | N | N | H | 3-(trifluoromethyl)phenyl | CF$_3$ | 4.46[a] |
| I-54 | CH | CH | N | N | H | 2-methoxyphenyl | CF$_3$ | 4.18[a] |
| I-55 | CH | CH | N | N | H | 4-(pentafluoro-λ6-sulfanyl)phenyl | CF$_3$ | 4.80[a] |
| I-56 | CH | CH | N | N | H | 3-methylphenyl | CF$_3$ | 4.13[a] |
| I-57 | CH | CH | N | N | H | 1,2-oxazol-3-yl | CF$_3$ | 2.50[a] |
| I-58 | CH | CH | N | N | H | 3-thienyl | CF$_3$ | 3.70[a] |
| I-59 | CH | CH | N | N | H | 4-methoxyphenyl | CF$_3$ | 3.57[a] |
| I-60 | CH | CH | N | N | H | indan-4-yl | CF$_3$ | 4.44[a] |
| I-61 | CH | CH | N | N | H | phenyl | CF$_3$ | 3.74[a] |
| I-62 | CH | CH | N | N | H | 4-chlorophenyl | CF$_3$ | 4.34[a] |
| I-63 | CH | CH | N | N | H | 4-fluorophenyl | CF$_3$ | 3.79[a] |
| I-64 | CH | CH | N | N | H | 1,2-oxazol-3-yl | CF$_2$Cl | 2.71[a] |
| I-65 | CH | CH | N | N | H | 3-thienyl | CF$_2$Cl | 3.92[a] |
| I-66 | CH | CH | N | N | H | 4-methoxyphenyl | CF$_2$Cl | 3.79[a] |
| I-67 | CH | CH | N | N | H | 4-chlorophenyl | CF$_2$Cl | 4.56[a] |
| I-68 | CH | CH | N | N | H | 3-methylphenyl | CF$_2$Cl | 4.34[a] |
| I-69 | CH | CH | N | N | H | 4-(difluoromethoxy)phenyl | CF$_2$Cl | 4.11[a] |
| I-70 | CH | CH | N | N | H | 1,3-benzodioxol-5-yl | CF$_2$Cl | 3.72[a] |
| I-71 | CH | CH | N | N | H | phenyl | CF$_2$Cl | 3.96[a] |
| I-72 | CH | CH | N | N | H | 4-fluorophenyl | CF$_2$Cl | 3.99[a] |
| I-73 | CH | CH | N | N | H | indan-4-yl | CF$_2$Cl | 4.69[a] |
| I-74 | CH | CH | N | N | H | 3-(acetylamino)phenyl | CF$_2$Cl | 2.75[a] |
| I-75 | CH | CH | N | N | H | 2,4-difluorophenyl | CF$_2$Cl | 3.92[a] |
| I-76 | CH | CH | N | N | H | 3-fluorophenyl | CF$_2$Cl | 4.18[a] |

TABLE 1-continued

Compounds according to formula (I)

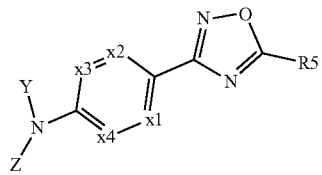

(I)

| Ex N° | X1 | X2 | X3 | X4 | Y | Z | R5 | LogP | Stereo chemistry |
|---|---|---|---|---|---|---|---|---|---|
| I-77 | CH | CH | N | N | H | 2-chlorophenyl | CF$_2$Cl | 4.46[a] | |
| I-78 | CH | CH | N | N | H | 2-methoxyphenyl | CF$_2$Cl | 4.41[a] | |
| I-79 | CH | CH | N | N | H | 3-chlorophenyl | CF$_2$Cl | 4.56[a] | |
| I-80 | CH | CH | N | N | H | 3-methoxyphenyl | CF$_2$Cl | 3.96[a] | |
| I-81 | CH | CH | N | N | H | 3-methoxy-4-methylphenyl | CF$_2$Cl | 4.51[a] | |
| I-82 | CH | CH | N | N | H | 3-cyanophenyl | CF$_2$Cl | 3.72[a] | |
| I-83 | CH | CH | N | N | H | 4-(pentafluoro-λ6-sulfanyl)phenyl | CF$_2$Cl | 5.00[a] | |
| I-84 | CH | CH | N | N | H | 4-(cyanomethyl)phenyl | CF$_2$Cl | 3.46[a] | |
| I-85 | CH | CH | N | N | H | 3-(trifluoromethyl)phenyl | CF$_2$Cl | 4.69[a] | |
| I-86 | CH | CH | N | N | H | 5,6-dihydro-4H-cyclopenta[d][1,3]thiazol-2-yl | CF$_3$ | 3.81[a] | |
| I-87 | CH | CH | N | N | H | quinolin-6-yl | CF$_3$ | 1.98[a] | |
| I-88 | CH | CH | N | N | H | 1-methyl-1H-imidazol-2-yl | CF$_3$ | 1.08[a] | |
| I-89 | CH | CH | N | N | H | 5,6-dihydro-4H-cyclopenta[d][1,3]thiazol-2-yl | CF$_2$Cl | 4.03[a] | |
| I-90 | CH | CH | N | N | H | quinolin-6-yl | CF$_2$Cl | 2.13[a] | |

Measurement of LogP values was performed according to EEC directive 79/831 Annex V.A8 by HPLC (High Performance Liquid Chromatography) on reversed phase columns with the following methods:
[a]LogP value is determined by measurement of LC-UV, in an acidic range, with 0.1% formic acid in water and acetonitrile as eluent (linear gradient from 10% acetonitrile to 95% acetonitrile).
[b]LogP value is determined by measurement of LC-UV, in a neutral range, with 0.001 molar ammonium acetate solution in water and acetonitrile as eluent (linear gradient from 10% acetonitrile to 95% acetonitrile).
[c]LogP value is determined by measurement of LC-UV, in an acidic range, with 0.1% phosphoric acid and acetonitrile as eluent (linear gradient from 10% acetonitrile to 95% acetonitrile).

If more than one LogP value is available within the same method, all the values are given and separated by "+".

Calibration was done with straight-chain alkan2-ones (with 3 to 16 carbon atoms) with known LogP values (measurement of LogP values using retention times with linear interpolation between successive alkanones). Lambda-max-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value signal intensity pairs are semicolons as delimiters.

The peak list of an example has therefore the form:
δ$_1$ (intensity$_1$); δ$_2$ (intensity$_2$); . . . ; δ$_i$ (intensity$_i$); . . . ; δ$_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

I-04: $^1$H-NMR(400.0 MHz, d$_6$-DMSO):
δ = 9.9644(4.6); 8.9946 (16.0); 8.3049 (0.6); 7.6443 (1.1); 7.6409 (1.2); 7.6219 (2.2); 7.6066 (1.3); 7.6012(1.2); 7.3038 (0.7); 7.2837 (2.1); 7.2580 (3.7); 7.2484 (2.2); 7.2430 (2.1); 7.2366 (2.9); 7.2302 (2.0); 7.2179 (2.2); 7.2126 (1.9); 7.2000 (0.8); 7.1950 (0.7); 3.8958 (1.3); 3.3249 (118.6); 2.6728 (0.6); 2.5076 (88.8); 2.5039 (111.7); 2.3306 (0.6); −0.0003 (3.0)

I-05: $^1$H-NMR(300.2 MHz, CDCl3):
δ = 8.5416 (13.5); 8.5255 (13.6); 8.1490(1.1); 8.1410(8.0); 8.1346 (2.8); 8.1182 (3.0); 8.1116 (10.0); 8.1038 (1.3); 7.8904 (1.6); 7.8826 (10.4); 7.8758 (3.0); 7.8595 (2.9); 7.8530 (8.0); 7.8450 (0.9); 7.4198 (2.2); 7.2985 (25.6); 6.8829 (4.1); 6.8668 (7.8); 6.8507 (3.9); 4.1963 (0.9); 4.1725 (2.7); 4.1487 (2.8); 4.1249 (0.9); 2.0834 (12.7); 1.5999 (16.0); 1.3213 (3.4); 1.2975 (6.9); 1.2737 (3.3); 0.1079 (0.4); 0.0488 (1.2); 0.0380 (31.9); 0.0271 (1.1)

I-06: $^1$H-NMR(300.2 MHz, CDCl3):
δ = 8.3896 (2.9); 8.3728 (2.9); 8.1302 (0.5); 8.1224 (3.5); 8.1161 (1.3); 8.0995 (1.4); 8.0930(4.6); 8.0853 (0.7); 7.8938 (0.7); 7.8861 (4.7); 7.8796 (1.5); 7.8629 (1.3); 7.8565 (3.7); 7.8486 (0.5); 7.5074 (1.3); 7.2989 (2.0); 6.7441 (2.4); 6.7273 (2.4); 2.4979 (16.0); 1.7186 (1.2); 1.2924 (0.4); 0.0371 (2.0)

I-07: $^1$H-NMR(300.2 MHz, CDCl3):
δ = 9.2887 (10.0); 7.4751 (0.4); 7.4693 (0.6); 7.4636 (0.6); 7.4543 (0.4); 7.4506 (0.5); 7.4481 (0.5); 7.4405 (0.6); 7.4355 (0.4); 7.4236 (0.4); 7.3281 (1.1); 7.3205 (1.0); 7.3183 (0.9); 7.3126 (2.2); 7.3098 (1.9); 7.2986 (7.6); 7.2905 (2.0); 7.2640(1.2); 7.2604 (1.0); 7.2341 (0.6); 2.6449 (16.0); 1.5877 (6.2); 1.3456 (0.4); 1.3055 (2.3); 0.9421 (0.8); 0.9204 (2.6); 0.8971 (1.0); 0.0384 (5.7)

I-08: $^1$H-NMR(400.2 MHz, d$_6$-DMSO):
δ = 8.8761 (7.9); 8.8280 (8.1); 8.2203 (1.1); 8.1961 (7.0); 8.1778 (7.0); 4.3093 (0.6); 4.2917 (2.5); 4.2747 (4.3); 4.2575 (4.2); 4.2407 (2.4); 4.2274 (0.4); 4.2223 (0.6); 4.0108 (0.4); 3.3279 (65.4); 2.8932 (1.8); 2.7344 (1.5); 2.7332 (1.6); 2.7110 (0.4); 2.6782 (0.5); 2.6737 (0.7); 2.6691 (0.5); 2.5737 (0.4); 2.5272(2.0); 2.5225 (3.0); 2.5138 (43.5); 2.5093 (88.7); 2.5047 (114.9); 2.5001 (79.6); 2.4955 (36.6); 2.3361 (0.5); 2.3315 (0.7); 2.3270 (0.5); 2.1088 (0.5); 1.9521 (2.3); 1.9420 (3.7); 1.9388 (3.7); 1.9306 (6.1); 1.9236 (5.9); 1.9158 (6.4); 1.9085 (4.8); 1.9018 (3.9); 1.8891 (3.0); 1.8812 (1.9); 1.8660 (0.5); 1.7545 (0.5); 1.7451 (1.0); 1.7355 (1.5); 1.7284(2.0); 1.7234 (2.5); 1.7173 (4.0); 1.7004 (9.2); 1.6899 (5.0); 1.6756 (2.3); 1.6680 (2.2); 1.6609 (1.5); 1.6466 (0.8); 1.6362 (0.3); 1.6242 (0.4); 1.6200 (0.5); 1.5952(1.4); 1.5899 (1.4); 1.5725 (5.3); 1.5704 (5.2); 1.5608 (7.3); 1.5536 (10.8); 1.5436 (16.0); 1.5396 (14.7); 1.5345 (10.6); 1.5312(10.0); 1.5244 (7.2); 1.5183 (5.8); 1.5037 (3.8); 1.4901 (1.4); 1.4849 (1.3); 1.2592 (0.5); 1.2370 (2.9); 0.8521 (0.8); 0.0080(0.4); −0.0002 (11.8); −0.0085 (0.3)

I-09: $^1$H-NMR(400.2 MHz, d$_6$-DMSO):
δ = 8.9547 (4.2); 8.9024 (4.1); 8.4770 (10.7); 8.4665 (10.8); 4.0275 (0.3); 4.0109 (0.7); 3.3284 (76.7); 3.3058 (2.5); 3.2930 (4.6); 3.2857 (6.7); 3.2738 (6.9); 3.2652 (5.0); 3.2538 (2.6); 2.8935 (1.8); 2.8930 (1.9); 2.7338 (1.7); 2.7113 (0.6); 2.6941 (0.4); 2.6781 (0.5); 2.6740 (0.8); 2.6695 (0.6); 2.5898 (0.4); 2.5734 (0.6); 2.5548 (0.3); 2.5272 (2.2); 2.5094 (95.1); 2.5050 (126.3); 2.5006 (96.6); 2.3362 (0.6); 2.3319 (0.8); 2.3276 (0.6); 2.1088 (0.5); 2.1002 (0.6); 2.0900 (2.0); 2.0817 (2.5); 2.0713 (3.3); 2.0651 (4.3); 2.0594 (3.7); 2.0560 (3.4); 2.0474(4.6); 2.0406 (3.8); 2.0319 (2.5); 2.0236 (2.3); 2.0132 (0.8); 2.0050 (0.7); 1.2905 (2.3); 1.2747 (10.8); 1.2660 (8.3); 1.2553 (16.0); 1.2393 (14.8); 1.2297 (9.4); 1.2143 (1.8); 0.8683 (0.4); 0.8525 (1.2); 0.8350 (0.5); 0.0078 (0.4); 0.0000 (8.6)

I-10: $^1$H-NMR(400.2 MHz, d$_6$-DMSO):
δ = 8.9014 (9.1); 8.8742 (9.1); 8.5304 (0.5); 8.4078 (8.0); 8.3916 (8.1); 4.5242 (0.9); 4.5136 (2.2); 4.5083 (2.3); 4.5043 (2.6); 4.4979 (4.4); 4.4886 (4.3); 4.4793 (4.6); 4.4729 (2.6); 4.4691 (2.5); 4.4634 (2.3); 4.4530(1.0); 4.0108 (0.4); 3.9055 (8.9); 3.8902 (12.3); 3.8832 (11.2); 3.8684 (16.0); 3.8528 (4.9); 3.7607 (5.0); 3.7467 (5.8); 3.7405 (8.9); 3.7264 (9.0); 3.7201 (4.5); 3.7060(4.0); 3.6159 (9.2); 3.6058 (9.0); 3.5936 (8.0); 3.5834 (7.8); 3.3299 (51.2); 2.8929 (2.0); 2.7331 (1.9); 2.7112(0.4); 2.6782 (0.5); 2.6737 (0.6); 2.6693 (0.5); 2.5741 (0.4); 2.5682 (0.3); 2.5542 (0.7); 2.5401 (0.4); 2.5271 (1.7); 2.5092 (82.6); 2.5047 (108.5); 2.5002 (78.6); 2.3359 (0.5); 2.3315 (0.7); 2.3271 (0.5); 2.2265 (1.9); 2.2072(4.9); 2.1947 (3.0); 2.1890(4.9); 2.1756 (6.3); 2.1701 (2.6); 2.1573 (5.9); 2.1382 (2.4); 2.1331 (4.4); 1.9621 (2.3); 1.9485 (3.2); 1.9437 (3.0); 1.9373 (3.0); 1.9304 (4.8); 1.9188 (4.6); 1.9122 (2.4); 1.9056 (2.4); 1.9009 (2.5); 1.8873 (1.8); 1.2593 (0.6); 1.2371 (3.6); 0.8522 (0.8); 0.8350 (0.4); −0.0003 (7.9)

I-11: $^1$H-NMR(400.2 MHz, d$_6$-DMSO):
δ = 8.8905 (12.2); 8.8641 (12.0); 8.4034 (9.7); 8.3876 (9.4); 8.2675 (0.6); 7.9555 (1.0); 4.5237 (1.5); 4.5128 (3.5); 4.4974 (6.5); 4.4882 (6.2); 4.4821 (5.4); 4.4727 (4.0); 4.4528 (1.3); 4.0123 (0.4); 3.9059 (10.0); 3.8905 (14.2); 3.8836 (12.0); 3.8712 (16.0); 3.8694 (15.9); 3.8523 (11.3); 3.8335 (5.1); 3.8073 (0.4); 3.7613 (5.3); 3.7469 (8.1); 3.7412 (9.1); 3.7270 (9.5); 3.7208 (4.7); 3.7066 (4.0); 3.6152 (9.8); 3.6052 (9.4); 3.5929 (8.7); 3.5830 (7.6); 3.3310 (80.0); 2.8942 (5.3); 2.7350 (5.0); 2.7133 (0.5); 2.6957 (0.4); 2.6790 (0.7); 2.6747 (0.8); 2.5916 (0.5); 2.5741 (0.8); 2.5100 (110.9); 2.5057 (115.9); 2.5016 (78.5); 2.3369 (0.7); 2.3327 (0.8); 2.2266 (2.1); 2.2082 (5.1); 2.1943 (4.9); 2.1895 (5.8); 2.1766 (7.0); 2.1578 (6.4); 2.1384 (2.4); 1.9618 (2.8); 1.9503 (4.6); 1.9478 (4.6); 1.9430 (4.3); 1.9361 (5.1); 1.9318 (5.9); 1.9188 (5.9); 1.9119 (3.5); 1.9051 (3.6); 1.9009 (3.5); 1.8871 (2.0); 1.2987 (0.4); 1.2595 (0.9); 1.2378 (3.2); 0.8524 (0.6); −0.0001 (5.0)

I-12: $^1$H-NMR(400.2 MHz, d$_6$-DMSO):
δ = 8.9048 (11.7); 5.2510 (0.4); 5.2297 (0.6); 5.2095 (0.5); 3.3313 (39.7); 3.0604 (16.0); 2.8923 (0.4); 2.7333 (0.3); 2.7321 (0.3); 2.5261 (0.4); 2.5214 (0.6); 2.5127 (9.8); 2.5082 (20.0); 2.5037 (26.2); 2.4990 (18.4); 2.4945 (8.6); 1.8417 (0.5); 1.8319 (0.6); 1.8279 (0.5); 1.8190 (0.7); 1.8154 (0.6); 1.8114 (0.8); 1.7978 (0.5); 1.7937 (0.4); 1.7534 (0.6); 1.7479 (0.8); 1.7440 (0.9); 1.7388 (0.9); 1.7275 (0.6); 1.7181 (0.5); 1.7091 (0.4); 1.6789 (0.4); 1.6745 (0.4); 1.6595 (0.5); 1.6472 (0.7); 1.6400 (0.8); 1.6324 (0.8); 1.6251 (0.9); 1.6105 (1.4); 1.6047 (1.1); 1.6006 (1.2); 1.5863 (0.6); 1.5754 (0.4); 1.2377 (0.7)

I-13: $^1$H-NMR(400.2 MHz, d$_6$-DMSO):
δ = 8.8932 (1.6); 8.8642 (1.6); 8.2000(1.4); 8.1802 (1.4); 4.3218 (0.6); 4.2889 (0.7); 4.1012(0.4); 4.0939 (0.6); 4.0841 (0.5); 4.0744 (0.6); 4.0667 (0.4); 3.8459 (0.6); 3.8083 (0.7); 3.3324 (23.4); 3.1935 (0.4); 3.1872 (0.6); 3.1582 (0.9); 3.1297 (0.5); 3.1232(0.4); 2.8932 (0.8); 2.7625 (0.4); 2.7558 (0.5); 2.7329 (1.3); 2.6996 (0.5); 2.6934 (0.5); 2.5270 (0.4); 2.5135 (8.9); 2.5092 (17.6); 2.5047 (22.5); 2.5002 (16.6); 2.4959 (8.6); 2.0125 (16.0); 1.9312 (0.6); 1.9180 (0.4); 1.8966 (0.8); 1.8864 (0.7); 1.8773 (0.6); 1.8626 (0.4); 1.8509 (0.7); 1.8453 (0.6); 1.4833 (0.6); 1.4748 (0.6); 1.4539 (0.5); 1.4453 (0.5); 1.3716 (0.5); 1.3625 (0.6); 1.3432 (0.5); 1.3334 (0.6); 1.2386 (0.8); −0.0002 (0.4)

I-14: $^1$H-NMR(400.2 MHz, d$_6$-DMSO):
δ = 8.9394(1.2); 8.8188 (1.2); 8.4119 (2.8); 3.3286 (14.7); 2.5281 (0.4); 2.5235 (0.5); 2.5147 (7.9); 2.5103 (16.6); 2.5057 (22.1); 2.5010 (15.6); 2.4965 (7.4); 1.3932 (16.0); 1.2372 (0.6); 0.7552 (0.9); 0.7479 (0.9); 0.7366 (3.6); 0.7271 (1.8); 0.7151 (0.8); 0.6918 (0.7); 0.6803 (2.2); 0.6704 (3.9); 0.6660 (3.1); 0.6588 (1.0); 0.6515 (1.1); −0.0002(2.2)

I-15: $^1$H-NMR(400.2 MHz, d$_6$-DMSO):
δ = 8.8699 (16.0); 8.8461 (15.9); 8.2425 (0.7); 8.1845 (12.0); 8.1650 (12.0); 7.9542(0.4); 4.0992(1.2); 4.0885 (2.4); 4.0704 (4.3); 4.0611 (5.7); 4.0517 (5.1); 4.0421 (5.8); 4.0330 (4.5); 4.0142 (2.7); 4.0044 (1.3); 3.8970 (13.0); 3.8909 (11.3); 3.8699 (14.4); 3.4512(0.4); 3.4254 (12.8); 3.4006 (21.1); 3.3962 (23.2); 3.3714(11.2); 3.3673 (11.0); 3.3320 (110.6); 2.8943 (2.4); 2.7351 (2.3); 2.7119 (0.7); 2.6953 (0.5); 2.6793 (0.7); 2.6749 (1.0); 2.6705 (0.8); 2.5909 (0.5); 2.5740 (0.8); 2.5546 (0.6); 2.5102 (119.3); 2.5059 (157.3); 2.5018 (125.3); 2.3371 (0.7); 2.3326 (0.9); 2.3284 (0.8); 1.8504 (11.3); 1.8452(11.6); 1.8191 (14.4); 1.8139 (14.3); 1.6073 (4.7); 1.5963 (5.2); 1.5771 (10.6); 1.5676 (11.7); 1.5472 (10.6); 1.5369 (9.8); 1.5183 (4.2); 1.5073 (3.7); 1.2987 (0.6); 1.2896 (0.5); 1.2597 (1.2); 1.2365 (5.6); 0.8684 (0.5); 0.8521 (1.1); 0.8346 (0.5); 0.0076 (0.5); 0.0013 (6.7); −0.0004 (9.1)

I-16: $^1$H-NMR(400.2 MHz, d$_6$-DMSO):
δ = 8.8825 (15.9); 8.8579 (16.0); 8.3160(0.4); 8.2417 (1.7); 8.1900(12.4); 8.1703 (12.5); 8.0746 (0.4); 7.9537 (0.5); 5.8447 (0.4);

4.1001 (1.2); 4.0894 (2.6); 4.0790 (2.7); 4.0709 (4.2); 4.0619 (6.0); 4.0521 (5.2); 4.0426 (6.1); 4.0330 (4.4); 4.0258 (3.0); 4.0150 (2.8); 4.0046 (1.4); 3.9946 (0.5); 3.8967 (12.3); 3.8900 (10.4); 3.8764 (11.7); 3.8702 (13.6); 3.8670 (13.4); 3.4498 (0.4); 3.4293 (11.0); 3.4243 (13.3); 3.4002 (23.2); 3.3950 (23.7); 3.3710(12.4); 3.3659 (10.9); 3.3301 (134.4); 2.8933 (4.1); 2.7334 (3.6); 2.7112 (0.7); 2.6940 (0.4); 2.6827 (0.4); 2.6785 (0.8); 2.6740(1.1); 2.6694 (0.8); 2.5899 (0.4); 2.5739 (0.7); 2.5542 (0.6); 2.5274 (3.5); 2.5226 (5.9); 2.5139 (68.1); 2.5095 (139.4); 2.5050 (183.5); 2.5004 (132.2); 2.4959 (63.9); 2.3363 (0.8); 2.3317 (1.1); 2.3272 (0.8); 1.8505 (10.8); 1.8447(11.0); 1.8190(14.0); 1.8133 (13.7); 1.6078 (5.0); 1.5968 (5.6); 1.5789 (10.6); 1.5677 (11.7); 1.5476 (10.6); 1.5369 (9.6); 1.5186 (4.6); 1.5075 (4.0); 1.4890 (0.3); 1.2985 (0.5); 1.2596 (1.0); 1.2371 (5.4); 0.8688 (0.4); 0.8523 (1.4); 0.8347 (0.5); −0.0002 (5.9)

I-17: $^1$H-NMR(400.2 MHz, d$_6$-DMSO):
δ = 8.9507 (4.4); 8.8974 (1.9); 8.8902 (3.2); 8.8510 (3.1); 8.8438 (1.9); 7.9537 (2.1); 7.2705 (2.1); 7.2663 (0.9); 7.2508 (4.9); 7.2372 (1.5); 7.2327 (4.7); 7.1845 (4.7); 7.1808 (6.8); 7.1755 (1.6); 7.1630 (4.0); 7.1600 (3.3); 7.1544 (1.8); 7.1513 (2.0); 7.1481 (1.1); 7.1377 (1.2); 7.1333 (3.1); 7.1286 (0.8); 7.1187 (0.8); 7.1154 (1.2); 7.1123 (0.6); 3.3304(20.4); 2.8914 (16.0); 2.7334 (13.4); 2.7322 (13.4); 2.5262 (0.5); 2.5215 (0.8); 2.5127 (11.6); 2.5083 (24.3); 2.5037 (32.0); 2.4991 (22.6); 2.4946 (10.7); 1.3471 (0.8); 1.3228 (4.8); 1.3163 (4.4); 1.2907 (4.6); 1.2671 (0.9); 1.2593 (0.5); 1.2383 (1.3); −0.0002 (3.0)

I-18: $^1$H-NMR(400.2 MHz, d$_6$-DMSO):
δ = 8.9068 (16.0); 8.8935 (16.0); 8.6106 (12.1); 8.5944 (12.2); 8.5443 (0.5); 8.2984 (0.3); 7.9532 (0.4); 4.3621 (0.4); 4.3552 (0.4); 4.3421 (1.7); 4.3382 (1.7); 4.3241 (4.2); 4.3064 (5.4); 4.2876 (4.3); 4.2736 (1.8); 4.2697 (1.8); 4.2558 (0.5); 4.2493 (0.4); 4.0272 (0.5); 4.0106 (1.1); 3.9942 (0.5); 3.3278 (127.5); 3.0596 (0.4); 3.0489 (1.3); 3.0433 (1.8); 3.0398 (2.0); 3.0339 (3.6); 3.0287 (4.8); 3.0218 (3.6); 3.0133 (8.0); 3.0068 (5.3); 3.0011 (7.1); 2.9963 (9.1); 2.9922 (7.3); 2.9790 (8.3); 2.9688 (4.3); 2.9644(5.5); 2.9592 (4.3); 2.9541 (2.5); 2.9495 (2.3); 2.9442 (3.6); 2.9343 (0.6); 2.8923 (3.2); 2.7763 (0.6); 2.7663 (3.8); 2.7573 (2.0); 2.7485 (4.0); 2.7432 (2.3); 2.7385 (3.2); 2.7327 (8.4); 2.7228 (6.4); 2.7150 (7.2); 2.7125 (7.0); 2.7053 (6.8); 2.6956 (6.4); 2.6864 (6.4); 2.6783 (6.3); 2.6721 (6.4); 2.6685 (6.0); 2.6626 (3.3); 2.6528 (3.1); 2.6411 (1.7); 2.6350 (3.0); 2.6246 (0.5); 2.5897 (0.8); 2.5729 (1.2); 2.5526 (0.9); 2.5262 (3.7); 2.5126 (76.8); 2.5083 (155.4); 2.5038 (203.0); 2.4993 (145.3); 2.4950 (70.2); 2.3351 (0.9); 2.3307 (1.2); 2.3262 (0.9); 1.5533 (0.4); 1.5353 (0.3); 1.2981 (1.0); 1.2891 (0.6); 1.2591 (1.9); 1.2375 (8.4); 0.8687 (0.7); 0.8523 (2.0); 0.8350 (0.8); 0.0077 (0.5); −0.0003 (15.2); −0.0086 (0.5)

I-19: $^1$H-NMR(400.2 MHz, d$_6$-DMSO):
δ = 8.9226 (5.9); 8.8586 (5.8); 8.4940 (6.5); 8.4767 (6.6); 7.9533 (0.6); 7.2410 (7.9); 7.2324 (9.8); 7.2282 (10.9); 7.2194 (13.4); 7.2106 (3.6); 7.1751 (3.2); 7.1651 (16.0); 7.1570 (10.9); 7.1516 (10.8); 7.1434 (9.8); 4.7687 (0.7); 4.7510 (2.9); 4.7331 (5.6); 4.7152 (5.7); 4.6973 (3.0); 4.6797 (0.7); 4.0099 (0.4); 3.3332 (107.1); 3.3205 (10.6); 3.3013 (8.3); 3.2806 (9.9); 3.2616 (9.4); 2.9767 (9.7); 2.9597 (9.6); 2.9371 (7.7); 2.9202 (7.5); 2.8915 (3.6); 2.7327 (3.3); 2.7101 (0.5); 2.6933 (0.3); 2.6727 (0.6); 2.5887 (0.9); 2.5715 (1.4); 2.5256 (3.8); 2.5080 (69.1); 2.5038 (91.3); 2.4996 (70.2); 2.3304 (0.6); 1.2979 (0.5); 1.2871 (0.4); 1.2579 (1.0); 1.2361 (4.0); 0.8677 (0.3); 0.8514 (0.8); 0.8335 (0.4); −0.0003 (2.0)

I-20: $^1$H-NMR(400.2 MHz, d$_6$-DMSO):
δ = 8.8808 (1.6); 8.8525 (1.6); 8.1940 (1.5); 8.1742 (1.5); 4.3218 (0.7); 4.2885 (0.7); 4.1014(0.4); 4.0930 (0.6); 4.0835 (0.5); 4.0738 (0.6); 4.0654 (0.5); 3.8444 (0.6); 3.8084 (0.7); 3.3321 (25.4); 3.1937 (0.5); 3.1876 (0.6); 3.1587 (1.0); 3.1301 (0.5); 3.1238 (0.5); 2.8932(1.2); 2.7635 (0.4); 2.7574 (0.5); 2.7338 (1.8); 2.7014 (0.6); 2.6947 (0.5); 2.5268 (0.5); 2.5090(21.4); 2.5046 (27.0); 2.5002 (19.6); 2.0122 (16.0); 1.9311 (0.6); 1.8952 (0.8); 1.8853 (0.7); 1.8768 (0.6); 1.8620(0.4); 1.8507 (0.8); 1.4823 (0.6); 1.4737 (0.6); 1.4533 (0.6); 1.4443 (0.6); 1.3712 (0.6); 1.3623 (0.6); 1.3421 (0.6); 1.3329 (0.6); 1.2394 (0.8); −0.0002 (1.8)

I-21: $^1$H-NMR(400.2 MHz, d$_6$-DMSO):
δ = 8.9680 (3.5); 8.9128 (3.5); 8.5702 (0.6); 8.4824 (9.7); 8.4717 (9.8); 7.9536 (0.4); 4.0108 (0.7); 3.3275 (67.6); 3.3064 (2.5); 3.2955 (3.9); 3.2930 (3.9); 3.2869 (6.2); 3.2820 (4.2); 3.2740 (6.2); 3.2668 (4.3); 3.2654 (4.3); 3.2542 (2.6); 2.8933 (3.0); 2.7342 (2.6); 2.7109 (0.6); 2.6944 (0.4); 2.6779 (0.5); 2.6735 (0.8); 2.5898 (0.4); 2.5734 (0.6); 2.5270 (2.3); 2.5222 (3.2); 2.5135 (45.6); 2.5091 (94.7); 2.5045 (124.6); 2.4999 (88.7); 2.4955 (42.2); 2.3360 (0.5); 2.3314 (0.8); 2.3268 (0.5); 2.1097 (0.5); 2.1011 (0.5); 2.0910 (1.8); 2.0827 (2.2); 2.0723 (2.9); 2.0663 (3.7); 2.0605 (3.1); 2.0564 (2.7); 2.0484 (4.0); 2.0425 (3.2); 2.0328 (2.2); 2.0245 (2.0); 2.0143 (0.6); 2.0057 (0.6); 1.2985 (0.5); 1.2904 (2.2); 1.2747 (11.0); 1.2671 (7.5); 1.2553 (16.0); 1.2391 (13.3); 1.2306 (8.8); 1.2150 (1.6); 0.8693 (0.8); 0.8527 (1.2); 0.8351 (0.5); −0.0002 (10.9); −0.0086 (0.4)

I-22: $^1$H-NMR(400.2 MHz, d$_6$-DMSO):
δ = 8.9409 (16.0); 8.5689 (1.6); 8.5438 (10.5); 8.5261 (10.6); 8.3308 (0.7); 8.3155 (0.3); 7.9530 (1.8); 4.7897 (1.0); 4.7708 (3.6); 4.7526 (5.8); 4.7345 (5.9); 4.7162 (3.8); 4.6974 (1.1); 4.0337 (0.4); 4.0274 (0.4); 4.0110 (0.9); 3.9947 (0.4); 3.5859 (7.0); 3.5671 (7.0); 3.5525 (8.1); 3.5336 (7.7); 3.4484(0.3); 3.4365 (2.9); 3.4240 (3.2); 3.4170 (3.4); 3.4038 (7.1); 3.3947 (4.8); 3.3838 (4.8); 3.3713 (4.4); 3.3276 (125.7); 3.2591 (4.5); 3.2394 (6.2); 3.2370 (6.2); 3.2258 (3.6); 3.2169 (5.3); 3.2061 (4.4); 3.2037 (4.6); 3.1838 (3.6); 3.0789 (8.0); 3.0601 (7.8); 3.0457 (7.0); 3.0265 (6.9); 2.8921 (13.6); 2.7331 (11.0); 2.7321 (11.2); 2.7104 (0.8); 2.7031 (0.3); 2.6942 (0.5); 2.6816 (0.4); 2.6771 (0.9); 2.6726 (1.2); 2.6680 (0.9); 2.6635 (0.4); 2.5899 (0.5); 2.5736 (0.8); 2.5539 (0.6); 2.5401 (2.2); 2.5262 (6.6); 2.5214 (7.1); 2.5126 (71.8); 2.5082 (146.9); 2.5038 (187.0); 2.4990 (132.4); 2.4944 (66.3); 2.4781 (4.1); 2.4753 (4.4); 2.4616 (2.1); 2.3394 (0.4); 2.3349 (0.8); 2.3304 (1.1); 2.3258 (0.8); 2.3215 (0.4); 2.2706 (2.7); 2.2490 (5.7); 2.2374 (2.5); 2.2277 (5.7); 2.2157 (4.8); 2.2060 (2.8); 2.1940(4.4); 2.1729 (2.0); 1.2987 (0.6); 1.2891 (0.5); 1.2695 (0.9); 1.2595 (1.4); 1.2390 (7.0); 0.8697 (0.6); 0.8530 (1.8); 0.8356 (0.7); 0.0080 (0.5); −0.0002 (17.3); −0.0084(0.5)

I-23: $^1$H-NMR(400.2 MHz, d$_6$-DMSO):
δ = 9.7646 (1.2); 9.6879 (0.3); 9.0100 (16.0); 8.8956 (6.4); 8.7337 (1.0); 8.6682 (6.3); 8.6161 (0.6); 8.6136 (0.6); 8.6040 (0.6); 8.6019 (0.6); 8.5818 (8.4); 8.5797 (8.9); 8.5774 (8.1); 8.5719 (7.3); 8.5699 (9.0); 8.5677 (8.9); 8.5655 (7.9); 7.9545 (1.6); 7.8117 (0.3); 7.8074 (0.3); 7.6777 (4.4); 7.6732 (4.7); 7.6581 (8.5); 7.6538 (8.6); 7.6391 (5.8); 7.6346 (5.7); 7.3259 (0.4); 7.3061 (12.4); 7.2862(11.4); 7.2158 (6.2); 7.2136 (6.7); 7.2038 (6.3); 7.2015 (7.2); 7.1976 (6.8); 7.1950(6.4); 7.1853 (5.9); 7.1830 (6.1); 7.1514 (0.5); 7.1314(0.4); 4.0346 (0.3); 4.0118 (0.5); 3.4520(0.4); 3.3409 (20.0); 2.9678 (0.5); 2.9511 (0.8); 2.9355 (0.5); 2.8927 (12.3); 2.7898 (3.6); 2.7722 (5.0); 2.7673 (7.0); 2.7595 (6.2); 2.7499 (6.2); 2.7425 (8.2); 2.7345 (14.2); 2.7335 (14.0); 2.7195 (5.1); 2.6957 (0.5); 2.6787 (0.8); 2.6741 (1.0); 2.6696 (0.8); 2.5908 (0.5); 2.5749 (0.7); 2.5688 (0.7); 2.5548 (1.2); 2.5408 (1.1); 2.5274 (7.1); 2.5230 (6.9); 2.5141 (56.5); 2.5098 (114.2); 2.5052(148.4); 2.5007 (106.3); 2.4963 (53.6); 2.4885 (8.0); 2.4798 (7.3); 2.4573 (4.1); 2.3365 (0.6); 2.3321 (0.9); 2.3275 (0.7); 2.1044 (0.6); 2.0875 (1.2); 2.0770 (1.7); 2.0707 (1.2); 2.0601 (3.4); 2.0541 (3.1); 2.0484 (3.0); 2.0425 (3.2); 2.0371 (5.3); 2.0321 (4.8); 2.0253 (4.0); 2.0208 (4.1); 2.0144 (4.8); 2.0094 (5.5); 1.9977 (3.1); 1.9929 (3.2); 1.9866 (3.3); 1.9823 (2.6); 1.9749 (1.3); 1.9699 (1.6); 1.9658 (1.4); 1.9591 (1.1); 1.9424 (0.6); 1.2996 (0.6); 1.2915 (0.4); 1.2596 (1.3); 1.2384 (5.7); 0.8688 (0.5); 0.8524 (1.3); 0.8348 (0.6); 0.0079 (0.4); −0.0002(11.1)

I-24: $^1$H-NMR(400.2 MHz, d$_6$-DMSO):
δ = 11.6359 (0.7); 9.7492 (2.5); 9.0037 (10.2); 8.8836 (4.2); 8.7305 (2.3); 8.6550(4.2); 8.6142(1.0); 8.6043 (1.0); 8.6023 (1.0); 8.5803 (5.5); 8.5785 (5.9); 8.5765 (5.3); 8.5686 (5.9); 8.5665 (6.0); 7.9539 (2.2); 7.8317 (0.4); 7.8272 (0.4); 7.8125 (0.7); 8.8082 (0.8); 7.7930 (0.6); 7.7886 (0.6); 7.6758 (2.5); 7.6715 (2.8); 7.6561 (5.0); 7.6524 (5.7); 7.6372 (3.3); 7.6328 (3.5); 7.3572 (0.6); 7.3452 (0.6); 7.3410 (0.6); 7.3384 (0.7); 7.3263 (0.6); 7.3023 (7.4); 7.2823 (6.9); 7.2602 (0.4); 7.2125 (4.2); 7.2004 (4.5); 7.1963 (4.5); 7.1941 (4.2); 7.1840 (3.6); 7.1819 (3.9); 7.1487 (0.9); 7.1288 (0.8); 4.0116 (0.4); 3.4533 (0.3); 3.3349 (31.2); 2.9699 (1.1); 2.9510(2.1); 2.9326 (1.1); 2.8923 (13.4); 2.8668 (0.3); 2.7876 (2.4); 2.7651 (4.6); 2.7581 (4.2); 2.7479 (4.2); 2.7406 (5.5); 2.7335 (16.0); 2.7178 (3.5); 2.6949 (0.6); 2.6775 (0.8); 2.6733 (1.1); 2.5908 (0.5); 2.5744 (0.6); 2.5638 (0.4); 2.5579 (0.5);

2.5496 (0.6); 2.5221 (6.0); 2.5088 (108.0); 2.5044 (142.3); 2.5003 (110.7); 2.4776 (5.2); 2.4549 (2.9); 2.4213 (0.4); 2.3351 (0.7); 2.3312 (0.9); 2.3274 (0.7); 2.1028 (0.4); 2.0863 (0.8); 2.0761 (1.2); 2.0589 (2.3); 2.0532(2.2); 2.0359 (3.5); 2.0309 (3.3); 2.0235 (3.0); 2.0198 (3.0); 2.0132 (3.4); 2.0077 (3.7); 1.9964 (2.6); 1.9915 (2.5); 1.9850 (2.6); 1.9646 (1.4); 1.9579 (1.1); 1.9417 (0.6); 1.2992 (0.5); 1.2592(1.1); 1.2388 (4.8); 0.8692 (0.4); 0.8527 (1.0); 0.8355 (0.4); −0.0003 (8.9)

I-25: $^1$H-NMR(400.2 MHz, $d_6$-DMSO):

δ = 8.9520 (1.3); 8.8313 (1.3); 8.4178 (2.8); 8.2583 (0.9); 3.3381 (14.3); 2.8920 (1.2); 2.7327 (1.0); 2.6720 (0.3); 2.5255 (0.9); 2.5207 (1.4); 2.5119 (21.7); 2.5076 (43.5); 2.5031 (56.0); 2.4986 (39.6); 2.4944 (19.0); 2.3299 (0.3); 1.3920 (16.0); 1.3308 (1.1); 1.2391 (1.5); 0.8530(0.4); 0.7541 (0.9); 0.7359 (3.8); 0.7262 (1.8); 0.7146 (0.8); 0.6908 (0.7); 0.6798 (2.2); 0.6701 (4.1); 0.6659 (3.2); 0.6581 (1.0); 0.6512(1.2); 0.6349 (0.3); −0.0002 (4.5)

I-26: $^1$H-NMR(400.2 MHz, $d_6$-DMSO):

δ = 8.9348 (4.9); 8.8710(4.9); 8.5001 (5.6); 8.4828 (5.7); 7.9531 (0.3); 7.2498 (0.9); 7.2414 (6.9); 7.2331 (8.3); 7.2283 (9.2); 7.2196 (11.6); 7.2104(2.4); 7.1755 (2.4); 7.1654 (16.0); 7.1572 (9.3); 7.1518 (9.8); 7.1436 (10.0); 7.1337 (1.0); 4.7700 (0.6); 4.7525 (2.5); 4.7342 (5.1); 4.7167 (5.2); 4.6983 (2.7); 4.6808 (0.6); 4.0099 (0.4); 3.3288 (55.6); 3.3215 (8.2); 3.3022 (7.2); 3.2816 (8.8); 3.2626 (8.4); 2.9783 (8.6); 2.9613 (8.4); 2.9388 (6.7); 2.9218 (6.7); 2.8915 (2.4); 2.7322 (2.0); 2.7099 (0.4); 2.6769 (0.4); 2.6724 (0.5); 2.6677 (0.4); 2.5724 (0.4); 2.5259 (1.4); 2.5212 (2.2); 2.5125 (30.6); 2.5080 (64.5); 2.5035 (85.8); 2.4989 (61.8); 2.4944 (29.8); 2.3348 (0.4); 2.3303 (0.5); 2.3257 (0.4); 1.2585 (0.6); 1.2368 (3.4); 0.8518 (0.9); 0.8341 (0.3); −0.0002 (7.4)

I-27: $^1$H-NMR(400.2 MHz, $d_6$-DMSO):

δ = 8.9295 (3.5); 8.8307 (3.5); 8.3031 (7.4); 8.2936 (7.3); 8.2692(1.0); 6.5314 (0.4); 4.0111 (0.4); 3.3285 (75.0); 2.8930(2.1); 2.8741 (1.1); 2.8644 (3.3); 2.8549 (4.6); 2.8466 (7.2); 2.8369 (7.4); 2.8284 (4.5); 2.8191 (3.4); 2.8094 (1.2); 2.7330(1.9); 2.7111 (0.4); 2.6781 (0.5); 2.6737 (0.7); 2.6691 (0.5); 2.5737 (0.4); 2.5271 (1.9); 2.5225 (2.7); 2.5136 (41.1); 2.5092 (87.0); 2.5047 (116.3); 2.5002 (84.7); 2.4958 (41.7); 2.3361 (0.5); 2.3315 (0.7); 2.3271 (0.5); 1.2982(0.4); 1.2690 (0.5); 1.2596 (0.8); 1.2374 (3.8); 0.8525 (0.9); 0.8350(0.4); 0.7609 (4.1); 0.7485 (11.5); 0.7433 (16.0); 0.7312 (10.0); 0.7255 (12.2); 0.7139 (5.4); 0.6924 (0.7); 0.6748 (0.6); 0.6110 (0.6); 0.6011 (0.6); 0.5714 (5.5); 0.5604 (14.7); 0.5543 (14.2); 0.5506 (13.4); 0.5449(12.9); 0.5329 (4.2); −0.0002 (10.2); −0.0085 (0.4)

I-28: $^1$H-NMR(400.2 MHz, $d_6$-DMSO):

δ = 8.8641 (8.0); 8.8164 (8.1); 8.2205 (0.4); 8.1908 (7.1); 8.1724 (7.2); 4.3080 (0.6); 4.2908 (2.4); 4.2736 (4.4); 4.2566 (4.3); 4.2396 (2.4); 4.2217 (0.6); 4.0109 (0.4); 3.3283 (62.3); 2.8937 (1.1); 2.7344(1.0); 2.7113 (0.4); 2.6787 (0.4); 2.6566 (0.6); 2.6697 (0.4); 2.5741 (0.4); 2.5275 (1.7); 2.5227 (2.6); 2.5140 (38.5); 2.5097 (78.4); 2.5052(102.0); 2.5008 (73.3); 2.4965 (35.9); 2.3366 (0.4); 2.3320 (0.6); 2.3277 (0.5); 1.9615 (1.1); 1.9512(2.2); 1.9413 (3.9); 1.9383 (3.8); 1.9302 (6.2); 1.9232 (5.9); 1.9148 (6.6); 1.9015 (4.1); 1.8881 (3.1); 1.8654 (0.5); 1.7536 (0.5); 1.7449 (0.9); 1.7347 (1.6); 1.7229 (2.5); 1.7170 (3.9); 1.6999 (9.0); 1.6893 (5.2); 1.6682(2.2); 1.6607 (1.5); 1.6467 (0.8); 1.6203 (0.4); 1.5941 (1.5); 1.5897 (1.4); 1.5715 (5.4); 1.5605 (7.2); 1.5531 (10.7); 1.5428 (16.0); 1.5238 (7.2); 1.5027 (4.0); 1.4888 (1.3); 1.4840 (1.3); 1.2593 (0.6); 1.2365 (3.1); 0.8521 (0.7); −0.0002 (8.0)

I-29: $^1$H-NMR(400.2 MHz, $d_6$-DMSO):

δ = 8.9442(0.9); 8.8857 (0.4); 8.8784 (0.6); 8.8385 (0.6); 8.8312(0.4); 7.9542 (2.3); 7.2701 (0.4); 7.2504 (0.9); 7.2322 (0.9); 7.1843 (0.9); 7.1806 (1.3); 7.1628 (0.7); 7.1600 (0.6); 7.1544(0.3); 7.1513 (0.4); 7.1334 (0.6); 3.3331 (6.5); 2.8924 (16.0); 2.7339 (13.9); 2.5132 (2.7); 2.5087 (5.6); 2.5041 (7.4); 2.4995 (5.2); 2.4950(2.4); 1.3221 (0.9); 1.3155 (0.7); 1.2895 (0.9); −0.0002 (0.6)

I-30: $^1$H-NMR(400.2 MHz, $d_6$-DMSO):

δ = 8.9278 (16.0); 8.5657 (0.7); 8.5379 (10.3); 8.5202 (10.5); 8.3305 (1.0); 7.9527 (1.8); 4.7886 (1.0); 4.7697 (3.4); 4.7515 (5.5); 4.7334 (5.6); 4.7151 (3.6); 4.6962 (1.1); 4.0334 (0.4); 4.0271 (0.4); 4.0109 (0.7); 3.9945 (0.3); 3.5852 (6.6); 3.5664 (6.6); 3.5518 (7.6); 3.5329 (7.3); 3.4487 (0.3); 3.4359 (2.8); 3.4233 (3.1); 3.4163 (3.4); 3.4031 (6.9); 3.3900 (4.7); 3.3831 (4.7); 3.3704 (4.5); 3.3332 (331.4); 3.2589 (4.4); 3.2394 (5.8); 3.2370 (5.8); 3.2256 (3.5); 3.2167 (5.2); 3.2061 (4.0); 3.2036 (4.3); 3.1835 (3.5); 3.0768 (7.7); 3.0575 (7.5); 3.0434 (6.7); 3.0241 (6.6); 2.8922(13.6); 2.7324 (11.8); 2.7105 (0.7); 2.7032 (0.3); 2.6936 (0.4); 2.6820(0.4); 2.6774 (0.8); 2.6729 (1.1); 2.6683 (0.8); 2.6638 (0.4); 2.5899 (0.4); 2.5732 (0.7); 2.5536 (0.6); 2.5403 (2.0); 2.5264 (6.2); 2.5218 (6.8); 2.5129 (67.0); 2.5085 (138.5); 2.5040 (178.2); 2.4994 (126.2); 2.4948 (63.6); 2.4749 (4.2); 2.4608 (2.0); 2.3395 (0.4); 2.3353 (0.8); 2.3308 (1.1); 2.3262 (0.8); 2.3217 (0.4); 2.2696 (2.5); 2.2479 (5.4); 2.2364 (2.3); 2.2265 (5.4); 2.2146 (4.5); 2.2050 (2.6); 2.1931 (4.2); 2.1718 (1.9); 1.2983 (0.7); 1.2894 (0.4); 1.2593 (1.4); 1.2385 (6.1); 0.8691 (0.5); 0.8528 (1.5); 0.8352 (0.6); −0.0002 (4.4)

I-31: $^1$H-NMR(400.2 MHz, $d_6$-DMSO):

δ = 9.5067 (0.9); 8.9431 (3.5); 8.8433 (3.5); 8.8051 (0.4); 8.5186 (1.2); 8.3095 (7.2); 8.3000 (7.1); 8.2689 (0.8); 7.9534 (0.8); 7.5902 (0.3); 7.5821 (0.3); 6.5358 (2.5); 5.8159 (0.5); 4.0108 (0.5); 3.4520 (0.5); 3.3293 (105.1); 2.8926 (5.7); 2.8739 (1.1); 2.8642 (3.2); 2.8548 (4.5); 2.8463 (7.0); 2.8367 (7.1); 2.8281 (4.4); 2.8189 (3.3); 2.8092(1.1); 2.7326 (5.0); 2.7107 (0.6); 2.7073 (0.4); 2.6949 (0.4); 2.6778 (0.6); 2.6731 (0.9); 2.6686 (0.6); 2.5899 (0.4); 2.5735 (0.5); 2.5549 (0.4); 2.5434 (0.4); 2.5266 (2.5); 2.5219 (3.8); 2.5131 (51.2); 2.5087 (106.8); 2.5042 (141.0); 2.4952 (49.3); 2.3355 (0.6); 2.3310 (0.8); 2.3264 (0.6); 1.2982(0.4); 1.2593 (0.8); 1.2377 (3.9); 0.8526 (0.9); 0.8349 (0.4); 0.7614 (4.1); 0.7490 (11.6); 0.7437 (15.9); 0.7316 (16.0); 0.7259 (12.0); 0.7144 (5.4); 0.6928 (0.8); 0.6804 (0.7); 0.6752 (1.3); 0.6632 (0.8); 0.6575 (0.6); 0.6117 (0.6); 0.6018 (0.6); 0.5720 (5.4); 0.5612(14.4); 0.5550 (13.9); 0.5513 (13.0); 0.5456 (12.6); 0.5335 (4.1); 0.5057 (0.4); 0.4966 (0.4); 0.4877 (0.4); 0.4772 (0.7); 0.4711 (0.7); 0.4675 (0.6); 0.4614 (0.6); 0.0079 (0.3); −0.0002(11.3); −0.0085 (0.4)

I-32: $^1$H-NMR(400.2 MHz, $d_6$-DMSO):

δ = 9.5425 (0.4); 8.9186 (16.0); 8.9048 (16.0); 8.6165 (12.0); 8.6003 (12.0); 8.5398 (1.5); 8.3160(0.4); 7.9538 (0.6); 4.3627 (0.4); 4.3565 (0.4); 4.3424 (1.7); 4.3387 (1.7); 4.3247 (4.2); 4.3076 (5.4); 4.2881 (4.3); 4.2741 (1.8); 4.2703 (1.8); 4.2566 (0.5); 4.2501 (0.4); 4.0270 (0.5); 4.0108 (1.0); 3.9943 (0.5); 3.3274 (101.9); 3.0603 (0.4); 3.0493 (3.1); 3.0439 (1.8); 3.0401 (2.0); 3.0343 (3.6); 3.0290 (4.8); 3.0136 (8.0); 3.0073 (5.3); 3.0015 (7.1); 2.9973 (9.0); 2.9925 (7.5); 2.9875 (5.6); 2.9799 (8.2); 2.9692 (4.3); 2.9648 (5.6); 2.9596 (4.5); 2.9543 (2.6); 2.9499 (2.4); 2.9446 (3.3); 2.9346 (0.9); 2.8932(4.1); 2.7784 (3.5); 2.7682 (3.8); 2.7628 (1.9); 2.7592(2.0); 2.7504 (3.9); 2.7452 (2.3); 2.7407 (3.2); 2.7344 (9.0); 2.7249 (6.4); 2.7170 (7.1); 2.7141 (6.7); 2.7073 (6.8); 2.6978 (6.2); 2.6911 (6.3); 2.6883 (6.4); 2.6805 (5.9); 2.6736 (6.3); 2.6704 (5.8); 2.6643 (3.4); 2.6548 (3.1); 2.6456 (1.7); 2.6428 (1.7); 2.6370 (3.1); 2.6271 (0.5); 2.5900 (0.7); 2.5734 (1.0); 2.5559 (0.5); 2.5270 (2.8); 2.5223 (4.2); 2.5135 (59.2); 2.5091 (122.9); 2.5046 (161.9); 2.5000 (116.3); 2.4956 (56.2); 2.3360 (0.7); 2.3314(1.0); 2.3268 (0.7); 1.5533 (0.4); 1.2984 (0.6); 1.2895 (0.5); 1.2596 (1.3); 1.2377 (7.1); 0.8690 (0.6); 0.8524 (1.8); 0.8349 (0.7); 0.0080(0.4); −0.0003 (14.9); −0.0086 (0.5)

I-33: $^1$H-NMR(400.2 MHz, $d_6$-DMSO):

δ = 9.3160 (16.0); 9.1458 (0.6); 9.0697 (2.0); 9.0102 (1.5); 7.9523 (0.7); 6.2027 (0.4); 4.6075 (0.4); 4.5839 (0.5); 4.5313 (2.5); 4.5136 (4.9); 4.4960 (2.7); 4.3924 (0.5); 3.6621 (0.4); 3.6431 (0.4); 3.5355 (0.5); 3.5247 (0.4); 3.5081 (0.7); 3.5060 (0.8); 3.4859 (0.9); 3.4681 (0.8); 3.4532 (0.8); 3.4338 (3.2); 3.4161 (5.5); 3.3984 (3.1); 3.3360 (1.6); 3.2786 (1.0); 3.2590 (1.0); 3.2405 (0.6); 3.1984 (2.5); 3.1775 (0.4); 2.8919 (5.0); 2.7478 (1.1); 2.7316 (4.4); 2.5418 (1.6); 2.5256 (0.8); 2.5120 (17.9); 2.5079 (37.4); 2.5035 (50.6); 2.4990 (39.2); 2.4949 (21.5); 1.2386 (0.8); −0.0002 (3.6)

I-34: $^1$H-NMR(400.2 MHz, d$_6$-DMSO):
δ = 9.9819 (0.7); 9.2986 (16.0); 8.9481 (2.8); 6.5409 (0.4); 6.1321 (0.6); 4.4740 (0.4); 4.4543 (3.1); 4.4370 (5.4); 4.4196 (2.8); 3.3990 (0.6); 3.3813 (1.0); 3.3635 (0.9); 3.3527 (3.7); 3.3355 (8.2); 3.3183 (4.8); 2.8918 (1.9); 2.7316 (1.6); 2.5253 (0.7); 2.5206 (1.1); 2.5119 (14.5); 2.5075 (29.7); 2.5030 (38.7); 2.4984 (27.2); 2.4939 (12.8); 1.2385 (1.2); −0.0002 (3.1)
I-35: $^1$H-NMR(300.2 MHz, d$_6$-DMSO):
δ = 8.1765 (1.7); 8.1485 (2.0); 7.7409 (0.4); 7.4615 (0.7); 7.4262 (0.8); 7.4016 (1.0); 7.3797 (0.6); 7.2905 (0.4); 3.3414 (16.0); 2.5340(1.4); 2.5281 (2.9); 2.5221 (3.9); 2.5160 (2.8); 2.5102 (1.3); 2.3476 (8.4); 2.3137 (0.6); 0.0192 (3.2)
I-36: $^1$H-NMR(300.2 MHz, CDCl3):
δ = 8.0896 (0.5); 8.0811 (3.6); 8.0747 (1.2); 8.0585 (1.2); 8.0519 (3.9); 8.0436 (0.5); 7.5142 (0.5); 7.4872 (1.3); 7.4618(1.1); 7.4328 (1.7); 7.3954(1.2); 7.3665 (0.7); 7.3397 (1.2); 7.3139 (1.0); 7.2987 (22.7); 7.1992 (0.5); 7.1908 (4.0); 7.1842 (1.3); 7.1681 (1.2); 7.1615 (3.8); 7.1531 (0.5); 6.1451 (1.2); 2.0463 (0.9); 1.5767 (16.0); 0.0495 (1.0); 0.0387 (28.9); 0.0277 (1.1)
I-37: $^1$H-NMR(300.2 MHz, CDCl3):
δ = 8.0264 (15.1); 7.9972 (16.0); 7.4198 (5.9); 7.3923 (11.9); 7.3674 (9.5); 7.2987 (27.3); 7.2389 (13.8); 7.2137 (9.8); 7.1425 (20.2); 7.1192 (13.0); 7.1132 (18.0); 7.0950 (3.4); 6.0550 (5.2); 1.5815 (11.8); 0.0400 (32.4); 0.0293 (2.0)
I-38: $^1$H-NMR(300.2 MHz, CDCl3):
δ = 8.0584 (0.5); 8.0439 (1.9); 8.0356 (15.3); 8.0292 (4.8); 8.0129 (4.9); 8.0064 (16.0); 7.9981 (1.9); 7.8372 (0.3); 7.7728 (0.4); 7.4262(0.4); 7.3984 (0.5); 7.3672 (1.6); 7.3570 (13.9); 7.3500(4.9); 7.3349 (5.3); 7.3277 (18.6); 7.3176 (2.4); 7.2982 (41.6); 7.2671 (0.4); 7.2610(0.4); 7.2509 (0.4); 7.2316 (0.7); 7.2039 (0.4); 7.1759 (2.2); 7.1659 (18.2); 7.1588 (5.2); 7.1436 (4.5); 7.1367 (13.4); 7.1230 (2.5); 7.1144 (17.1); 7.1078 (5.2); 7.0915 (5.0); 7.0850 (15.6); 7.0767 (1.8); 6.7892 (0.4); 6.0206 (5.0); 2.9965 (3.1); 2.9246 (2.7); 1.5814 (9.2); 1.5129 (2.3); 1.4070 (0.3); 0.0549 (0.4); 0.0493 (1.8); 0.0386 (54.7); 0.0277 (2.0)
I-39: $^1$H-NMR(400.1 MHz, d$_6$-DMSO)
δ = 8.6116 (11.8); 7.9132 (14.6); 7.8915 (16.0); 7.8693 (0.6); 7.8182 (0.6); 7.5000 (5.0); 7.4798 (7.3); 7.4481 (4.9); 7.4278 (5.7); 7.4039 (3.9); 7.3849 (6.6); 7.3655 (3.4); 7.2098 (3.8); 7.2066 (3.8); 7.1893 (6.0); 7.1709 (3.0); 7.1285 (15.5); 7.1068 (15.2); 3.9367 (0.8); 3.3688 (0.7); 3.3226 (867.3); 3.1992 (0.7); 3.1691 (0.5); 3.1347 (0.3); 3.0310 (0.7); 2.8981 (0.8); 2.7392 (0.7); 2.6775 (0.4); 2.5084 (63.8); 2.5046 (49.6); 2.3361 (0.5); 1.4351 (2.5)
I-40: $^1$H-NMR(300.2 MHz, d$_6$-DMSO):
δ = 10.1023 (1.0); 8.4546 (1.0); 8.4379 (1.0); 8.0785 (0.8); 8.0491 (1.9); 7.9987 (1.8); 7.9692 (0.9); 6.8833 (0.9); 6.8664 (0.9); 3.3490 (16.0); 2.5288 (3.0); 2.5232 (4.3); 2.5176 (3.3); 2.4313 (4.6); 0.0207 (4.3)
I-41: $^1$H-NMR(300.2 MHz, d$_6$-DMSO):
δ = 9.9928 (0.8); 9.0051 (3.2); 7.6424 (0.3); 7.6357 (0.4); 7.3161 (0.4); 7.2904 (0.5); 7.2833 (0.6); 7.2740 (0.6); 7.2663 (0.9); 7.2581 (0.4); 7.2420 (0.5); 3.3454 (16.0); 2.5344 (1.3); 2.5288 (2.6); 2.5227 (3.4); 2.5168 (2.5); 0.0208 (4.6)
I-42: $^1$H-NMR(400.2 MHz, d$_6$-DMSO):
δ = 9.9568 (5.5); 9.0610 (0.3); 8.9889 (16.0); 8.6145 (0.4); 7.6332 (1.2); 7.6176 (1.4); 7.6108 (2.4); 7.5952 (2.4); 7.5884 (1.4); 7.5729 (1.2); 7.3835 (1.2); 7.3764 (1.3); 7.3605 (1.5); 7.3546 (2.0); 7.3499 (1.6); 7.3340(1.2); 7.3269 (1.2); 7.1480(1.0); 7.1426 (1.0); 7.1273 (1.9); 7.1220 (1.8); 7.1050(1.0); 7.1008 (0.9); 3.3358 (47.6); 2.5092 (20.3); 2.5050 (25.6); 2.5006 (18.4); 1.2380 (1.0); −0.0002 (0.4)
I-43: $^1$H-NMR(400.2 MHz, d$_6$-DMSO):
δ = 10.4295 (4.4); 9.0573 (16.0); 7.8070 (5.4); 7.8021 (2.0); 7.7844 (5.9); 7.7763 (0.7); 7.3477 (1.9); 7.1918 (5.1); 7.1695 (5.0); 7.1618 (4.6); 6.9759 (2.0); 3.3327 (40.6); 2.5087 (18.4); 2.5044 (23.5); 2.5000 (17.0); 1.2361 (0.5); −0.0002 (0.5)
I-44: $^1$H-NMR(400.2 MHz, d$_6$-DMSO):
δ = 10.5791 (3.7); 9.1105 (16.0); 7.8354(1.1); 7.8300 (1.8); 7.8246 (1.1); 7.8051 (1.1); 7.7998 (1.8); 7.7944(1.1); 7.5549 (1.6); 7.5528 (1.6); 7.5343 (2.0); 7.5318 (2.0); 7.3972 (1.0); 7.3770(2.0); 7.3590 (2.0); 7.3388 (0.9); 6.8896 (0.9); 6.8834 (0.9); 6.8684 (1.6); 6.8625 (1.6); 6.8474 (0.9); 6.8412 (0.8); 3.3347 (31.2); 2.8925 (0.4); 2.7332 (0.3); 2.5088 (16.2); 2.5052 (20.6); 2.5010 (15.4); 1.2342 (0.7); −0.0002 (0.3)
I-45: $^1$H-NMR(400.2 MHz, d$_6$-DMSO):
δ = 10.3445 (2.8); 9.0697 (11.7); 9.0571 (0.3); 7.4926 (1.6); 7.4874 (2.6); 7.4819 (1.6); 7.3692(1.1); 7.3664(1.0); 7.3488 (1.5); 7.3461 (1.5); 7.2646 (1.6); 7.2442 (2.6); 7.2239 (1.2); 6.6606 (1.2); 6.6546 (1.2); 6.6403 (1.2); 6.6343 (1.2); 3.7593 (16.0); 3.3345 (23.9); 2.5090 (12.7); 2.5047 (15.9); 2.5003 (11.5)
I-46: $^1$H-NMR(400.2 MHz, d$_6$-DMSO):
δ = 10.5545 (4.2); 9.1123 (10.9); 9.1104 (16.0); 7.9874 (2.7); 7.9826 (4.4); 7.9778 (2.4); 7.7245 (1.9); 7.7217 (1.8); 7.7057 (2.0); 7.7037 (2.1); 7.7010(2.0); 7.3869 (1.9); 7.3667 (3.6); 7.3463 (2.0); 7.1092 (2.1); 7.1070(2.2); 7.1042 (2.1); 7.0893 (1.9); 7.0871 (1.9); 7.0843 (1.9); 3.3344 (31.2); 2.8937 (1.7); 2.7350 (1.5); 2.5105 (17.0); 2.5062 (21.9); 2.5019 (16.4); 1.2337 (0.5); −0.0002 (0.4)
I-47: $^1$H-NMR(400.2 MHz, d$_6$-DMSO):
δ = 9.8777 (4.3); 8.9841 (16.0); 7.6280 (2.2); 7.6083 (2.6); 7.5632 (2.4); 7.5602 (2.4); 7.5432 (2.8); 7.5403 (2.8); 7.4113 (1.2); 7.4087 (1.2); 7.3924 (2.5); 7.3899 (2.4); 7.3732 (1.5); 7.3704(1.4); 7.3043 (1.6); 7.3009 (1.6); 7.2851 (2.3); 7.2817 (2.3); 7.2659 (1.0); 7.2623 (1.0); 3.3329 (80.4); 2.8907 (1.0); 2.7314(1.0); 2.5643 (0.5); 2.5507 (1.0); 2.5370 (0.6); 2.5063 (39.1); 2.5025 (49.6); 2.4983 (37.2); 1.2392 (1.0); −0.0002 (0.8)
I-48: $^1$H-NMR(400.2 MHz, d$_6$-DMSO):
δ = 10.4341 (4.2); 9.0672 (16.0); 7.8035 (5.2); 7.7822 (5.7); 7.3360 (5.1); 7.3148 (4.6); 3.9890(11.2); 3.3336 (32.8); 2.8921 (1.4); 2.7332 (1.3); 2.5085 (20.0); 2.5044 (24.5); 2.5003 (17.7); 1.2362 (0.5); −0.0004 (0.4)
I-49: $^1$H-NMR(400.2 MHz, d$_6$-DMSO):
δ = 10.2488 (4.7); 9.0173 (16.0); 7.4504 (4.4); 7.4454 (4.4); 7.1521 (2.0); 7.1473 (1.9); 7.1311 (2.4); 7.1262 (2.3); 6.9045 (4.4); 6.8835 (3.8); 6.0053 (15.6); 3.3334 (34.5); 2.5078 (19.6); 2.5043 (24.2); 2.5003 (17.8); 1.2345 (0.5); −0.0002 (0.4)
I-50: $^1$H-NMR(400.2 MHz, d$_6$-DMSO):
δ = 10.3561 (3.5); 9.9564 (2.4); 9.0406 (13.2); 7.9439 (2.8); 7.4574 (1.3); 7.4357 (1.5); 7.3502 (1.1); 7.3292 (1.7); 7.2601 (1.8); 7.2400 (2.6); 7.2198 (1.0); 3.3416 (49.7); 2.8918 (1.2); 2.7324(1.1); 2.5089 (16.2); 2.5047 (20.9); 2.5004 (15.5); 2.0486 (16.0); 1.2360 (0.4); −0.0002 (0.3)
I-51: $^1$H-NMR(400.2 MHz, d$_6$-DMSO):
δ = 10.6996 (4.0); 9.1377 (16.0); 8.3049 (3.5); 8.0431 (1.6); 8.0204 (1.7); 7.9545 (0.6); 7.5836 (1.3); 7.5640 (2.9); 7.5440(2.2); 7.5076 (3.0); 7.4915 (1.2); 7.4885 (1.7); 3.3353 (34.4); 2.8940 (3.5); 2.7349 (3.2); 2.5106 (16.3); 2.5063 (21.3); 2.5022(16.4); 1.2339 (0.5); −0.0002 (0.4)
I-52: $^1$H-NMR(400.2 MHz, d$_6$-DMSO):
δ = 10.2562 (3.3); 9.0439 (13.7); 7.4364 (2.7); 7.4320 (2.8); 7.3068 (1.4); 7.3021 (1.4); 7.2867 (1.7); 7.2819 (1.7); 7.0856 (2.3); 7.0653 (1.9); 3.7849 (16.0); 3.7648 (0.4); 3.3318 (41.9); 2.5080 (17.2); 2.5037 (22.2); 2.4993 (16.4); 2.1142(12.1); 2.0923 (0.3); 1.2366 (0.4); −0.0002 (0.4)
I-53: $^1$H-NMR(400.2 MHz, d$_6$-DMSO):
δ = 10.6760 (4.3); 9.1248 (16.0); 8.2179 (3.4); 8.0868 (1.7); 8.0660 (1.8); 7.6060(1.2); 7.5862 (2.5); 7.5661 (1.4); 7.3981 (2.2); 7.3788 (1.8); 3.3348 (38.9); 2.8933 (1.5); 2.7341 (1.4); 2.5099 (18.9); 2.5060 (23.9); 2.5017 (17.6); 1.2339 (0.6); −0.0002 (0.4)

-continued

I-54: $^1$H-NMR(400.2 MHz, d$_6$-DMSO):
δ = 9.1674 (2.8); 8.9811 (11.3); 7.7706 (1.6); 7.7512 (1.6); 7.1977 (0.6); 7.1938 (0.6); 7.1770 (1.5); 7.1588 (1.2); 7.1550 (1.2); 7.1032(2.2); 7.0851 (1.4); 6.9995 (1.0); 6.9802 (1.8); 6.9616 (0.8); 3.8168 (16.0); 3.3348 (39.1); 2.5075 (18.0); 2.5034 (22.7); 2.4991 (16.7); 1.2391 (0.4); −0.0002 (0.3)

I-55: $^1$H-NMR(400.2 MHz, d$_6$-DMSO):
δ = 10.8305 (4.4); 9.1480 (16.0); 8.0178 (3.1); 7.7953 (4.5); 7.8924 (5.7); 7.8693 (4.2); 3.3333 (49.8); 2.8930 (0.3); 2.5097 (22.7); 2.5054 (28.8); 2.5010 (20.9); 1.2353 (0.6); −0.0002 (0.5)

I-56: $^1$H-NMR(400.2 MHz, d$_6$-DMSO):
δ = 10.2907 (3.8); 9.0541 (16.0); 7.6121 (1.5); 7.5917 (1.8); 7.5614 (3.2); 7.2468 (1.6); 7.2274 (3.0); 7.2077 (1.7); 6.8938 (2.0); 6.8749 (1.8); 3.3293 (147.1); 2.8908 (0.4); 2.7314(0.4); 2.6712(0.4); 2.5065 (58.2); 2.5023 (74.2); 2.4980 (54.6); 2.3287 (0.6); 2.3242 (0.6); 2.3082 (15.5); 2.2841 (0.4); 1.2392 (1.3); −0.0002 (0.9)

I-57: $^1$H-NMR(400.2 MHz, d$_6$-DMSO):
δ = 11.2339 (3.4); 9.7375 (0.4); 9.1286 (16.0); 8.8288 (4.5); 8.8246 (4.5); 8.7455 (0.8); 7.1276 (4.6); 7.1233 (4.6); 6.5341 (0.3); 3.3326 (64.3); 2.8919 (1.0); 2.7321 (0.9); 2.5072 (24.3); 2.5040 (30.9); 2.4997 (23.0); 1.2379 (0.6); −0.0002 (0.5)

I-58: $^1$H-NMR(400.2 MHz, d$_6$-DMSO):
δ = 10.7136 (6.7); 9.0701 (16.0); 8.7052 (0.5); 7.7088 (4.3); 7.7058 (4.6); 7.7009 (4.9); 7.6978 (4.6); 7.5053 (4.2); 7.4973 (4.2); 7.4925 (4.9); 7.4844 (4.3); 7.2715 (4.5); 7.2684 (4.7); 7.2586 (4.2); 7.2555 (4.3); 6.5348 (1.1); 3.3344 (73.5); 2.8915 (1.5); 2.7321 (1.4); 2.5082 (39.6); 2.5039 (51.2); 2.4994 (37.5); 1.2361 (1.0); −0.0002 (0.9)

I-59: $^1$H-NMR(400.2 MHz, d$_6$-DMSO):
δ = 10.1936 (2.9); 8.9989 (10.3); 7.6464 (3.5); 7.6239 (3.9); 7.6154 (0.4); 6.9424 (3.8); 6.9199 (3.6); 6.9114 (0.4); 3.7461 (16.0); 3.7248 (0.6); 3.3316 (33.6); 2.8914 (0.8); 2.7321 (0.7); 2.5079 (15.7); 2.5036 (20.2); 2.4994 (15.0); 1.2361 (0.4); −0.0002(0.4)

I-60: $^1$H-NMR(400.2 MHz, d$_6$-DMSO):
δ = 9.8020 (4.1); 8.9711 (16.0); 7.3450 (2.5); 7.3257 (3.0); 7.1622 (1.5); 7.1435 (3.2); 7.1242 (2.0); 7.0800 (3.2); 7.0618 (2.0); 3.3314 (31.0); 2.9225 (2.3); 2.9041 (4.6); 2.8855 (2.6); 2.8361 (2.4); 2.8178 (4.7); 2.7993 (2.6); 2.7330(0.4); 2.5076 (21.2); 2.5032 (27.1); 2.4988 (19.8); 2.0246 (0.8); 2.0060 (2.7); 1.9876 (3.7); 1.9692 (2.5); 1.9504 (0.7); 1.2372(0.4); −0.0002 (0.5)

I-61: $^1$H-NMR(400.2 MHz, d$_6$-DMSO):
δ = 10.3672 (3.6); 9.0589 (16.0); 7.7878 (3.9); 7.7679 (4.3); 7.3674 (2.6); 7.3480 (4.2); 7.3279 (2.7); 7.0790 (1.4); 7.0606 (2.4); 7.0422(1.1); 3.3330 (34.0); 2.5086 (15.0); 2.5043 (19.7); 2.4999 (14.8); 1.2350(0.4); −0.0002 (0.4)

I-62: $^1$H-NMR(400.2 MHz, d$_6$-DMSO):
δ = 10.5065 (3.9); 9.0770 (16.0); 9.0424 (0.9); 7.8340 (5.0); 7.8117 (5.7); 7.8043 (0.8); 7.4121 (5.7); 7.3946 (1.8); 7.3898 (5.2); 7.3822 (0.7); 3.7848 (1.0); 3.3333 (38.2); 2.8924(1.4); 2.7331 (1.3); 2.5095 (16.6); 2.5051 (21.9); 2.5008 (16.7); 2.1131 (0.8); 1.2343 (0.4); −0.0002 (0.4)

I-63: $^1$H-NMR(400.2 MHz, d$_6$-DMSO):
δ = 10.3927 (4.2); 9.0471 (16.0); 7.7931 (2.8); 7.7806 (3.0); 7.7753 (2.0); 7.7703 (3.2); 7.7579 (3.0); 7.7492(0.4); 7.2159 (3.0); 7.2105 (1.1); 7.1935 (5.4); 7.1767 (1.1); 7.1715 (2.8); 7.1625 (0.3); 3.3333 (35.6); 2.8926 (0.6); 2.7334 (0.6); 2.5095 (15.8); 2.5053 (20.2); 2.5010 (14.9); 1.2347 (0.7); −0.0002 (0.3)

I-64: $^1$H-NMR(400.2 MHz, d$_6$-DMSO):
δ = 11.2285 (3.6); 9.1149 (16.0); 8.8716 (0.7); 8.8278 (4.3); 8.8237 (4.2); 7.9530(0.4); 7.1270 (4.5); 7.1228 (4.6); 3.3340(44.0); 2.8923 (2.1); 2.7324 (1.9); 2.5485 (0.7); 2.5084 (24.4); 2.5043 (31.9); 2.5000 (24.1); 1.2378 (0.6); −0.0002 (0.5)

I-65: $^1$H-NMR(400.2 MHz, d$_6$-DMSO):
δ = 10.7104 (7.1); 9.0561 (16.0); 7.7041 (5.0); 7.6989 (5.0); 7.6962(4.9); 7.5034 (3.7); 7.4953 (3.8); 7.4906 (4.5); 7.4825 (3.9); 7.2700 (4.6); 7.2683 (5.0); 7.2572 (4.3); 7.2554 (4.6); 3.3351 (26.6); 2.8919 (0.5); 2.7329 (0.4); 2.5631 (0.4); 2.5495 (0.8); 2.5357 (0.5); 2.5088 (31.7); 2.5046 (40.2); 2.5002 (29.2); 1.2348 (0.8); −0.0002 (0.8)

I-66: $^1$H-NMR(400.2 MHz, d$_6$-DMSO):
δ = 10.1908 (3.0); 8.9857 (9.6); 8.8133 (0.5); 7.6477 (3.7); 7.6252(4.0); 6.9416 (3.8); 6.9191 (3.6); 6.9105 (0.7); 3.7464 (16.0); 3.3377 (16.0); 2.8926 (0.4); 2.7338 (0.3); 2.5467 (0.5); 2.5092 (12.5); 2.5052 (16.0); 2.5011 (12.1); 1.2360(0.4)

I-67: $^1$H-NMR(400.2 MHz, d$_6$-DMSO):
δ = 10.5034 (4.0); 9.0637 (16.0); 8.8283 (0.4); 7.8339 (5.4); 7.8290 (1.9); 7.8164(2.2); 7.8116 (6.1); 7.8041 (0.8); 7.4109 (5.9); 7.4062(2.0); 7.3934(2.0); 7.3887 (5.4); 7.3808 (0.7); 3.3400 (25.2); 2.8930 (0.3); 2.5646 (0.3); 2.5510 (0.7); 2.5371 (0.4); 2.5103 (16.8); 2.5059 (21.6); 2.5015 (15.6); 1.2339 (0.4); −0.0002 (0.4)

I-68: $^1$H-NMR(400.2 MHz, d$_6$-DMSO):
δ = 10.2859 (4.0); 9.0374 (15.8); 7.6125 (1.7); 7.5919 (1.9); 7.5616 (3.4); 7.2437 (1.7); 7.2242 (3.1); 7.2047 (1.7); 6.8902 (2.2); 6.8714 (1.9); 3.3356 (23.0); 2.8914 (0.3); 2.5492 (0.6); 2.5352(0.4); 2.5041 (22.9); 2.4999 (17.1); 2.3074 (16.0); 1.2351 (0.5); −0.0002 (0.4)

I-69: $^1$H-NMR(400.2 MHz, d$_6$-DMSO):
δ = 10.4278 (4.5); 9.0452 (16.0); 8.8082(0.4); 7.8081 (5.8); 7.7856 (6.2); 7.7776 (0.8); 7.3484(2.1); 7.1928 (5.6); 7.1704 (5.5); 7.1625 (5.1); 6.9766 (2.2); 3.3371 (33.7); 2.8930 (0.5); 2.7343 (0.4); 2.5506 (0.3); 2.5097 (20.5); 2.5054 (25.0); 2.5012 (17.7); 1.2366 (0.5); −0.0002 (0.4)

I-70: $^1$H-NMR(400.2 MHz, d$_6$-DMSO):
δ= 10.2484 (1.8); 9.0069 (6.7); 8.8333 (0.9); 7.9541 (2.6); 7.4533 (1.8); 7.4483 (1.8); 7.1536 (0.9); 7.1485 (1.0); 7.1325 (1.0); 7.1274(1.0); 6.9058 (1.8); 6.8991 (0.4); 6.8848 (1.6); 6.8783 (0.4); 6.0058 (7.4); 3.3644 (10.6); 2.8935 (16.0); 2.7344 (14.7); 2.5558 (0.6); 2.5419 (1.1); 2.5280 (0.8); 2.5102 (12.2); 2.5059 (15.5); 2.5018 (11.5); 1.2373 (0.4)

I-71: $^1$H-NMR(400.2 MHz, d$_6$-DMSO):
δ = 10.3638 (3.7); 9.0467 (16.0); 9.0389 (1.0); 7.7878 (4.1); 7.7685 (4.4); 7.3672 (2.6); 7.3481 (4.2); 7.3275 (2.8); 7.0779 (1.4); 7.0595 (2.5); 7.0412 (1.1); 3.3367 (32.8); 2.5493 (0.6); 2.5354 (0.5); 2.5089 (17.8); 2.5046 (22.8); 2.5003 (17.3); 1.2361 (0.4); −0.0002 (0.4)

I-72: $^1$H-NMR(400.2 MHz, d$_6$-DMSO):
δ = 10.3891 (4.2); 9.0350 (16.0); 7.7932 (2.8); 7.7807 (3.1); 7.7756 (2.1); 7.7704 (3.3); 7.7580 (3.1); 7.7495 (0.4); 7.2158 (3.0); 7.1936 (5.3); 7.1714 (2.8); 3.3410 (59.7); 2.8932 (1.3); 2.7338 (1.2); 2.5103 (18.3); 2.5060 (23.2); 2.5017 (17.1); 1.2352 (0.5)

I-73: $^1$H-NMR(400.2 MHz, d$_6$-DMSO):
δ = 9.7959 (4.1); 8.9585 (16.0); 8.7233 (0.4); 7.9532 (1.9); 7.3452 (2.5); 7.3257 (3.0); 7.1618 (1.5); 7.1429 (3.2); 7.1237 (2.0); 7.0792 (3.1); 7.0608 (1.9); 3.3384 (51.0); 2.9220 (2.3); 2.9034 (4.8); 2.8915 (12.9); 2.8352(2.4); 2.8168 (4.7); 2.7983 (2.6); 2.7493 (0.4); 2.7325 (10.8); 2.5623 (0.8); 2.5488 (0.9); 2.5350 (0.6); 2.5077 (26.3); 2.5035 (33.0); 2.4991 (23.8); 2.0241 (0.8); 2.0056 (2.7); 1.9871 (3.7); 1.9687 (2.5); 1.9499 (0.7); 1.2384 (0.6); −0.0002 (0.6)

I-74: $^1$H-NMR(400.2 MHz, d$_6$-DMSO):
δ = 10.3529 (3.4); 9.9547 (2.4); 9.0285 (13.6); 7.9420 (2.7); 7.4569 (1.2); 7.4383 (1.5); 7.4364 (1.5); 7.3498 (1.1); 7.3296 (1.7); 7.2591 (1.8); 7.2390 (2.6); 7.2188 (1.0); 3.3359 (39.0); 2.8916 (0.5); 2.7323 (0.5); 2.5087 (16.9); 2.5043 (22.1); 2.4999 (16.4); 2.0482 (16.0); 1.2369 (0.8); −0.0002 (0.4)

I-75: $^1$H-NMR(400.2 MHz, d$_6$-DMSO):

δ = 9.9523 (5.6); 8.9763 (16.0); 8.7364 (0.4); 7.6335 (1.1); 7.6180 (1.3); 7.6112(2.4); 7.5957 (2.4); 7.5890(1.4); 7.5733 (1.2); 7.3839 (1.2); 7.3769 (1.3); 7.3605 (1.6); 7.3564 (2.0); 7.3504 (1.7); 7.3344 (1.3); 7.3274 (1.3); 7.1506 (1.0); 7.1475 (1.1); 7.1436 (1.0); 7.1269 (2.0); 7.1223 (1.9); 7.1076 (1.0); 7.1047 (1.0); 7.1004 (1.0); 3.7601 (0.4); 3.3364 (48.2); 2.8933 (0.4); 2.7343 (0.3); 2.5513 (0.5); 2.5093 (26.3); 2.5052 (31.9); 2.5012 (22.9); 1.2390 (0.6); −0.0002 (0.5)

I-76: $^1$H-NMR(400.2 MHz, d$_6$-DMSO):

δ = 10.5759 (3.8); 9.0979 (16.0); 8.8590 (0.3); 7.8354(1.1); 7.8300 (1.8); 7.8249 (1.2); 7.8052(1.1); 7.7999 (1.8); 7.7946 (1.2); 7.5541 (1.8); 7.5515 (1.7); 7.5334 (2.2); 7.5309 (2.2); 7.3969 (1.0); 7.3766 (2.1); 7.3589 (2.0); 7.3385 (0.9); 6.8880 (0.9); 6.8818 (0.9); 6.8670 (1.7); 6.8612 (1.6); 6.8459 (0.9); 6.8412 (0.8); 6.8397 (0.8); 3.3403 (53.3); 2.5519 (0.4); 2.5102 (18.0); 2.5059 (23.0); 2.5015 (16.8); 1.2340 (0.5)

I-77: $^1$H-NMR(400.2 MHz, d$_6$-DMSO):

δ = 9.8692(4.2); 8.9722 (16.0); 8.7352 (0.4); 7.9533 (1.2); 7.6313 (2.1); 7.6115 (2.5); 7.5630(2.2); 7.5601 (2.4); 7.5431 (2.7); 7.5402 (2.7); 7.4117 (1.2); 7.4086 (1.2); 7.3921 (2.4); 7.3900 (2.4); 7.3735 (1.4); 7.3702(1.4); 7.3035 (1.5); 7.2998 (1.6); 7.2837 (2.3); 7.2807 (2.2); 7.2650 (1.0); 7.2613 (1.0); 3.3379 (38.8); 2.8918 (7.2); 2.7494 (0.4); 2.7323 (6.7); 2.5627 (0.4); 2.5490 (0.9); 2.5350 (0.5); 2.5080(21.4); 2.5038 (27.3); 2.4995 (20.1); 1.2385 (0.6); −0.0002(0.4)

I-78: $^1$H-NMR(400.2 MHz, d$_6$-DMSO):

δ = 9.1526 (2.6); 8.9682 (11.4); 7.7764 (1.5); 7.7594 (1.6); 7.7569 (1.6); 7.1948 (0.6); 7.1910 (0.7); 7.1740 (1.5); 7.1560 (1.2); 7.1521 (1.2); 7.1014 (2.3); 7.0836 (1.3); 7.0809 (1.3); 6.9988 (1.0); 6.9958 (1.1); 6.9769 (1.7); 6.9609 (0.8); 6.9578 (0.9); 3.8178 (16.0); 3.3379 (26.2); 2.8917 (0.6); 2.7332 (0.5); 2.5485 (0.5); 2.5345 (0.4); 2.5082 (13.0); 2.5038 (16.7); 2.4995 (12.7); 1.2373 (0.4)

I-79: $^1$H-NMR(400.2 MHz, d$_6$-DMSO):

δ = 10.5516 (3.9); 9.0983 (16.0); 9.0958 (0.5); 7.9873 (2.4); 7.9824(4.1); 7.9775 (2.4); 7.9548 (0.5); 7.7249 (1.8); 7.7222 (1.7); 7.7202 (1.6); 7.7041 (2.0); 7.7014 (2.0); 7.3868 (1.9); 7.3665 (3.5); 7.3462(2.0); 7.1064 (2.1); 7.1037 (2.1); 7.1014 (1.9); 7.0885 (1.5); 7.0865 (1.8); 7.0837 (1.8); 7.0815 (1.6); 3.3416 (20.8); 2.8933 (2.8); 2.7337 (2.4); 2.5641 (0.4); 2.5504 (0.9); 2.5364 (0.6); 2.5103 (17.0); 2.5059 (21.6); 2.5016 (15.9); 1.2332 (0.5); −0.0002 (0.4)

I-80: $^1$H-NMR(400.2 MHz, d$_6$-DMSO):

δ = 10.3409 (3.0); 9.0573 (11.7); 9.0445 (0.6); 7.4945 (1.6); 7.4893 (2.6); 7.4841 (1.6); 7.3675 (1.2); 7.3652(1.1); 7.3472 (1.6); 7.3447 (1.6); 7.2634 (1.5); 7.2430 (2.5); 7.2227 (1.2); 6.6577 (1.3); 6.6516 (1.2); 6.6373 (1.2); 6.6329 (1.1); 6.6312(1.1); 3.7589 (16.0); 3.3341 (31.2); 2.8918 (1.6); 2.7326 (1.5); 2.5087 (13.3); 2.5045 (17.2); 2.5001 (12.7); 1.2351 (0.4)

I-81: $^1$H-NMR(400.2 MHz, d$_6$-DMSO):

δ = 10.2536 (3.5); 9.0320 (12.7); 7.4421 (2.9); 7.4381 (2.9); 7.3021 (1.5); 7.2976 (1.4); 7.2819 (1.8); 7.2774 (1.7); 7.0843 (2.5); 7.0640(2.1); 3.7846 (16.0); 3.7650 (0.7); 3.3334 (34.9); 2.8914(1.1); 2.7324 (1.0); 2.5485 (0.4); 2.5076 (18.8); 2.5038 (23.4); 2.4996 (17.3); 2.1135 (12.8); 1.2359 (0.5); −0.0002 (0.4)

I-82: $^1$H-NMR(400.2 MHz, d$_6$-DMSO):

δ = 10.6973 (4.3); 9.1254 (16.0); 8.8823 (0.6); 8.3042 (3.7); 8.0441(1.7); 8.0419 (1.7); 8.0236 (1.8); 8.0210 (1.9); 7.5829 (1.4); 7.5633 (3.2); 7.5432 (2.3); 7.5064 (3.0); 7.4872 (1.7); 3.3396 (34.4); 2.8936 (1.5); 2.7340(1.4); 2.5646 (0.4); 2.5511 (0.9); 2.5376 (0.5); 2.5105 (19.3); 2.5062 (25.1); 2.5019 (18.7); 1.2336 (0.5); −0.0002 (0.4)

I-83: $^1$H-NMR(400.2 MHz, d$_6$-DMSO):

δ = 10.8293 (5.2); 9.1361 (13.3); 9.1340 (16.0); 8.8995 (0.8); 8.0187 (3.9); 7.9962 (5.7); 7.9724 (0.4); 7.9561 (0.9); 7.8906 (6.3); 7.8675 (4.4); 3.3378 (28.9); 2.8946 (5.4); 2.7533 (0.3); 2.7359 (4.9); 2.5649 (0.5); 2.5523 (1.2); 2.5390 (0.6); 2.5116 (26.4); 2.5071 (34.3); 2.5027 (25.5); 1.2344 (0.7); −0.0002 (0.6)

I-84: $^1$H-NMR(400.2 MHz, d$_6$-DMSO):

δ = 10.4309 (4.5); 9.0557 (16.0); 8.8188 (0.4); 7.8030 (5.2); 7.7817 (5.8); 7.3355 (5.1); 7.3144(4.7); 3.9884 (11.5); 3.3359 (59.4); 2.8916 (0.9); 2.7326 (0.9); 2.5628 (0.5); 2.5491 (0.9); 2.5352 (0.6); 2.5075 (30.7); 2.5037 (37.8); 2.4998 (27.7); 1.2381 (0.7); −0.0002 (0.6)

I-85: $^1$H-NMR(400.2 MHz, d$_6$-DMSO):

δ = 10.6746 (4.2); 9.1134 (16.0); 8.8767 (0.5); 8.2207 (3.2); 8.0854 (1.6); 8.0650 (1.7); 7.6062(1.2); 7.5863 (2.4); 7.5662(1.4); 7.3974(2.1); 7.3781 (1.7); 3.3434 (39.0); 2.8938 (1.2); 2.7344(1.0); 2.5656 (0.5); 2.5518 (1.0); 2.5379 (0.6); 2.5108 (19.8); 2.5065 (25.6); 2.5021 (19.1); 1.2339 (0.5); −0.0002 (0.4)

I-87: $^1$H-NMR(400.2 MHz, d$_6$-DMSO):

δ = 10.7693 (4.0); 9.7980 (0.4); 9.1568 (16.0); 8.9194 (0.6); 8.8144 (2.0); 8.8108 (2.2); 8.8039 (2.2); 8.8002 (2.2); 8.5381 (3.2); 8.5326 (3.3); 8.3457 (1.7); 8.3253 (1.9); 8.0908 (1.2); 8.0850(1.2); 8.0679 (2.4); 8.0622(2.4); 8.0225 (3.8); 7.9997 (2.0); 7.5454 (1.8); 7.5349 (1.8); 7.5247 (1.8); 7.5141 (1.8); 3.5151 (1.2); 3.5116 (1.0); 3.5018 (0.9); 3.4858(1.1); 3.4650 (1.5); 3.3898 (5.2); 3.2385 (0.4); 3.2262 (1.8); 3.2184 (0.6); 3.1920 (0.4); 2.8917 (1.3); 2.7491 (0.3); 2.7322(1.2); 2.6731 (0.4); 2.5663 (2.0); 2.5525 (4.1); 2.5386 (2.1); 2.5082 (48.1); 2.5040 (62.6); 2.4997 (46.6); 2.3309(0.4); 2.3068 (6.4); 1.2366 (1.2); −0.0002(1.1)

I-88: $^1$H-NMR(400.2 MHz, d$_6$-DMSO):

δ = 10.1895 (0.4); 9.5041 (5.0); 9.1977 (0.4); 9.1810 (0.4); 9.1257 (1.0); 8.9766 (16.0); 7.9528 (0.5); 7.8362(1.2); 7.8294 (1.3); 7.4845 (1.4); 7.4644 (1.6); 7.3308 (1.2); 7.3240 (1.2); 7.1204 (6.1); 7.1003 (1.4); 6.8748 (4.5); 6.5481 (1.9); 3.5829 (5.4); 3.5607 (1.2); 3.4727 (28.8); 3.4306 (1.4); 3.3364 (7.9); 2.8915 (2.8); 2.7315 (2.6); 2.6722(0.4); 2.5073 (49.1); 2.5032 (63.1); 2.4989 (47.0); 2.3305 (0.4); 2.2873 (5.0); 1.2589 (0.4); 1.2387 (1.9); 0.8526 (0.4); −0.0002 (0.9)

I-90: $^1$H-NMR(300.2 MHz, CDCl3):

δ = 9.2053 (16.0); 8.8944 (2.7); 8.8894 (3.0); 8.8806 (2.9); 8.8754 (2.7); 8.4759 (4.3); 8.4683 (4.3); 8.2257 (2.5); 8.1999 (2.8); 8.1637 (3.3); 8.1334 (3.9); 7.8356 (2.8); 7.8275 (2.8); 7.8052 (2.6); 7.7970 (3.0); 7.7819 (3.3); 7.4733 (2.5); 7.4593 (2.5); 7.4458 (2.4); 7.4315 (2.3); 7.2989 (23.1); 1.6446 (16.0); 1.3689 (0.4); 1.3221 (0.5); 1.2899 (2.0); 0.8904 (0.5); 0.8725 (0.5); 0.0363 (27.4)

BIOLOGICAL DATA

Example A: In Vivo Preventive Test on *Puccinia recondita* (Brown Rust on Wheat)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone//Tween® 80 and then diluted in water to the desired concentration.

The young plants of wheat were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Puccinia recondita* spores. The contaminated wheat plants were incubated for 24 hours at 20° C. and at 100% relative humidity and then for 10 days at 20° C. and at 70-80% relative humidity.

The test was evaluated 11 days after the inoculation. 0% means an efficacy which corresponds to that of the control plants while an efficacy of 100% means that no disease was observed.

In this test, the following compounds according to the invention showed efficacy between 70% and 79% at a concentration of 500 ppm of active ingredient: I-21

In this test, the following compounds according to the invention showed efficacy between 80% and 89% at a concentration of 500 ppm of active ingredient: I-05; I-13; I-16; I-17; I-32

In this test, the following compounds according to the invention showed efficacy between 90% and 100% at a concentration of 500 ppm of active ingredient: I-04; I-06; I-10; I-23

Example B: In Vivo Preventive Test on *Uromyces appendiculatus* (Bean Rust)

Solvent: 5% by volume of Dimethyl sulfoxide
10% by volume of Acetone
Emulsifier: 1 μl of Tween® 80 per mg of active ingredient The active ingredients were made soluble and homogenized in a mixture of Dimethyl sulfoxide/Acetone// Tween® 80 and then diluted in water to the desired concentration.

The young plants of bean were treated by spraying the active ingredient prepared as described above. Control plants were treated only with an aqueous solution of Acetone/Dimethyl sulfoxide/Tween®80.

After 24 hours, the plants were contaminated by spraying the leaves with an aqueous suspension of *Uromyces appendiculatus* spores. The contaminated bean plants were incubated for 24 hours at 20° C. and at 100% relative humidity and then for 10 days at 20° C. and at 70-80% relative humidity.

The test was evaluated 11 days after the inoculation. 0% means an efficacy which corresponds to that of the control plants while an efficacy of 100% means that no disease was observed.

In this test, the following compounds according to the invention showed efficacy between 70% and 79% at a concentration of 500 ppm of active ingredient: I-01; I-37

In this test, the following compounds according to the invention showed efficacy between 80% and 89% at a concentration of 500 ppm of active ingredient: I-03

In this test, the following compounds according to the invention showed efficacy between 90% and 100% at a concentration of 500 ppm of active ingredient: I-04; I-05; I-06; I-45

Example C: In Vivo Preventive Test on *Phakospora pachyrhizi* (Soybean Rust)

Solvent: 5% by volume of Dimethyl sulfoxide
10% by volume of Acetone
Emulsifier: of Tween® 80 per mg of active ingredient The active ingredients were made soluble and homogenized in a mixture of Dimethyl sulfoxide/Acetone// Tween® 80 and then diluted in water to the desired concentration.

The young plants of soybean were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Phakospora pachyrhizi* spores. The contaminated soybean plants were incubated for 24 hours at 24° C. and at 100% relative humidity and then for 11 days at 24° C. and at 70-80% relative humidity.

The test was evaluated 12 days after the inoculation. 0% means an efficacy which corresponds to that of the control plants while an efficacy of 100% means that no disease was observed.

In this test, the following compounds according to the invention showed efficacy between 70% and 79% at a concentration of 500 ppm of active ingredient: I-21; I-26; I-32

In this test, the following compounds according to the invention showed efficacy between 90% and 100% at a concentration of 500 ppm of active ingredient: I-05; I-08; I-10; I-13; I-16; I-17; I-23

In this test, the following compounds according to the invention showed efficacy between 70% and 79% at a concentration of 250 ppm of active ingredient: I-11; I-24; I-77

In this test, the following compounds according to the invention showed efficacy between 80% and 89% at a concentration of 250 ppm of active ingredient: I-27

In this test, the following compounds according to the invention showed efficacy between 90% and 100% at a concentration of 250 ppm of active ingredient: I-15; I-29; I-75

In this test, the following compounds according to the invention showed efficacy between 80% and 89% at a concentration of 100 ppm of active ingredient: I-42; I-63

In this test, the following compounds according to the invention showed efficacy between 90% and 100% at a concentration of 100 ppm of active ingredient: I-61

Example D: *Rhizoctonia solani* In Vitro Cell Test

Solvent: DMSO
Culture medium: 14.6 g anhydrous D-glucose (VWR), 7.1 g Mycological Peptone (Oxoid), 1.4 g granulated Yeast Extract (Merck), QSP 1 liter
Inoculum: mycelial suspension Fungicides were solubilized in DMSO and the solution used to prepare the required range of concentrations. The final concentration of DMSO used in the assay was 1%.

Inoculum was prepared from a pre-culture of *R. solani* grown in liquid medium by homogenization using a blender.

The concentration of ground mycelium in the inoculum was estimated and adjusted to the desired optical density (OD).

Fungicides were evaluated for their ability to inhibit mycelium growth in liquid culture assay. The compounds were added in the desired concentrations to culture medium containing the mycelial suspension. After 5 days of incubation, the fungicidal efficacy of compounds was determined by spectrometric measurement of mycelium growth. Inhibition of fungal growth was determined by comparing the absorbance values in wells containing the fungicides with the absorbance in control wells without fungicides.

In this test, the following compounds according to the invention showed efficacy between 70% and 79% at a concentration of 20 ppm of active ingredient: I-17; I-83; I-90

In this test, the following compounds according to the invention showed efficacy between 80% and 89% at a concentration of 20 ppm of active ingredient: I-23; I-36; I-37; I-51; I-55; I-87

In this test, the following compounds according to the invention showed efficacy between 90% and 100% at a concentration of 20 ppm of active ingredient: I-24; I-38

Example E: *Colletotrichum lindemuthianum* In Vitro Cell Test

Solvent: DMSO
Culture medium: 14.6 g anhydrous D-glucose (VWR), 7.1 g Mycological Peptone (Oxoid), 1.4 g granulated Yeast Extract (Merck), QSP 1 liter
Inoculum: spores suspension Fungicides were solubilized in DMSO and the solution used to prepare the required range of concentrations. The final concentration of DMSO used in the assay was ≤□1%.

A spore suspension of *C. lindemuthianum* was prepared and diluted to the desired spore density.

Fungicides were evaluated for their ability to inhibit spores germination and mycelium growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 70% and 79% at a concentration of 4 ppm of active ingredient: I-01; I-08; I-16; I-21; I-25; I-29; I-32; I-48; I-60; I-63

In this test the following compounds according to the invention showed efficacy between 80% and 89% at a concentration of 4 ppm of active ingredient: I-03; I-04; I-05; I-10; I-17; I-23; I-42; I-47; I-51; I-54

In this test, the following compounds according to the invention showed efficacy between 90% and 100% at a concentration of 4 ppm of active ingredient: I-06

In this test the following compounds according to the invention showed efficacy between 70% and 79% at a concentration of 20 ppm of active ingredient: I-02; I-11; I-14; I-15; I-20; I-22; I-42; I-47; I-54; I-57

In this test the following compounds according to the invention showed efficacy between 80% and 89% at a concentration of 20 ppm of active ingredient: I-01; I-04; I-08; I-10; I-13; I-16; I-18; I-21; I-25; I-29; I-37; I-50; I-51

In this test, the following compounds according to the invention showed efficacy between 90% and 100% at a concentration of 20 ppm of active ingredient: I-03; I-05; I-06; I-17; I-23; I-24; I-32; I-38

Example F: In Vivo Preventive Test on *Phakopsora* Test (Soybeans)

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for preventive activity, young plants were sprayed with the preparation of active compound at the stated rate of application. After the spray coating had dried on, the plants were inoculated with an aqueous spore suspension of the causal agent of soybean rust (*Phakopsora pachyrhizi*) and stay for 24 h without light in an incubation cabinet at approximately 24° C. and a relative atmospheric humidity of 95%.

The plants remained in the incubation cabinet at approximately 24° C. and a relative atmospheric humidity of approximately 80% and a day/night interval of 12 h.

The test was evaluated 7 days after the inoculation. 0% means an efficacy which corresponds to that of the untreated control, while an efficacy of 100% means that no disease is observed.

In this test, the following compounds according to the invention showed efficacy between 90% and 100% at a concentration of 250 ppm of active ingredient: I-04; I-06

The invention claimed is:

1. A compound of formula (I) or a salt thereof:

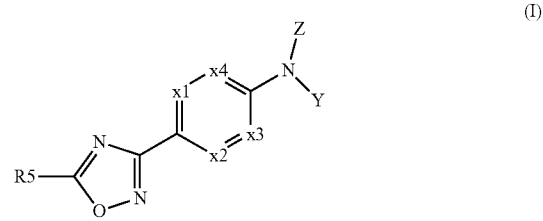

wherein:
X1 represents N or CR1;
X2 represents N or CR2;
X3 represents N or CR3;
X4 represents N or CR4;
wherein R1, R2, R3 and R4, when present, represent independently hydrogen, halogen or $C_1$-$C_3$-alkyl;
R5 represents $CF_3$ or $CF_2Cl$;
Z represents aryl, heteroaryl, $C_3$-$C_{10}$-carbocyclyl or 3- to 10-membered-heterocyclyl, wherein said aryl, heteroaryl, $C_3$-$C_{10}$-carbocyclyl or 3- to 10-membered-heterocyclyl, is optionally substituted by one or more substituents which may be the same or different, selected from the group consisting of —$SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$- alkylamino, $C_1$-$C_6$-alkylcarbonyl, $C_1$-$C_6$-alkoxycarbonyl, aminocarbonyl, aryl, aryl-$C_1$-$C_6$-alkyl and heteroaryl, wherein said aryl or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy; and Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl or heteroaryl wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy, provided that Z is not an unsubstituted piperidinyl nor a piperidinyl substituted by a $C_1$-$C_6$-alkoxycarbonyl when X1, X2 and X3 are CH, X4 is N, Y is H and R5 is $CF_3$, or when X1 and X2 are CH, X3 and X4 are N, Y is H and R5 is $CF_3$;

provided that Z is different from $C_3$-$C_{10}$-carbocyclyl when Y is C(=O)—$C_1$-$C_6$-alkyl, —C(=O)—O—$C_1$-$C_6$-alkyl, —C(=S)—$C_1$-$C_6$-alkyl or $C_1$-$C_6$-alkylsulfonyl and R5 is $CF_3$;

provided Z is not phenyl nor 6-membered heteroaryl when X1 and X2 are CH, X3 is CR3 with R3 is hydrogen or chlorine, X4 is N, Y is hydrogen or $C_1$-$C_6$-alkyl and R5 is $CF_3$, and provided the compounds of formula (I) is not:

Acetamide, 2,2,2-trifluoro-N-[(1R,2S)-2-phenylcyclohexyl]-N-[5-[5-(trifluoromethyl)-1,2,4-oxadiazol-3-yl]-2-pyridinyl] (2170456-65-0);

2-Pyridinamine, N-[(1R,2S)-2-phenylcyclohexyl]-5-[5-(trifluoromethyl)-1,2,4-oxadiazol-3-yl]- (2170451-91-7).

2. A compound of the formula (I) or a salt thereof according to claim 1 wherein R5 represents $CF_2Cl$.

3. A compound or salt according to claim 1

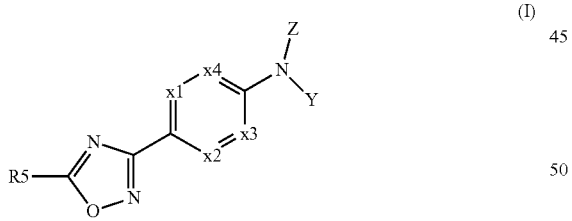

(I)

wherein:

X1 represents N or CR1 wherein R1 represents hydrogen, halogen or $C_1$-$C_3$-alkyl;
X2 represents N or CR2 wherein R2 represents hydrogen, halogen or $C_1$-$C_3$-alkyl;
X3 represents N or CR3 wherein R represents hydrogen, halogen or $C_1$-$C_3$-alkyl;
X4 represents N or CR4 wherein R represents hydrogen, halogen or $C_1$-$C_3$-alkyl;
R5 represents $CF_3$ or $CF_2Cl$;
Z represents 5- or 6-membered heteroaryl, wherein said heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl, aryl-$C_1$-$C_6$-alkyl and heteroaryl, wherein said aryl or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy;

and

Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl or heteroaryl, wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy.

4. The compound or salt according to claim 1

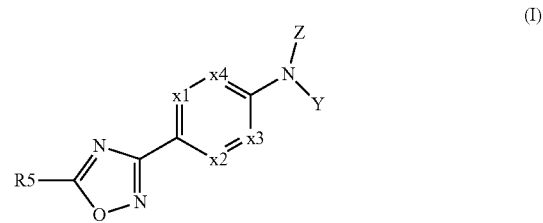

(I)

wherein:

X1 represents N or CR1 wherein R1 represents hydrogen, halogen or $C_1$-$C_3$-alkyl;
X2 represents N or CR2 wherein R2 represents hydrogen, halogen or $C_1$-$C_3$-alkyl;
X3 represents N or CR3 wherein R represents hydrogen, halogen or $C_1$-$C_3$-alkyl;
X4 represents N or CR4 wherein R represents hydrogen, halogen or $C_1$-$C_3$-alkyl;
R5 represents $CF_3$ or $CF_2Cl$;
Z represents phenyl or 5- or 6-membered heteroaryl, wherein said heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl, aryl-$C_1$-$C_6$-alkyl and heteroaryl, wherein said aryl or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy;

and

Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl or heteroaryl, wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy.

5. The compound or salt according to claim 1:

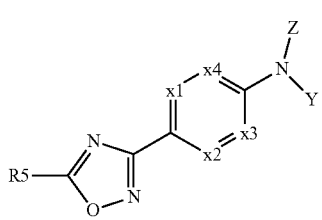

(I)

wherein:

X1 represents N or CR1 wherein R1 represents hydrogen, chloro or $C_1$-$C_3$-alkyl;

X2 represents N or CR2 wherein R2 represents hydrogen, chloro or $C_1$-$C_3$-alkyl;

X3 represents N or CR3 wherein R3 represents hydrogen, halogen or $C_1$-$C_3$-alkyl;

X4 represents N or CR4 wherein R4 represents hydrogen, halogen or $C_1$-$C_3$-alkyl;

R5 represents $CF_3$ or $CF_2Cl$;

Z represents $C_3$-$C_{10}$-carbocyclyl, naphthyl, $C_8$-$C_{10}$-heteroaryl, 3- to 10-membered-heterocyclyl, wherein said Z is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl, aryl-$C_1$-$C_6$-alkyl and heteroaryl, wherein said aryl or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy;

Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl or heteroaryl, wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy.

6. The compound or salt according to claim 1 wherein at least one of X1, X2, X3 and X4 is N and not more than two of X1, X2, X3 and X4 are N.

7. The compound or salt according to claim 1 wherein Z is substituted by one or more substituents which may be the same or different, selected from the group consisting of $SF_5$, halogen, cyano, hydroxy, amino, $C_1$-$C_6$-alkyl, $C_1$-$C_6$-haloalkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl.

8. The compound or salt of formula (I) according to claim 1 wherein Y is hydrogen, $C_1$-$C_3$-alkyl or —C(=O)—$C_1$-$C_6$-alkyl.

9. The compound or salt of formula (I) according to claim 1 wherein Z is phenyl.

10. The compound of formula (I) or salt according to claim 1 wherein Z is 5- or 6-membered heteroaryl.

11. A product comprising a compound or salt of claim 1 for controlling phytopathogenic fungi.

12. A method for controlling one or more unwanted phytopathogenic microorganisms which comprises applying one or more compounds of formula (I) and/or salts thereof to one or more of plants, plant parts, seeds, fruits or to soil in which plants grow:

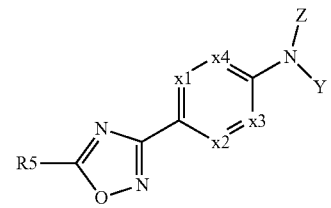

(I)

wherein:

X1 represents N or CR1;

X2 represents N or CR2;

X3 represents N or CR3;

X4 represents N or CR4;

wherein R1, R2, R3 and R4, when present, represent independently hydrogen, halogen or $C_1$-$C_3$-alkyl;

R5 represents $CF_3$ or $CF_2Cl$;

Z represents $C_3$-$C_{10}$-carbocyclyl, 3- to 10-membered-heterocyclyl, aryl or heteroaryl, wherein said $C_3$-$C_{10}$-carbocyclyl, 3- to 10-membered-heterocyclyl, aryl or heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl, aryl-$C_1$-$C_6$-alkyl and heteroaryl, wherein said aryl or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy; and Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl or heteroaryl wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy, provided that when Y is C(=O)—$C_1$-$C_6$-alkyl, —C(=O)—O—$C_1$-$C_6$-alkyl, —C(=S)—$C_1$-$C_6$-alkyl or $C_1$-$C_6$-alkylsulfonyl, Z is different from $C_3$-$C_{10}$-carbocyclyl;

provided that Z is different from $C_3$-$C_{10}$-carbocyclyl when Y is C(=O)—$C_1$-$C_6$-alkyl, —C(=O)—O—$C_1$-$C_6$-alkyl, —C(=S)—$C_1$-$C_6$-alkyl or $C_1$-$C_6$-alkylsulfonyl and R5 is $CF_3$.

13. A method for controlling one or more unwanted phytopathogenic microorganisms which comprises applying one or more compounds of formula (I) and/or salts thereof to plants, plant parts, seeds, fruits or to soil in which plants grow:

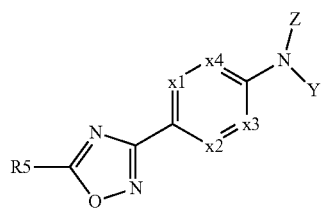

(I)

wherein:
X1 represents CR1 wherein R1 represents hydrogen, halogen or $C_1$-$C_3$-alkyl;
X2 represents CR2 wherein R2 represents hydrogen, halogen or $C_1$-$C_3$-alkyl;
X3 represents CR3 wherein R3 represents hydrogen, halogen or $C_1$-$C_3$-alkyl;
X4 represents CR4 wherein R4 represents hydrogen, halogen or $C_1$-$C_3$-alkyl;
R5 represents $CF_3$ or $CF_2Cl$;
Z represents phenyl or 5- or 6-membered heteroaryl, wherein said phenyl or heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl, aryl-$C_1$-$C_6$-alkyl and heteroaryl, wherein said aryl or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy; and
Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl or heteroaryl wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy.

14. A method for controlling unwanted phytopathogenic microorganisms which comprises applying one or more compounds of formula (I) and/or salts thereof to plants, plant parts, seeds, fruits or to soil in which plants grow:

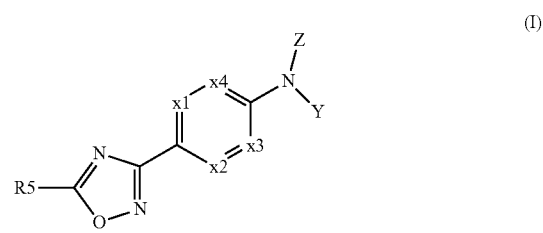

(I)

wherein:
X1 represents N or CR1 wherein R1 represents hydrogen, halogen or $C_1$-$C_3$-alkyl;
X2 represents N or CR2 wherein R2 represents hydrogen, halogen or $C_1$-$C_3$-alkyl;
X3 represents N or CR3 wherein R represents hydrogen, halogen or $C_1$-$C_3$-alkyl;
X4 represents N or CR4 wherein R represents hydrogen, halogen or $C_1$-$C_3$-alkyl;
R5 represents $CF_3$ or $CF_2Cl$;
Z represents 5- or 6-membered heteroaryl, wherein said heteroaryl is optionally substituted by one or more substituents which may be the same or different, selected from the group consisting of $SF_5$, halogen, cyano, hydroxy, amino, nitro, $C_1$-$C_6$-alkyl, $C_1$-$C_6$-cyanoalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio, $C_1$-$C_6$-alkyl-C(=O)—NH—, $C_3$-$C_{10}$-carbocyclyl, $C_3$-$C_{10}$-halocarbocyclyl, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, aminocarbonyl, aryl, aryl-$C_1$-$C_6$-alkyl and heteroaryl, wherein said aryl or heteroaryl is optionally substituted by one or more substituents, which may be the same or different, selected from the group consisting of halogen, $C_1$-$C_6$-alkyl, $C_1$-$C_6$-haloalkyl, $C_1$-$C_6$-alkoxy and $C_1$-$C_6$-haloalkoxy; and
Y represents hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, —C(=O)—$C_1$-$C_6$-alkyl, —C(=S)—$C_1$-$C_6$-alkyl, —C(=O)—O—$C_1$-$C_6$-alkyl, $C_1$-$C_6$-alkoxy, $C_1$-$C_6$-haloalkoxy, $C_1$-$C_6$-alkylsulfonyl, $C_1$-$C_6$-haloalkylsulfonyl, $C_3$-$C_{10}$-carbocyclyl, 3- to 10-membered-heterocyclyl, aryl or heteroaryl, wherein said Y is optionally substituted with halogen, cyano, $C_1$-$C_6$-alkyl, $C_1$-$C_6$-haloalkyl, $C_1$-$C_6$-alkoxy or $C_1$-$C_6$-haloalkoxy.

15. A method for controlling unwanted phytopathogenic microorganisms which comprises applying one or more compounds of formula (I) and/or salts thereof to plants, plant parts, seeds, fruits or to soil in which plants grow:

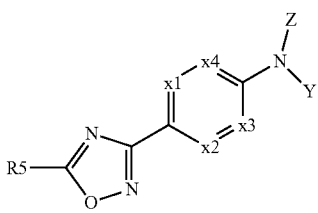

(I)

wherein:
X1 represents N or CH;
X2 represents N or CH;
X3 represents N or CR3 wherein R3 represents hydrogen, chloro or $C_1$-$C_3$-alkyl;
X4 represents N or CR4 wherein R4 represents hydrogen, chloro or $C_1$-$C_3$-alkyl;
and wherein at least one of X1, X2, X3 and X4 is N and not more than two of X1, X2, X3 and X4 are N;
R5 is $CF_3$ or $CH_2Cl$;
Z represents phenyl or a 5- or 6-membered heteroaryl, wherein said phenyl or heteroaryl is optionally substituted by one or more substituents which may be the same or different, selected from $SF_5$, cyano, amino, halogen, hydroxyl, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, hydroxy$C_1$-$C_4$-alkyl, $C_1$-$C_4$-alkoxy, $C_1$-$C_4$-alkylamino, di$C_1$-$C_4$-alkylamino, $C_1$-$C_4$-alkylcarbonyl, $C_1$-$C_4$-alkoxycarbonyl, $C_1$-$C_6$-alkyl-C(=O)—NH— and aminocarbonyl; and
Y represents hydrogen or $C_1$-$C_3$-alkyl.

16. A composition comprising one or more compounds of formula (I) and/or salts according to claim 1 and one or more acceptable carriers.

17. The compound or salt of formula (I) according to claim 1 wherein aryl is phenyl.

18. The method according to claim 13, wherein Y is hydrogen, $C_1$-$C_3$-alkyl or —C(=O)—$C_1$-$C_6$-alkyl.

19. The method according to claim 14, wherein at least one of X1, X2, X3 and X4 is N and not more than two of X1, X2, X3 and X4 are N.

20. The method according to claim 13, wherein Z represents phenyl or 5- or 6-membered heteroaryl, wherein said phenyl or heteroaryl is substituted by one or more substituents which may be the same or different, selected from the group consisting of $SF_5$, halogen, cyano, hydroxy, amino, $C_1$-$C_6$-alkyl, $C_1$-$C_6$-haloalkyl, $C_2$-$C_6$-alkenyl$C_2$-$C_6$-alkynyl, $C_1$-$C_6$-alkoxy, hydroxy-$C_1$-$C_6$-alkyl, $C_1$-$C_6$-alkylamino, di$C_1$-$C_6$-alkylamino, $C_1$-$C_6$-alkylcarbonyl, $C_1$-$C_6$-alkoxycarbonyl, $C_1$-$C_6$-alkyl-C(=O)—NH— and aminocarbonyl.

* * * * *